US008568974B2

(12) United States Patent
Willman et al.

(10) Patent No.: US 8,568,974 B2
(45) Date of Patent: Oct. 29, 2013

(54) IDENTIFICATION OF NOVEL SUBGROUPS OF HIGH-RISK PEDIATRIC PRECURSOR B ACUTE LYMPHOBLASTIC LEUKEMIA, OUTCOME CORRELATIONS AND DIAGNOSTIC AND THERAPEUTIC METHODS RELATED TO SAME

(75) Inventors: Cheryl L. Willman, Albuquerque, NM (US); Richard Harvey, Placitas, NM (US); George S. Davidson, Albuquerque, NM (US); Xuefei Wang, Albuquerque, NM (US); Susan R Atlas, Albuquerque, NM (US); Edward J. Bedrick, Albuquerque, NM (US); Iming L. Chen, Albuquerque, NM (US)

(73) Assignees: STC.UNM, Albuquerque, NM (US); Sandia Corporation, Albuquerque, NM (US)

( * ) Notice: Subject to any disclaimer, the term of this patent is extended or adjusted under 35 U.S.C. 154(b) by 228 days.

(21) Appl. No.: 12/734,542

(22) PCT Filed: Nov. 14, 2008

(86) PCT No.: PCT/US2008/012821
§ 371 (c)(1),
(2), (4) Date: Oct. 12, 2010

(87) PCT Pub. No.: WO2009/064481
PCT Pub. Date: May 22, 2009

(65) Prior Publication Data
US 2011/0045999 A1 Feb. 24, 2011

Related U.S. Application Data

(60) Provisional application No. 61/003,048, filed on Nov. 14, 2007.

(51) Int. Cl.
*C12Q 1/68* (2006.01)
*G01N 33/53* (2006.01)

(52) U.S. Cl.
USPC .............................................. 435/6.1; 435/7.1

(58) Field of Classification Search
None
See application file for complete search history.

(56) References Cited

U.S. PATENT DOCUMENTS

2007/0072178 A1 3/2007 Haferlach
2007/0207459 A1* 9/2007 Dugas et al. ...................... 435/6

FOREIGN PATENT DOCUMENTS

WO  2006009915 A2  1/2006
WO  2006071088 A1  7/2006

OTHER PUBLICATIONS

Filshie et al (Leukemia, 1998, 12(3): Abstract).*
Tockman et al (Cancer Res., 1992, 52:2711s-2718s).*
Alberts et al. (Molecular Biology of the Cell, 3rd edition, 1994, p. 465).*
Greenbaum et al. (Genome Biology, 2003, vol. 4, Issue 9, pp. 117.1-117.8).*
Ries LAG, Wilbert D, Krapcho M, et al. SEER Cancer Statistics Review. 1975-2005. NIH publication. Bethesda, Md.: National Cancer Institute, Bethesda, MD; 2008:v.
Smith M, Arthur D, Camitta B, et al. Uniform approach to risk classification and treatment assignment for children with acute lymphoblastic leukemia. J Clin Oncol. 1996;14:18-24.
Pieters R, Carroll WL. Biology and treatment of acute lymphoblastic leukemia. Pediatr Clin North Am. 2008;55:1-20, ix.
Armstrong SA, Look AT. Molecular genetics of acute lymphoblastic leukemia. J Clin Oncol. 2005;23:6306-6315.
Yeoh EJ, Ross ME, Shurtleff SA, et al. Classification, subtype discovery, and prediction of outcome in pediatric acute lymphoblastic leukemia by gene expression profiling. Cancer Cell. 2002;1:133-143.
Moos PJ, Raetz EA, Carlson MA, et al. Identification of gene expression profiles that segregate patients with childhood leukemia. Clin Cancer Res. 2002;8:3118-3130.
Wilson CS, Davidson GS, Martin SB, et al. Gene expression profiling of adult acute myeloid leukemia identifies novel biologic clusters for risk classification and outcome prediction. Blood. 2006;108:686-696.
Shuster JJ, Camitta BM, Pullen J, et al. Identification of newly diagnosed children with acute lymphocytic leukemia at high risk for relapse. Cancer Res Ther Control. 1999;9:101-107.
Borowitz MJ, Devidas M, Hunger SP, et al. Clinical significance of minimal residual disease in childhood acute lymphoblastic leukemia and its relationship to other prognostic factors: A Children's Oncology Group study. Blood, 2008; 111:5477-5485.
Nachman JB, Sather HN, Sensel MG, et al. Augmented post-induction therapy for children with high-risk acute lymphoblastic leukemia and a slow response to initial therapy. N Engl J Med. 1998; 338:1663-1671.
Seibel NL, Steinherz PG, Sather HN, et al. Early postinduction intensification therapy improves survival for children and adolescents with high-risk acute lymphoblastic leukemia: a report from the Children's Oncology Group. Blood. 2008;111:2548-2555.
Borowitz MJ, Pullen DJ, Shuster JJ, et al. Minimal residual disease detection in childhood precursor-B-cell acute lymphoblastic leukemia: relation to other risk factors. A Children's Oncology Group study. Leukemia. 2003;17:1566-1572.
Davidson GS, Martin S, Boyack KW, et al. Robust Methods for Microarray Analysis, In: Akay M, ed. Genomics and Proteomics Engineering in Medicine and Biology. Hoboken, New Jersey: IEEE Press ; Wiley; 2007:99-130.
Tomlins SA, Rhodes DR, Perner S, et al. Recurrent fusion of TMPRSS2 and ETS transcription factor genes in prostate cancer. Science. 2005;310:644-648.
Bland JM, Altman DG. The logrank test. BMJ. 2004;326:1073.
Armitage P. Berry G. Statistical methods in medical research (ed 3rd). Oxford ; Boston: Blackwell Scientific Publications; 1994.
Bewick V, Cheek L, Ball J. Statistics review 12: survival analysis. Crit Care. 2004;8:389-394.

(Continued)

*Primary Examiner* — Sean Aeder
(74) *Attorney, Agent, or Firm* — Henry D. Coleman; R. Neil Sudol

(57) ABSTRACT

The present invention relates to the identification of genetic markers patients with high risk B-precursor acute lymphoblastic leukemia (B-ALL) and associated methods and their relationship to therapeutic outcome. The present invention also relates to diagnostic, prognostic and related methods using these genetic markers, as well as kits which provide microchips and/or immunoreagents for performing analysis on leukemia patients.

25 Claims, 7 Drawing Sheets

(56) References Cited

OTHER PUBLICATIONS

Bhojwani D, Kang H. Menezes RX, et al. Gene expression signatures predictive of early response and outcome in high-risk childhood acute lymphoblastic leukemia: a Children's Oncology Group study. J Clin Oncol. 2008; 26:4376-4384.

Fine BM, Stanulla M, Schrappe M. et al. Gene expression patterns associated with recurrent chromosomal translocations in acute lymphoblastic leukemia. Blood. 2004;103:1043-1049.

van Delft FW, Bellotti T, Luo Z, et al. Prospective gene expression analysis accurately subtypes acute leukemia in children and establishes a commonality between hyperdiploidy and t(12;21) in acute lymphoblastic leukaemia. Br J Haematol. 2005;130:26-35.

Coustan-Smith E, Sancho J, Behm FG, et al. Prognostic importance of measuring early clearance of leukemic cells by flow cytometry in childhood acute lymphoblastic leukemia. Blood. 2002;100:52-58.

Steinherz PG, Gaynon PS, Breneman JC, et al. Cytoreduction and prognosis in acute lymphoblastic leukemia—the importance of early marrow response: report from the Childrens Cancer Group. J Clin Oncol. 1996;14:389-396.

Bhatia S, Sather HN, Heerema NA, Trigg ME, Gaynon PS, Robison LL. Racial and ethnic differences in survival of children with acute lymphoblastic leukemia. Blood. 2002;100:1957-1964.

Pollock BH, DeBaun MR, Camitta BM, et al. Racial differences in the survival of childhood B-precursor acute lymphoblastic leukemia: a Pediatric Oncology Group Study. J Clin Oncol. 2000;18:813-823.

Dworzak MN, Forschi G, Printz D, et al. CD99 expression in T-lineage ALL: implications for flow cytometric detection of minimal residual disease. Leukemia. 2004;18:703-708.

Wilkerson AE, Glasgow MA, Hiatt KM. Immunoreactivity of CD99 in invasive malignant melanoma. J Cutan Pathol. 2006;33:663-666.

Scotlandi K, Perdichizzi S, Bernard G, et al. Targeting CD99 in association with doxorubicin: an effective combined treatment for Ewing's sarcoma. Eur J Cancer. 2006;42:91-96.

Chaturvedi P, Singh AP, Moniaux N, et al. MUC4 mucin potentiates pancreatic tumor cell proliferation, survival, and invasive properties and interferes with its interaction to extracellular matrix proteins. Mol Cancer Res. 2007;5:309-320.

Moniaux N, Chaturvedi P, Varshney GC, et al. Human MUC4 mucin induces ultra-structural changes and tumorigenicity in pancreatic cancer cells. Br J Cancer. 2007;97:345-357.

Juric D, Lacayo NJ, Ramsey MC, et al. Differential gene expression patterns and interaction networks in BCR-ABL-positive and -negative adult acute lymphoblastic leukemias. J Clin Oncol. 2007;25:1341-1349.

Kameda H, Ishigami H, Suzuki M, Abe T, Takeuchi T. Imatinib mesylate inhibits proliferation of rheumatoid synovial fibroblast-like cells and phosphorylation of Gab adapter proteins activated by platelet-derived growth factor. Clin Exp Immunol. 2006;144:335-341.

Zukerberg LR, DeBernardo RL, Kirley SD, et al. Loss of cables, a cyclin-dependent kinase regulatory protein, is associated with the development of endometrial hyperplasia and endometrial cancer. Cancer Res. 2004;64:202-208.

Zhang H, Duan HO, Kirley SD, Zukerberg LR, Wu CL. Aberrant splicing of cables gene, a CDK regulator, in human cancers. Cancer Biol Ther. 2005;4:1211-1215.

Dong Q, Kirley S, Rueda B, Zhao C, Zukerberg L, Oliva E. Loss of cables, a novel gene on chromosome 18q, in ovarian cancer. Mod Pathol. 2003;16:863-868.

Kirley SD, D'Apuzzo M, Lauwers GY, Graeme-Cook F, Chung DC, Zukerberg LR. The Cables gene on chromosome 18Q regulates colon cancer progression in vivo. Cancer Biol Ther. 2005;4:861-863.

Ross ME, Zhou X, Song G, et al. Classification of pediatric acute lymphoblastic leukemia by gene expression profiling. Blood. 2003;102:2951-2959.

Mullighan CG, Miller CB, Su X, et al. ERG deletions define a novel subtype of B-progenitor acute lymphoblastic leukemia. Blood. 2007;110:212A-213A.

Hoffmann, K, Firth MJ, Beesley AH, et al. Prediction of relapse in paediatric pre-B acute lymphoblastic leukaemia using a three-gene risk index. Br J Haematol. 2008;140:655-664.

Gandemer V, et al., Five distinct biological processes and 14 differentially expressed genes characterize TEL/AML1-positive leukemia. BMC Genomics 2007;8:385.

Timson, G. et al., High level expression of N-acetylglucosamine-6-O-sulfotransferase is characteristic of a subgroup of paediatric precursor-B acute lymphoblastic leukaemia. Cancer Lett. 2006; 242:239-244.

* cited by examiner

IDENTIFICATION OF NOVEL SUBGROUPS OF HIGH-RISK PEDIATRIC PRECURSOR B ACUTE LYMPHOBLASTIC LEUKEMIA, OUTCOME CORRELATIONS AND DIAGNOSTIC AND THERAPEUTIC METHODS RELATED TO SAME

The present application claims the benefit of priority of U.S. provisional application Ser. No. 61/003,048, filed Nov. 14, 2007, entitled "Identification of Novel Subgroups of High-risk Pediatric Precursory B Acute Lymphoblastic Lukemia (B-ALL) by Unsupervised Microarray Analysis Clinical Correlates and Therapeutic Implications. A Children's Oncology Group (COG) Study", the entire contents of said application being incorporated by reference herein in its entirety.

RELATED APPLICATIONS AND GOVERNMENT SUPPORT

This invention was made with government support under a grant from the National Institutes of Health (National Cancer Institute), Grant No. 5 U01CA1114762.03 SPECS. The U.S. Government has certain rights in this invention.

FIELD OF THE INVENTION

The present invention relates to the identification of genetic markers patients with high risk B-precursor acute lymphoblastic leukemia (B-ALL) and associated methods and their relationship to therapeutic outcome. The present invention also relates to diagnostic, prognostic and related methods using these genetic markers, as well as kits which provide microchips and/or immunoreagents for performing analysis on leukemia patients.

BACKGROUND OF THE INVENTION

The majority of children and adolescents with B-precursor acute lymphoblastic leukemia (ALL) have good responses to current therapy with 5-year survival rates of 84% in 1996-2003, as compared to 54% in 1975-77.[1] To optimize the risk/benefit ratio, patients are stratified for treatment intensity based upon their risk of relapse.[2] The majority of patients have prognostic factors that place them into the favorable or standard risk treatment groups. These patients generally have long relapse free survivals (RFS), although prediction of the individual patients who will fail therapy still remains a significant problem. Patients in the high risk treatment group are fewer in number and have not been as well studied. A detailed examination of this cohort of patients may provide insights into the genes and pathways that are fundamentally associated with outcome.

The white blood cell (WBC) count, age and presence of extramedullary disease at the time of diagnosis have been the primary criteria for assigning B-precursor ALL patients to risk groups.[3] These groups have been further refined by the identification of sentinel genetic alterations (e.g., BCR/ABL or TEL/AML1 fusions) and the rate of response to initial treatment.[4] The considerable diversity and varying responses to therapy has led to an effort to further refine risk stratification. Molecular techniques are being explored in order to classify patients on the basis of their leukemic cell gene expression signatures.[5,6] Previous microarray studies have not only been effective in the identification of subtypes of leukemia, but in some cases they have also found these signatures to be associated with outcome.[5,7]

The high-risk ALL Therapeutically Applicable Research to Generate Effective Treatments (TARGET) pilot project is a partnership between the National Cancer Institute and the Children's Oncology Group (COG) designed to use genomics to identify and validate therapeutic targets. We analyzed specimens from 207 of 272 (75%) of high-risk B-precursor ALL patients from the COG P9906 clinical trial in an effort to identify subgroups of these high-risk patients that were characterized by unique gene expression profiles or signatures. Our objectives in this study were three-fold: 1) to identify subtypes of high-risk B-ALL defined by characteristic gene signatures, 2) to determine if these subtypes are associated with specific clinical features and 3) to analyze the signature genes to gain insight into the biology of the subtypes. The results from these analyses may lead to improved diagnostics, modified definitions of risk-categories and development of new targeted therapies.

BRIEF DESCRIPTION OF THE INVENTION

Figure 1A:
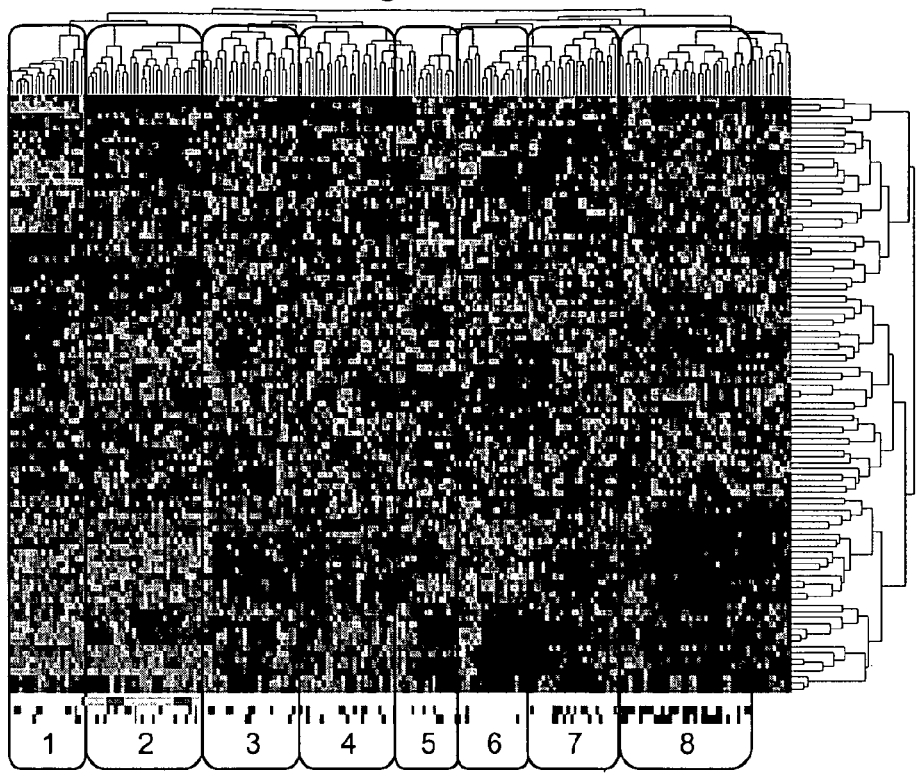
FIG. 1 shows the clustering of COG P9906 samples. In Panel A hierarchical clustering was used to identify groups of samples with related gene expression. The 100 probe sets are shown in rows and the 207 samples in columns. Shades of red depict expression levels higher than the median while greens indicate lower levels of expression. Colored boxes highlight the identification of eight groups. Bars across the bottom denote translocation groups (bright green for t(1;19); yellow for 11q23 rearrangements; dark green for similar to t(1;19), outcome (red for relapse) and race (blue for Hispanic/Latino). In Panel B, VxInsight was used to identify seven distinct clusters of ALL based on gene expression profiles. The data are visualized as a 3-dimensional terrain map with 2-dimensional distances reflecting gene expression profile correlates and the third dimension representing cluster membership density. Overlaps with the dominant signatures identified by hierarchical clustering are illustrated by the colors as indicated in the insert.
FIG. 1C shows an example of probe set with outlier group at high end. Red line indicates signal intensities for all 207 samples for probe 212151_at. Vertical blue lines depict partitioning of samples into thirds. A least-squares curve fit is applied to the middle third of the samples and the resulting trend line is shown in yellow. Different sample groups are illustrated by the dashed lines at the top right. As shown by the double arrowed lines, the median value from each of these groups is compared to the trend line.

Accurate risk stratification constitutes the fundamental paradigm of treatment in acute lymphoblastic leukemia (ALL), allowing the intensity of therapy to be tailored to the patient's risk of relapse. The present invention evaluates a gene expression profile and identifies prognostic genes of cancers, in particular leukemia, more particularly high risk B-precursor acute lymphoblastic leukemia (B-ALL), including high risk pediatric acute lymphoblastic leukemia. The present invention provides a method of determining the existence of high risk B-precursor ALL in a patient and predicting therapeutic outcome of that patient. The method comprises the steps of first establishing the threshold value of at least two (2) or three (3) prognostic genes of high risk B-ALL, or four (4) prognostic genes, at least five (5) prognostic genes, at least 6, at least 7, at least 8, at least 9, at least 10, at least 11, at least 12, at least 13, at least 13, at least 14, at least 15, at least 16, at least 17, at least 18, at least 19, at least 20, at least 21, at least 22, at least 23 and 24 or more prognostic genes which are described in the present specification, especially Table 1P and 1F. Then, the amount of the prognostic gene(s) from a patient inflicted with high risk B-ALL is determined. The amount of the prognostic gene present in that patient is compared with the established threshold value (a predetermined value) of the prognostic gene(s) which is indicative of therapeutic success or failure, whereby the prognostic outcome of the patient is determined. The prognostic gene may be a gene which is indicative of a poor (bad) prognostic outcome (Table 1P) or a favorable (good) outcome (Table 1G). Analyzing expression levels of these genes provides accurate insight (diagnostic and prognostic) information into the likelihood of a therapeutic outcome, especially in a high risk B-ALL patient.

Prognostic genes which are indicative of therapeutic success in high risk B-ALL include the following: AGAP1 (Arf-GAP with GTPase domain, ankyrin repeat and PH domain 1, referred to as CENTG2 herein); PTPRM (protein tyrosine phosphatase, receptor type, M); STAP1 (signal transducing adaptor family member 1); CCNJ (cyclin J); PCDH17 (procadherin 17); MCAM (melanoma cell adhesion molecule); CAPN3 (calpain 3); CABLES1 (Cdk5 and Abl enzyme substrate 1); GPR155 (G protein-coupled receptor 155). These appear in Table 1G, hereinbelow.

Prognostic genes which are indicative of therapeutic failure in high risk B-ALL include the following: MUC4 (mucin 4); GPR110 (G protein-coupled receptor 110); IGJ (immunoglobulin J polypeptide); NRXN3 (neurexin 3); CD99 (CD99 molecule); CRLF2 (cytokine receptor-like factor 2); ENAM (enamelin); TP53INP1 (tumor protein p53 inducible nuclear protein 1); IFITM1 (interferon induced transmembrane protein 1); IFITM2 (interferon induced transmembrane protein 2); IFITM3 (interferon induced transmembrane protein 3); TTYH2 (tweety homolog 2); SEMA6A (semaphorin 6A); TNFSF4 (tumor necrosis factor superfamily, member 4); and SLC37A3 (solute carrier family 37, member 3), of which MUC4, GPR110 and IGJ are particularly important prognostic genes of therapeutic failure within this group. These appear in Table 1P, hereinbelow.

In certain embodiments, the amount of the prognostic gene is determined by the quantitation of a transcript encoding the sequence of the prognostic gene; or a polypeptide encoded by the transcript. The quantitation of the transcript can be based on hybridization to the transcript. The quantitation of the polypeptide can be based on antibody detection or a related method. The method optionally comprises a step of amplifying nucleic acids from the tissue sample before the evaluating (per analysis). In a number of embodiments, the evaluating is of a plurality of prognostic genes, preferably at least two (2) prognostic genes, at least three (3) prognostic genes, at least four (4) prognostic genes, at least five (5) prognostic genes, at least six (6) prognostic genes, at least seven (7) prognostic genes, at least eight (8) prognostic genes, at least nine (9) prognostic genes, at least ten (10) prognostic genes, at least eleven (11) prognostic genes, at least twelve (12) prognostic genes, at least thirteen (13) prognostic genes, at least fourteen (14) prognostic genes, at least fifteen (15) prognostic genes, at least sixteen (16) prognostic genes, at least seventeen (17) prognostic genes, at least eighteen (18) prognostic genes, at least nineteen (19) prognostic genes, at least twenty (20) prognostic genes, at least twenty-one (21) prognostic genes, at least twenty-two (22) prognostic genes, at least twenty-three (23) prognostic genes, including as many as twenty-four (24) or more prognostic genes. The prognosis which is determined from measuring the prognostic genes contributes to selection of a therapeutic strategy, which may be a traditional therapy for B-precursor ALL (where a favorable prognosis is determined from measurements), or a more aggressive therapy based upon a traditional therapy or non-traditional therapy (where an unfavorable prognosis is determined from measurements).

The present invention is directed to methods for outcome prediction and risk classification in leukemia, especially a high risk classification in B precursor acute lymphoblastic leukemia (ALL), especially in children. In one embodiment, the invention provides a method for classifying leukemia in a patient that includes obtaining a biological sample from a patient; determining the expression level for a selected gene product, more preferably a group of selected gene products to yield an observed gene expression level; and comparing the observed gene expression level for the selected gene product(s) to control gene expression levels (preferably including a predetermined level). The control gene expression level can be the expression level observed for the gene product(s) in a control sample, or a predetermined expression level for the gene product. An observed expression level (higher or lower) that differs from the control gene expression level is indicative of a disease classification. In another aspect, the method can include determining a gene expression profile for selected gene products in the biological sample to yield an observed gene expression profile; and comparing the observed gene expression profile for the selected gene products to a control gene expression profile for the selected gene products that correlates with a disease classification, for example ALL, and in particular high risk B precursor ALL; wherein a similarity between the observed gene expression profile and the control gene expression profile is indicative of the disease classification (e.g., high risk B-all poor or favorable prognostic).

The disease classification can be, for example, a classification preferably based on predicted outcome (remission vs therapeutic failure); but may also include a classification based upon clinical characteristics of patients, a classification based on karyotype; a classification based on leukemia subtype; or a classification based on disease etiology. Where the classification is based on disease outcome, the observed gene product is preferably a gene product selected from at least two or three of the following group of five gene products, more preferably three, four or all five gene products: MUC4 (Mucin 4, cell surface associated), GRP110 (G protein-coupled receptor 110), IGJ (Immunoglobulin J polypeptide, linker protein for immunoglobulin alpha and mu polypeptides), CENTG2 (Centaurin, gamma 2) and PTPRM (protein tyrosine phosphatase, receptor type, M). Expression levels of at least two of the first three gene products (MUC4, GRP110, IGJ) which are higher than a control group evidence poor prognosis (poor responders to traditional anti-leukemia therapy) for a therapeutic outcome using traditional therapy, whereas expression levels of the last two gene products (CENTG2, PTPRM) which are higher than a control group evidence favorable (good responders to traditional anti-leukemia therapy) prognosis to traditional therapy. Preferably at least two gene products from the group are expressed, more preferably at least three, at least four and all five gene products. Alternatively, the invention may rely on measuring at least two of the nine (9) gene products (including CENT2G and PTPRM) of those listed in Table 1G (favorable therapeutic outcome), and/or at least two or more of the fifteen (15) gene products of those listed in Table 1P (unfavorable therapeutic outcome) or any combination of the twenty-four (24) gene products which appear in Tables 1P and 1F, below. Measurement of all 24 gene products set forth in Table 1P and 1F, below, may also be performed to provide an accurate assessment of therapeutic intervention.

The invention further provides for a method for predicting a patient falls within a particular group of high risk B-ALL patients and predicting therapeutic outcome in that B ALL leukemia patient, especially pediatric B-ALL that includes obtaining a biological sample from a patient; determining the expression level for selected gene products associated with outcome to yield an observed gene expression level; and comparing the observed gene expression level for the selected gene product(s) to a control gene expression level for the selected gene product. The control gene expression level for the selected gene product can include the gene expression level for the selected gene product observed in a control sample, or a predetermined gene expression level for the selected gene product; wherein an observed expression level that is different from the control gene expression level for the selected gene product(s) is indicative of predicted remission. The method preferably may determine gene expression levels of at least two gene products selected from the group consisting of MUC4, GRP110, IGJ, CENT2G and PTPRM, more preferably at least three, four or all five gene products. Alternatively, at least two, three, four, five, six, seven, eight, nine, ten, eleven, twelve, thirteen, fourteen, fifteen, sixteen, seventeen, eighteen, nineteen, twenty, twenty-one, twenty-two, twenty-three or twenty-four or gene products selected from the group consisting of MUC4; GPR110; IGJ; NRXN3; CD99; CRLF2; ENAM; TP53INP1; IFITM1; IFITM2; IFITM3; TTYH2; SEMA6A; TNFSF4; SLC37A3; CENTG2; PTPRM; STAP1; CCNJ; PCDH17; MCAM; CAPN3; CABLES1; and GPR155 or as otherwise described herein are measured, compared to predetermined values (e.g. from a control sample) and then assessed to determine the likelihood of a favorable or unfavorable therapeutic outcome and then providing a therapeutic approach consistent with the analysis of the express of the measured gene products. The present method may include measuring expression of at least two gene products up to 24 or more gene products according to Tables 1P and 1G. In certain preferred aspects of the invention, the expression levels of all 24 gene products (Tables 1P and 1G) may be determined and compared to a predetermined gene expression level, wherein a measurement above or below a predetermined expression level is indicative of the likelihood of a favorable therapeutic response (continuous complete remission or CCR) or therapeutic failure. In the case where therapeutic failure is predicted, the use of more aggressive protocols of traditional anti-cancer therapies (higher doses and/or longer duration of drug administration) or experimental therapies may be advisable.

Optionally, the method further comprises determining the expression level for other gene products within the list of gene products otherwise disclosed herein and comparing in a similar fashion the observed gene expression levels for the selected gene products with a control gene expression level for those gene products, wherein an observed expression level for these gene products that is different from (above or below) the control gene expression level for that gene product is further indicative of predicted remission (favorable prognosis) or relapse (unfavorable prognosis).

The invention further includes a method for treating leukemia comprising administering to a leukemia patient a therapeutic agent that modulates the amount or activity of the gene product(s) associated with therapeutic outcome, in particular, MUC4, GPR110 (inhibited or downregulated) or CENTG2 or PTPRM (enhanced or upregulated). Preferably, the method modulates (enhancement/upregulation of a gene product associated with a favorable or good therapeutic outcome or inhibition/downregulation of a gene product associated with a poor or unfavorable therapeutic outcome as measured by comparison with a control sample or predetermined value) at least two of the five gene products as set forth above, three of the gene products, four of the gene products or all five of the gene products. In addition, the therapeutic method according to the present invention also modulates at least two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four of a number of gene products in Tables 1P and 1G as indicated or otherwise described herein, any one or more of the gene products of Table 1P: MUC4; GPR110; IGJ; NRXN3; CD99; CRLF2; ENAM; TP53INP1; IFITM1; IFITM2; IFITM3; TTYH2; SEMA6A; TNFSF4; and SLC37A3 as being inhibited or downregulated and/or any one or more of the gene products of Table 1F: CENTG2; PTPRM; STAP1; CCNJ; PCDH17; MCAM; CAPN3; CABLES1; GPR155 as being enhanced or upregulated as measured in comparison to a control expression or predetermined value.

Also provided by the invention is an in vitro method for screening a compound useful for treating leukemia, especially high risk B-ALL. The invention further provides an in vivo method for evaluating a compound for use in treating leukemia, especially high risk B-ALL. The candidate compounds are evaluated for their effect on the expression level(s) of one or more gene products associated with outcome in leukemia patients (for example, Table 1P and 1G and as otherwise described herein), especially high risk B-ALL, preferably at least two of those gene products, at least three of those gene products, at least four of those gene products, at least five of those gene products, at least six of those gene products, at least seven of those gene products, at least eight of those gene products, at least nine of those gene products, at least ten of those gene products, at least eleven of those gene products, at least twelve of those gene products, at least thirteen of those gene products, at least fourteen of those gene products, at least fifteen of those gene products, at least sixteen of those gene products, at least seventeen of those gene products, at least eighteen of those gene products, at least twenty of those gene products, at least twenty-one of those gene products, at least twenty-two of those gene products, at least twenty-three of those gene products or twenty-four of those gene products may be measured to determine a therapeutic outcome.

The preferred five gene products are as identified for example, using probe sets (MUC4, GPR110, IGJ, CENTG2, PTPRM). These 5 genes and their expression above or below a predetermined expression level are more predictive of overall outcome. As shown below, at least two or more of the gene products which are presented in tables 1P or 1G may be used to predict therapeutic outcome. This predictive model is tested in an independent cohort of high risk pediatric B-ALL cases (20) and is found to predict outcome with extremely high statistical significance (p-value $<1.0^{-8}$). It is noted that the expression of gene products of at least two of the five genes listed above, as well as additional genes from the list appearing in Tables 1P and 1F and in certain preferred instances, the expression of all 24 gene products of Table 1P and 1F may be measured and compared to predetermined expression levels to provide the greater degrees of certainty of a therapeutic outcome.

TABLE 1P (Poor/Unfavorable Outcome)

| Symbol | | GeneID | Location |
|---|---|---|---|
| MUC4 | mucin 4 | 4585 | 3q29 |
| GPR110 | G protein-coupled receptor 110 | 266977 | 6p12 |
| IGJ | immunoglobulin J polypeptide | 3512 | 4q21 |
| NRXN3 | neurexin 3 | 9369 | 14q31 |
| CD99 | CD99 molecule | 4267 | Xp22; Yp11 |
| CRLF2 | cytokine receptor-like factor 2 | 64109 | Xp22; Yp11 |
| ENAM | enamelin | 10117 | 4q13 |
| TP53INP1 | tumor protein p53 inducible nuclear protein 1 | 94241 | 8q22 |
| IFITM1 | interferon induced transmembrane protein 1 | 8519 | 11p15 |
| IFITM2 | interferon induced transmembrane protein 2 | 10581 | 11p15 |
| IFITM3 | interferon induced transmembrane protein 3 | 10410 | 11p15 |
| TTYH2 | tweety homolog 2 | 94015 | 17q25 |
| SEMA6A | semaphorin 6A | 57556 | 5q23 |
| TNFSF4 | tumor necrosis factor superfamily, member 4 | 7292 | 1q25 |
| SLC37A3 | solute carrier family 37, member 3 | 84255 | 7q34 |

TABLE 1G (Good/Favorable Outcome)

| Symbol | | GeneID | Location |
|---|---|---|---|
| AGAP1 | ArfGAP with GTPase domain, ankyrin repeat and PH domain 1 (aka CENTG2) | 116987 | 2q37 |
| PTPRM | protein tyrosine phosphatase, receptor type, M | 5797 | 18p11 |
| STAP1 | signal transducing adaptor family member 1 | 26228 | 4q13 |
| CCNJ | cyclin J | 54619 | 10pter-q26 |
| PCDH17 | procadherin 17 | 27253 | 13q21 |
| MCAM | melanoma cell adhesion molecule | 4162 | 11q23 |
| CAPN3 | calpain 3 | 825 | 15q15-q21 |
| CABLES1 | Cdk5 and Abl enzyme substrate 1 | 91768 | 18q11 |
| GPR155 | G protein-coupled receptor 155 | 151556 | 2q31 |

DETAILED DESCRIPTION OF THE INVENTION

Gene expression profiling can provide insights into disease etiology and genetic progression, and can also provide tools for more comprehensive molecular diagnosis and therapeutic targeting. The biologic clusters and associated gene profiles identified herein may be useful for refined molecular classification of acute leukemias as well as improved risk assessment and classification, especially of high risk B precursor acute lymphoblastic leukemia (B-ALL), especially including pediatric B-ALL. In addition, the invention has identified numerous genes, including but not limited to the genes MUC4 (Mucin 4, cell surface associated), GRP110 (G protein-coupled receptor 110), IGJ (Immunoglobulin J polypeptide, linker protein for immunoglobulin alpha and mu polypeptides), CENTG2 (Centaurin, gamma 2), PTPRM (protein tyrosine phosphatase, receptor type, M), as well as numerous additional genes which are presented in Table 1P and 1G hereof, that are, alone or in combination, strongly predictive of therapeutic outcome in high risk B-ALL, and in particular high risk pediatric B precursor ALL. The genes identified herein, and the gene products from said genes, including proteins they encode, can be used to refine risk classification and diagnostics, to make outcome predictions and improve prognostics, and to serve as therapeutic targets in infant leukemia and pediatric ALL, especially B-precursor ALL.

"Gene expression" as the term is used herein refers to the production of a biological product encoded by a nucleic acid sequence, such as a gene sequence. This biological product, referred to herein as a "gene product," may be a nucleic acid or a polypeptide. The nucleic acid is typically an RNA molecule which is produced as a transcript from the gene sequence. The RNA molecule can be any type of RNA molecule, whether either before (e.g., precursor RNA) or after (e.g., mRNA) post-transcriptional processing. cDNA prepared from the mRNA of a sample is also considered a gene product. The polypeptide gene product is a peptide or protein that is encoded by the coding region of the gene, and is produced during the process of translation of the mRNA.

The term "gene expression level" refers to a measure of a gene product(s) of the gene and typically refers to the relative or absolute amount or activity of the gene product.

The term "gene expression profile" as used herein is defined as the expression level of two or more genes. The term gene includes all natural variants of the gene. Typically a gene expression profile includes expression levels for the products of multiple genes in given sample, up to about 13,000, preferably determined using an oligonucleotide microarray.

Unless otherwise specified, "a," "an," "the," and "at least one" are used interchangeably and mean one or more than one.

The term "patient" shall mean within context an animal, preferably a mammal, more preferably a human patient, more preferably a human child who is undergoing or will undergo therapy or treatment for leukemia, especially high risk B-precursor acute lymphoblastic leukemia.

The term "high risk B precursor acute lymphocytic leukemia" or "high risk B-ALL" refers to a disease state of a patient with acute lymphoblastic leukemia who meets certain high risk disease criteria. These include: confirmation of B-precursor ALL in the patient by central reference laboratories (See Borowitz, et al., *Rec Results Cancer Res* 1993; 131: 257-267); and exhibiting a leukemic cell DNA index of ≤0-1.16 (DNA content in leukemic cells: DNA content of normal $G_0/G_1$ cells) (DI) by central reference laboratory (See, Trueworthy, et al., *J Clin Oncol* 1992; 10: 606-613; and Pullen, et al., "Immunologic phenotypes and correlation with treatment results". In Murphy S B, Gilbert J R (eds). *Leukemia Research: Advances in Cell Biology and Treatment*. Elsevier: Amsterdam, 1994, pp 221-239) and at least one of the following: (1) WBC>10 000-99 000/µl, aged 1-2.99 years or ages 6-21 years; (2) WBC>100 000/µl, aged 1-21 years; (3) all patients with CNS or overt testicular disease at diagnosis; or (4) leukemic cell chromosome translocations t(1;19) or t(9;22) confirmed by central reference laboratory. (See, Crist, et al, *Blood* 1990; 76: 117-122; and Fletcher, et al., *Blood* 1991; 77: 435-439).

The term "traditional therapy" relates to therapy (protocol) which is typically used to treat leukemia, especially B-precursor ALL (including pediatric B-ALL) and can include Memorial Sloan-Kettering New York II therapy (NY II), UKALLR2, AL 841, AL851, ALHR88, MCP841 (India), as well as modified BFM (Berlin-Frankfurt-Münster) therapy, BMF-95 or other therapy, including ALinC 17 therapy as is well-known in the art. In the present invention the term "more aggressive therapy" or "alternative therapy" usually means a more aggressive version of conventional therapy typically used to treat leukemia, for example B-ALL, including pediatric B-precursor ALL, using for example, conventional or traditional chemotherapeutic agents at higher dosages and/or for longer periods of time in order to increase the likelihood of a favorable therapeutic outcome. It may also refer, in context, to experimental therapies for treating leukemia, rather than simply more aggressive versions of conventional (traditional) therapy.

Diagnosis, Prognosis and Risk Classification

Current parameters used for diagnosis, prognosis and risk classification in pediatric ALL are related to clinical data, cytogenetics and response to treatment. They include age and white blood count, cytogenetics, the presence or absence of minimal residual disease (MRD), and a morphological assessment of early response (measured as slow or rapid early therapeutic response). As noted above however, these parameters are not always well correlated with outcome, nor are they precisely predictive at diagnosis.

Prognosis is typically recognized as a forecast of the probable course and outcome of a disease. As such, it involves inputs of both statistical probability, requiring numbers of samples, and outcome data. In the present invention, outcome data is utilized in the form of continuous complete remission (CCR) of ALL or therapeutic failure (non-CCR). A patient population of hundreds is included, providing statistical power.

The ability to determine which cases of leukemia, especially high risk B precursor acute lymphoblastic leukemia (B-ALL), including high risk pediatric B-ALL will respond to treatment, and to which type of treatment, would be useful in appropriate allocation of treatment resources. It would also provide guidance as to the aggressiveness of therapy in producing a favorable outcome (continuous complete remission or CCR). As indicated above, the various standard therapies have significantly different risks and potential side effects, especially therapies which are more aggressive or even experimental in nature. Accurate prognosis would also minimize application of treatment regimens which have low likelihood of success and would allow a more efficient aggressive or even an experimental protocol to be used without wasting effort on therapies unlikely to produce a favorable therapeutic outcome, preferably a continuous complete remission. Such also could avoid delay of the application of alternative treatments which may have higher likelihoods of success for a particular presented case. Thus, the ability to evaluate individual leukemia cases, especially B-precursor acute lymphoblastic leukemia, for markers which subset into responsive and non-responsive groups for particular treatments is very useful.

Current models of leukemia classification have become better at distinguishing between cancers that have similar histopathological features but vary in clinical course and outcome, except in certain areas, one of them being in high risk B-precursor acute lymphoblastic leukemia (B-ALL). Identification of novel prognostic molecular markers is a priority if radical treatment is to be offered on a more selective basis to those high risk leukemia patients with disease states which do not respond favorably to conventional therapy. A novel strategy is described to discover/assess/measure molecular markers for B-ALL leukemia, especially high risk B-ALL to determine a treatment protocol, by assessing gene expression in leukemia patients and modeling these data based on a predetermined gene product expression for numerous patients having a known clinical outcome. The invention herein is directed to defining different forms of leukemia, in particular, B-precursor acute lymphoblastic leukemia, especially high risk B-precursor acute lymphoblastic leukemia, including high risk pediatric B-ALL by measuring expression gene products which can translate directly into therapeutic prognosis. Such prognosis allows for application of a treatment regimen having a greater statistical likelihood of cost effective treatments and minimization of negative side effects from the different/various treatment options.

In preferred aspects, the present invention provides an improved method for identifying and/or classifying acute leukemias, especially B precursor ALL, even more especially high risk B precursor ALL and also high risk pediatric B precursor ALL and for providing an indication of the therapeutic outcome of the patient based upon an assessment of expression levels of particular genes. Expression levels are determined for two or more genes associated with therapeutic outcome, risk assessment or classification, karyotpe (e.g., MLL translocation) or subtype (e.g., B-ALL, especially high risk B-ALL). Genes that are particularly relevant for diagnosis, prognosis and risk classification, especially for high risk B precursor ALL, including high risk pediatric B precursor ALL, according to the invention include those described in the tables (especially Table 1P and 1G) and figures herein. The gene expression levels for the gene(s) of interest in a biological sample from a patient diagnosed with or suspected of having an acute leukemia, especially B precursor ALL are compared to gene expression levels observed for a control sample, or with a predetermined gene expression level. Observed expression levels that are higher or lower than the expression levels observed for the gene(s) of interest in the control sample or that are higher or lower than the predetermined expression levels for the gene(s) of interest (as set forth in Table 1P and 1G) provide information about the acute leukemia that facilitates diagnosis, prognosis, and/or risk classification and can aid in treatment decisions, especially whether to use a more of less aggressive therapeutic regimen or perhaps even an experimental therapy. When the expression levels of multiple genes are assessed for a single biological sample, a gene expression profile is produced.

In one aspect, the invention provides genes and gene expression profiles that are correlated with outcome (i.e., complete continuous remission or good/favorable prognosis vs. therapeutic failure or poor/unfavorable prognosis) in high risk B-ALL. Assessment of at least two or more of these genes according to the invention, preferably at least three, at least four, at least five, six, seven, eight, nine, ten, eleven, twelve, thirteen, fourteen, fifteen, sixteen, seventeen, eighteen, nineteen, twenty, twenty-one, twenty-two, twenty-three, twenty-four or more as set forth in Tables 1P and 1F in a given gene profile can be integrated into revised risk classification schemes, therapeutic targeting and clinical trial design. In one embodiment, the expression levels of a particular gene (gene products) are measured, and that measurement is used, either alone or with other parameters, to assign the patient to a particular risk category (e.g., high risk B-ALL good/favorable or high risk B-ALL poor/unfavorable). The invention identifies several genes whose expression levels, either alone or in combination, are associated with outcome, including but not limited to at least two genes, preferably at least three genes, four genes and preferably all five genes genes selected from the group consisting of MUC4, GPR110, IGJ, CENTG2 and PTPRM.

The prognostic genes for purposes of the present invention are selected from the group consisting of MUC4 (mucin 4); GPR110 (G protein-coupled receptor 110); IGJ (immunoglobulin J polypeptide); NRXN3 (neurexin 3); CD99 (CD99 molecule); CRLF2 (cytokine receptor-like factor 2); ENAM (enamelin); TP53INP1 (tumor protein p53 inducible nuclear protein 1); IFITM1 (interferon induced transmembrane protein 1); IFITM2 (interferon induced transmembrane protein 2); IFITM3 (interferon induced transmembrane protein 3); TTYH2 (tweety homolog 2); SEMA6A (semaphorin 6A); TNFSF4 (tumor necrosis factor superfamily, member 4); SLC37A3 (solute carrier family 37, member 3) which are poor outcome predictors and AGAP1 (ArfGAP with GTPase domain, ankyrin repeat and PH domain 1, aka CENTG2); PTPRM (protein tyrosine phosphatase, receptor type, M); STAP1 (signal transducing adaptor family member 1); CCNJ (cyclin J); PCDH17 (procadherin 17); MCAM (melanoma cell adhesion molecule); CAPN3 (calpain 3); CABLES1 (Cdk5 and Abl enzyme substrate 1); and GPR155 (G protein-coupled receptor 155) which are favorable/good outcome predictors.

Some of these genes (e.g., those genes which are set forth in Table 1G) exhibit a positive association between expression level and outcome. For these genes, expression levels above a predetermined threshold level (or higher than that exhibited by a control sample) is predictive of a positive outcome (continuous complete remission). Our data suggests that direct measurement of the expression level of at two or more of these genes, preferably at least including CENTG2 and PTPRM, more preferably at least three of those genes, at least four, at least five, at least six, at least seven, at least eight and all nine of these genes more preferably all nine of these genes, can be used in refining risk classification and outcome prediction in high risk B precursor ALL. In particular, it is expected such measurements can be used to refine risk classification in children who are otherwise classified as having high risk B-ALL, but who can respond favorably (cured) with traditional, less intrusive therapies.

MUC4, GPR110, IGJ, in particular, are strong predictors of an unfavorable outcome for a high risk B-ALL patient and therefore in preferred aspects, the expression of at least three genes, and preferably the expression of at least two of those three genes among the fifteen (genes) which are set forth in Table 1P: (MUC4 (mucin 4); GPR110 (G protein-coupled receptor 110); IGJ (immunoglobulin J polypeptide); NRXN3 (neurexin 3); CD99 (CD99 molecule); CRLF2 (cytokine receptor-like factor 2); ENAM (enamelin); TP53INP1 (tumor protein p53 inducible nuclear protein 1); IFITM1 (interferon induced transmembrane protein 1); IFITM2 (interferon induced transmembrane protein 2); IFITM3 (interferon induced transmembrane protein 3); TTYH2 (tweety homolog 2); SEMA6A (semaphorin 6A); TNFSF4 (tumor necrosis factor superfamily, member 4); and SLC37A3 (solute carrier family 37, member 3) are measured and compared with predetermined values for each of the gene products measured. Any number of genes may be measured, with at least two genes being measured in the 15 genes listed. In preferred aspects, the expression of all fifteen genes is measured. Expression levels for multiple genes can be measured. For example, if normalized expression levels for (MUC4 (mucin 4); GPR110 (G protein-coupled receptor 110); IGJ (immunoglobulin J polypeptide); NRXN3 (neurexin 3); CD99 (CD99 molecule); CRLF2 (cytokine receptor-like factor 2); ENAM (enamelin); TP53INP1 (tumor protein p53 inducible nuclear protein 1); IFITM1 (interferon induced transmembrane protein 1); IFITM2 (interferon induced transmembrane protein 2); IFITM3 (interferon induced transmembrane protein 3); TTYH2 (tweety homolog 2); SEMA6A (semaphorin 6A); TNFSF4 (tumor necrosis factor superfamily, member 4); and SLC37A3 (solute carrier family 37, member 3) are higher than a predetermined value (higher expression levels of these genes are predictive of therapeutic failure), an unfavorable outcome can be predicted with greater certainty. In the case of the genes which are listed in Table 1G, which are genes predicting a favorable therapeutic outcome, if expression levels of at least two of AGAP1 (ArfGAP with GTPase domain, ankyrin repeat and PH domain 1, aka CENTG2); PTPRM (protein tyrosine phosphatase, receptor type, M); STAP1 (signal transducing adaptor family member 1); CCNJ (cyclin J); PCDH17 (procadherin 17); MCAM (melanoma cell adhesion molecule); CAPN3 (calpain 3); CABLES1 (Cdk5 and Abl enzyme substrate 1); and GPR155 (G protein-coupled receptor 155) are higher than a predetermined value, a more favorable outcome may be predicted. Preferably, at least two of MUC4, GPR110 and IGJ are measured and alternatively, both CENTG2 and PTPRM are measured and compared to predetermined values. Preferably, at least three of these gene produces are measured and compared to predetermined values.

In general, the expression of at least two genes in a single group is measured and compared to a predetermined value to provide a therapeutic outcome prediction and in addition to those two genes, the expression of any number of additional genes described in Tables 1P and 1G can be measured and used for predicting therapeutic outcome. In certain aspects of the invention where very high reliability is desired/required, the expression levels of all 24 genes (as per Tables 1P and 1F) may be measured and compared with a predetermined value for each of the genes measured such that a measurement above or below the predetermined value of expression for each of the group of genes is indicative of a favorable therapeutic outcome (continuous complete remission) or a therapeutic failure. In the event of a predictive favorable therapeutic outcome, conventional anti-cancer therapy may be used and in the event of a predictive unfavorable outcome (failure), more aggressive therapy may be recommended and implemented.

The expression levels of multiple (two or more, preferably three or more, more preferably at least five genes as described hereinabove and in addition to the five, up to twenty-four genes within the genes listed in Tables 1P and 1F in one or more lists of genes associated with outcome can be measured, and those measurements are used, either alone or with other parameters, to assign the patient to a particular risk category as it relates to a predicted therapeutic outcome. For example, gene expression levels of multiple genes can be measured for a patient (as by evaluating gene expression using an Affymetrix microarray chip) and compared to a list of genes whose expression levels (high or low) are associated with a positive (or negative) outcome. If the gene expression profile of the patient is similar to that of the list of genes associated with outcome, then the patient can be assigned to a low risk (favorable outcome) or high risk (unfavorable outcome) category. The correlation between gene expression profiles and class distinction can be determined using a variety of methods. Methods of defining classes and classifying samples are described, for example, in Golub et al, U.S. Patent Application Publication No. 2003/0017481 published Jan. 23, 2003, and Golub et al., U.S. Patent Application Publication No. 2003/0134300, published Jul. 17, 2003. The information provided by the present invention, alone or in conjunction with other test results, aids in sample classification and diagnosis of disease.

Computational analysis using the gene lists and other data, such as measures of statistical significance, as described herein is readily performed on a computer. The invention should therefore be understood to encompass machine readable media comprising any of the data, including gene lists, described herein. The invention further includes an apparatus that includes a computer comprising such data and an output device such as a monitor or printer for evaluating the results of computational analysis performed using such data.

In another aspect, the invention provides genes and gene expression profiles that are correlated with cytogenetics. This allows discrimination among the various karyotypes, such as MLL translocations or numerical imbalances such as hyperdiploidy or hypodiploidy, which are useful in risk assessment and outcome prediction.

In yet another aspect, the invention provides genes and gene expression profiles that are correlated with intrinsic disease biology and/or etiology. In other words, gene expression profiles that are common or shared among individual leukemia cases in different patients can be used to define intrinsically related groups (often referred to as clusters) of acute leukemia that cannot be appreciated or diagnosed using standard means such as morphology, immunophenotype, or cytogenetics. Mathematical modeling of the very sharp peak in ALL incidence seen in children 2-3 years old (>80 cases per million) has suggested that ALL may arise from two primary events, the first of which occurs in utero and the second after birth (Linet et al., Descriptive epidemiology of the leukemias, in Leukemias, $5^{th}$ Edition. ES Henderson et al. (eds). WB Saunders, Philadelphia. 1990). Interestingly, the detection of certain ALL-associated genetic abnormalities in cord blood samples taken at birth from children who are ultimately affected by disease supports this hypothesis (Gale et al., Proc. Natl. Acad. Sci. U.S.A., 94:13950-13954, 1997; Ford et al., Proc. Natl. Acad. Sci. U.S.A., 95:4584-4588, 1998).

The results for pediatric B precursor ALL suggest that this disease is composed of novel intrinsic biologic clusters defined by shared gene expression profiles, and that these intrinsic subsets cannot reliably be defined or predicted by traditional labels currently used for risk classification or by the presence or absence of specific cytogenetic abnormalities. We have identified 24 genes for determining outcome in high risk B-ALL, and in particular high risk pediatric B precursor ALL using the methods set forth hereinbelow, for identifying candidate genes associated with classification and outcome. We have identified 9 genes (Table 1G) which are positive predictors of favorable outcome in high risk B precursor ALL patients, especially high risk pediatric B precursor ALL patients. Expression of two or more of these genes which is greater than a predetermined value or from a control is indicative that traditional B-ALL therapy is appropriate for treating the patient's B precursor ALL. In addition, the present invention has identified fifteen (15) genes (see Table 1P) which correlate with failed therapy. Thus, a measurement of the expression of these fifteen genes which is higher than predetermined values for each of these genes is predictive of a high likelihood of a therapeutic failure using traditional B precursor ALL therapies. High expression for these fifteen genes would dictate an early aggressive therapy or experimental therapy in order to increase the likelihood of a favorable therapeutic outcome.

Some genes in these clusters are metabolically related, suggesting that a metabolic pathway that is associated with cancer initiation or progression. Other genes in these metabolic pathways, like the genes described herein but upstream or downstream from them in the metabolic pathway, thus can also serve as therapeutic targets.

In yet another aspect, the invention provides genes and gene expression profiles which may be used to discriminate high risk B-ALL from acute myeloid leukemia (AML) in infant leukemias by measuring the expression levels of the gene product(s) correlated with B-ALL as otherwise described herein, especially B-precursor ALL.

It should be appreciated that while the present invention is described primarily in terms of human disease, it is useful for diagnostic and prognostic applications in other mammals as well, particularly in veterinary applications such as those related to the treatment of acute leukemia in cats, dogs, cows, pigs, horses and rabbits.

Further, the invention provides methods for computational and statistical methods for identifying genes, lists of genes and gene expression profiles associated with outcome, karyotype, disease subtype and the like as described herein.

In sum, the present invention has identified a group of genes which strongly correlate with favorable/unfavorable outcome in B precursor acute lymphoblastic leukemia and contribute unique information to allow the reliable prediction of a therapeutic outcome in high risk B precursor ALL, especially high risk pediatric B precursor ALL.

Measurement of Gene Expression Levels

Gene expression levels are determined by measuring the amount or activity of a desired gene product (i.e., an RNA or a polypeptide encoded by the coding sequence of the gene) in a biological sample. Any biological sample can be analyzed. Preferably the biological sample is a bodily tissue or fluid, more preferably it is a bodily fluid such as blood, serum, plasma, urine, bone marrow, lymphatic fluid, and CNS or spinal fluid. Preferably, samples containing mononuclear bloods cells and/or bone marrow fluids and tissues are used. In embodiments of the method of the invention practiced in cell culture (such as methods for screening compounds to identify therapeutic agents), the biological sample can be whole or lysed cells from the cell culture or the cell supernatant.

Gene expression levels can be assayed qualitatively or quantitatively. The level of a gene product is measured or estimated in a sample either directly (e.g., by determining or estimating absolute level of the gene product) or relatively (e.g., by comparing the observed expression level to a gene expression level of another samples or set of samples). Measurements of gene expression levels may, but need not, include a normalization process.

Typically, mRNA levels (or cDNA prepared from such mRNA) are assayed to determine gene expression levels. Methods to detect gene expression levels include Northern blot analysis (e.g., Harada et al., Cell 63:303-312 (1990)), S1 nuclease mapping (e.g., Fujita et al., Cell 49:357-367 (1987)), polymerase chain reaction (PCR), reverse transcription in combination with the polymerase chain reaction (RT-PCR) (e.g., Example III; see also Makino et al., Technique 2:295-301 (1990)), and reverse transcription in combination with the ligase chain reaction (RT-LCR). Multiplexed methods that allow the measurement of expression levels for many genes simultaneously are preferred, particularly in embodiments involving methods based on gene expression profiles comprising multiple genes. In a preferred embodiment, gene expression is measured using an oligonucleotide microarray, such as a DNA microchip. DNA microchips contain oligonucleotide probes affixed to a solid substrate, and are useful for screening a large number of samples for gene expression. DNA microchips comprising DNA probes for binding polynucleotide gene products (mRNA) of the various genes from Table 1 are additional aspects of the present invention.

Alternatively or in addition, polypeptide levels can be assayed. Immunological techniques that involve antibody binding, such as enzyme linked immunosorbent assay (ELISA) and radioimmunoassay (RIA), are typically employed. Where activity assays are available, the activity of a polypeptide of interest can be assayed directly.

As discussed above, the expression levels of these markers in a biological sample may be evaluated by many methods. They may be evaluated for RNA expression levels. Hybridization methods are typically used, and may take the form of a PCR or related amplification method. Alternatively, a number of qualitative or quantitative hybridization methods may be used, typically with some standard of comparison, e.g., actin message. Alternatively, measurement of protein levels may performed by many means. Typically, antibody based methods are used, e.g., ELISA, radioimmunoassay, etc., which may not require isolation of the specific marker from other proteins. Other means for evaluation of expression levels may be applied. Antibody purification may be performed, though separation of protein from others, and evaluation of specific bands or peaks on protein separation may provide the same results. Thus, e.g., mass spectroscopy of a protein sample may indicate that quantitation of a particular peak will allow detection of the corresponding gene product. Multidimensional protein separations may provide for quantitation of specific purified entities.

The observed expression levels for the gene(s) of interest are evaluated to determine whether they provide diagnostic or prognostic information for the leukemia being analyzed. The evaluation typically involves a comparison between observed gene expression levels and either a predetermined gene expression level or threshold value, or a gene expression level that characterizes a control sample ("predetermined value"). The control sample can be a sample obtained from a normal (i.e., non-leukemic) patient(s) or it can be a sample obtained from a patient or patients with high risk B-ALL that has been cured. For example, if a cytogenic classification is desired, the biological sample can be interrogated for the expression level of a gene correlated with the cytogenic abnormality, then compared with the expression level of the same gene in a patient known to have the cytogenetic abnormality (or an average expression level for the gene that characterizes that population).

The present study provides specific identification of multiple genes whose expression levels in biological samples will serve as markers to evaluate leukemia cases, especially therapeutic outcome in high risk B-ALL cases, especially high risk pediatric B-ALL cases. These markers have been selected for statistical correlation to disease outcome data on a large number of leukemia (high risk B-ALL) patients as described herein.

Treatment of Infant Leukemia and Pediatric B-Precursor ALL

The genes identified herein that are associated with outcome of a disease state may provide insight into a treatment regimen. That regimen may be that traditionally used for the treatment of leukemia (as discussed hereinabove) in the case where the analysis of gene products from samples taken from the patient predicts a favorable therapeutic outcome, or alternatively, the chosen regimen may be a more aggressive approach (e.g., higher dosages of traditional therapies for longer periods of time) or even experimental therapies in instances where the predictive outcome is that of failure of therapy.

In addition, the present invention may provide new treatment methods, agents and regimens for the treatment of leukemia, especially high risk B-precursor acute lymphoblastic leukemia, especially high risk pediatric B-precursor ALL. The genes identified herein that are associated with outcome and/or specific disease subtypes or karyotypes are likely to have a specific role in the disease condition, and hence represent novel therapeutic targets. Thus, another aspect of the invention involves treating high risk B-ALL patients, including high risk pediatric ALL patients by modulating the expression of one or more genes described herein in Table 1P or 1F to a desired expression level or below.

In the case of those gene products (Table 1P and 1F) whose increased or decreased expression (whether above or below a predetermined value, for example obtained for a control sample) is associated with a favorable outcome or failure, the treatment method of the invention will involve enhancing the expression of those gene products in which a favorable therapeutic outcome is predicted by such enhancement and inhibiting the expression of those gene products in which enhanced expression is associated with failed therapy.

Thus, in the case of CENTG2, PTPRM or other gene products of Table 1G such as STAP1; CCNJ; PCDH17; MCAM; CAPN3; CABLES1; and GPR155, increased expression of at least two, at least three, at least four, at least five and preferably all of these genes will be a therapeutic goal because enhanced expression of these genes together is predictive of a favorable therapeutic outcome and in the case of MUC4; GPR110; IGJ; NRXN3; CD99; CRLF2; ENAM; TP53INP1; IFITM1; IFITM2; IFITM3; TTYH2; SEMA6A; TNFSF4; and SLC37A3, decreased expression is the goal as high expression of genes, especially at least MUC4 and GPR110 or MUC4, GPR110 and IGJ is a predictor of therapeutic failure. The same is true for the expression products of the other genes in the list which are found in Table 1—those which exhibit a favorable therapeutic outcome for high expression will be enhanced as a therapeutic goal, whereas as those which exhibit a failed therapeutic outcome for high expression will be inhibited as a therapeutic goal.

Thus, in the case of the 24 genes from Table 1P and 1F, the increased or decreased expression levels for a particular gene as indicated in the table becomes a therapeutic goal in the treatment of leukemia, especially high risk B-precursor ALL (especially pediatric B-precursor ALL). Therapeutic agents for effecting the increased or decreased expression levels may be identified and used as alternative therapies to traditional treatment modalities for leukemia, especially high risk B-precursor ALL and either the increased or decreased expression of each of these genes will become a therapeutic goal for the treatment of cancer or the development of agents for the treatment of cancer. Thus, in this aspect of the present invention, especially in high risk B precursor ALL (pediatric), the treatment method of the invention involves enhancing or inhibiting at least one of the gene product of expression as such gene expression is described in Table 1P and/or 1F with a therapeutic outcome. In preferred aspects, the therapeutic method preferably enhances expression at least one of the genes in Table 1G (preferably CENTG2 and/or PTPRM) or alternatively inhibits the expression of one of the genes in table 1P (preferably at least one of MUC4, GPR110 and/or IGJ) in order to promote a more favorable therapeutic outcome. In addition to these five genes, expression of at least one additional gene and preferably as many as 19 additional genes (totally 24 genes) from the list in Tables 1F and/or 1P (high expression CCR or favorable outcome is desirable, low expression of failure is desirable) can be influenced to provide alternative therapies and anti-cancer agents.

For a number (nine) of the gene products identified herein, as set forth in Table 1G above, increased expression is correlated with positive outcomes in leukemia patients. Thus, the invention includes a method for treating leukemia, such as high risk B-ALL including high risk pediatric B-ALL that involves administering to a patient a therapeutic agent that causes an increase in the amount or activity of at least one of CENTG2, PTPRM and/or other polypeptides of interest where high expression has been identified herein to be positively correlated with favorable outcome (CCR, see Table 1G). Preferably the increase in amount or activity of the selected gene product is at least about 10%, preferably 25%, most preferably 100% above the expression level observed in the patient prior to treatment.

The therapeutic agent can be a polypeptide having the biological activity of the polypeptide of interest (e.g., CENTG2, PTPRM or other gene product) or a biologically active subunit or analog thereof. Alternatively, the therapeutic agent can be a ligand (e.g., a small non-peptide molecule, a peptide, a peptidomimetic compound, an antibody, or the like) that agonizes (i.e., increases) the activity of the polypeptide of interest. For example, in the case of CENTG2, PTPRM or other gene product, these gene products may be administered to the patient to enhance the activity and treat the patient.

Gene therapies can also be used to increase the amount of a polypeptide of interest in a host cell of a patient. Polynucleotides operably encoding the polypeptide of interest can be delivered to a patient either as "naked DNA" or as part of an expression vector. The term vector includes, but is not limited to, plasmid vectors, cosmid vectors, artificial chromosome vectors, or, in some aspects of the invention, viral vectors. Examples of viral vectors include adenovirus, herpes simplex virus (HSV), alphavirus, simian virus 40, picornavirus, vaccinia virus, retrovirus, lentivirus, and adeno-associated virus. Preferably the vector is a plasmid. In some aspects of the invention, a vector is capable of replication in the cell to which it is introduced; in other aspects the vector is not capable of replication. In some preferred aspects of the present invention, the vector is unable to mediate the integration of the vector sequences into the genomic DNA of a cell. An example of a vector that can mediate the integration of the vector sequences into the genomic DNA of a cell is a retroviral vector, in which the integrase mediates integration of the retroviral vector sequences. A vector may also contain transposon sequences that facilitate integration of the coding region into the genomic DNA of a host cell.

Selection of a vector depends upon a variety of desired characteristics in the resulting construct, such as a selection marker, vector replication rate, and the like. An expression vector optionally includes expression control sequences operably linked to the coding sequence such that the coding region is expressed in the cell. The invention is not limited by the use of any particular promoter, and a wide variety is known. Promoters act as regulatory signals that bind RNA polymerase in a cell to initiate transcription of a downstream (3' direction) operably linked coding sequence. The promoter used in the invention can be a constitutive or an inducible promoter. It can be, but need not be, heterologous with respect to the cell to which it is introduced.

Another option for increasing the expression of a gene like CENTG2, PTPRM or one or more gene products as described in Table 1G (CENTG2; PTPRM; STAP1; CCNJ; PCDH17; MCAM; CAPN3; CABLES1; and/or GPR155) wherein higher expression levels are predictive for favorable outcome is to reduce the amount of methylation of the gene. Demethylation agents, therefore, may be used to re-activate the expression of one or more of the gene products in cases where methylation of the gene is responsible for reduced gene expression in the patient.

For other genes identified herein as being correlated with therapeutic failure or without outcome in high risk B-ALL, such as high risk pediatric B-ALL, high expression of the gene is associated with a negative outcome rather than a positive outcome. In the present invention, these genes/gene products (see Table 1P) are selected from the group consisting of MUC4; GPR110; IGJ; NRXN3; CD99; CRLF2; ENAM; TP53INP1; IFITM1; IFITM2; IFITM3; TTYH2; SEMA6A; TNFSF4; and SLC37A3 at least two genes/gene products from this list (especially including MUC4 and GPR110 or MUC4, GPR110 and/or IGJ), preferably at least three gene, at least 4 from this list, at least 5 from this list, at least 6 from this list, at least 7 from this list, at least 8, at least 9 at least 10, at least 11, at least 12, at least 13, at least 14 and all 15 genes/gene products from this list. In such instances, where the expression levels of these genes as described are high, the predicted therapeutic outcome in such patients is therapeutic failure for traditional therapies. In such case, more aggressive approaches to traditional therapies and/or experimental therapies may be attempted.

The eight genes described above (negative outcome) accordingly represent novel therapeutic targets, and the invention provides a therapeutic method for reducing (inhibiting) the amount and/or activity of these polypeptides of interest in a leukemia patient. Preferably the amount or activity of the selected gene product is reduced to less than about 90%, more preferably less than about 75%, most preferably less than about 25% of the gene expression level observed in the patient prior to treatment.

A cell manufactures proteins by first transcribing the DNA of a gene for that protein to produce RNA (transcription). In eukaryotes, this transcript is an unprocessed RNA called precursor RNA that is subsequently processed (e.g. by the removal of introns, splicing, and the like) into messenger RNA (mRNA) and finally translated by ribosomes into the desired protein. This process may be interfered with or inhibited at any point, for example, during transcription, during RNA processing, or during translation. Reduced expression of the gene(s) leads to a decrease or reduction in the activity of the gene product and, in cases where high expression leads to a therapeutic failure, an expected therapeutic success.

The therapeutic method for inhibiting the activity of a gene whose high expression (table 1) is correlated with negative outcome/therapeutic failure involves the administration of a therapeutic agent to the patient to inhibit the expression of the gene. The therapeutic agent can be a nucleic acid, such as an antisense RNA or DNA, or a catalytic nucleic acid such as a ribozyme, that reduces activity of the gene product of interest by directly binding to a portion of the gene encoding the enzyme (for example, at the coding region, at a regulatory element, or the like) or an RNA transcript of the gene (for example, a precursor RNA or mRNA, at the coding region or at 5' or 3' untranslated regions) (see, e.g., Golub et al., U.S. Patent Application Publication No. 2003/0134300, published Jul. 17, 2003). Alternatively, the nucleic acid therapeutic agent can encode a transcript that binds to an endogenous RNA or DNA; or encode an inhibitor of the activity of the polypeptide of interest. It is sufficient that the introduction of the nucleic acid into the cell of the patient is or can be accompanied by a reduction in the amount and/or the activity of the polypeptide of interest. An RNA captamer can also be used to inhibit gene expression. The therapeutic agent may also be protein inhibitor or antagonist, such as small non-peptide molecule such as a drug or a prodrug, a peptide, a peptidomimetic compound, an antibody, a protein or fusion protein, or the like that acts directly on the polypeptide of interest to reduce its activity.

The invention includes a pharmaceutical composition that includes an effective amount of a therapeutic agent as described herein as well as a pharmaceutically acceptable carrier. These therapeutic agents may be agents or inhibitors of selected genes (table 1). Therapeutic agents can be administered in any convenient manner including parenteral, subcutaneous, intravenous, intramuscular, intraperitoneal, intranasal, inhalation, transdermal, oral or buccal routes. The dosage administered will be dependent upon the nature of the agent; the age, health, and weight of the recipient; the kind of concurrent treatment, if any; frequency of treatment; and the effect desired. A therapeutic agent identified herein can be administered in combination with any other therapeutic agent(s) such as immunosuppressives, cytotoxic factors and/or cytokine to augment therapy, see Golub et al, Golub et al., U.S. Patent Application Publication No. 2003/0134300, published Jul. 17, 2003, for examples of suitable pharmaceutical formulations and methods, suitable dosages, treatment combinations and representative delivery vehicles.

The effect of a treatment regimen on an acute leukemia patient can be assessed by evaluating, before, during and/or after the treatment, the expression level of one or more genes as described herein. Preferably, the expression level of gene(s) associated with outcome, such as a gene as described above (preferably, favorable outcome Table 1G, but also, negative outcome as in Table 1P), may be monitored over the course of the treatment period. Optionally gene expression profiles showing the expression levels of multiple selected genes associated with outcome can be produced at different times during the course of treatment and compared to each other and/or to an expression profile correlated with outcome.

Screening for Therapeutic Agents

The invention further provides methods for screening to identify agents that modulate expression levels of the genes identified herein that are correlated with outcome, risk assessment or classification, cytogenetics or the like. Candidate compounds can be identified by screening chemical libraries according to methods well known to the art of drug discovery and development (see Golub et al., U.S. Patent Application Publication No. 2003/0134300, published Jul. 17, 2003, for a detailed description of a wide variety of screening methods). The screening method of the invention is preferably carried out in cell culture, for example using leukemic cell lines (especially B-precursor ALL cell lines) that express known levels of the therapeutic target, such as CENT2G, PTPRM or other gene product as otherwise described herein (see Table 1G and 1P). The cells are contacted with the candidate compound and changes in gene expression of one or more genes relative to a control culture or predetermined values based upon a control culture are measured. Alternatively, gene expression levels before and after contact with the candidate compound can be measured. Changes in gene expression (above or below a predetermined value) indicate that the compound may have therapeutic utility. Structural libraries can be surveyed computationally after identification of a lead drug to achieve rational drug design of even more effective compounds.

The invention further relates to compounds thus identified according to the screening methods of the invention. Such compounds can be used to treat high risk B-ALL especially include high risk pediatric B-ALL as appropriate, and can be formulated for therapeutic use as described above.

Active analogs, as that term is used herein, include modified polypeptides. Modifications of polypeptides of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like.

In certain aspects of the present invention, a therapeutic method may rely on an antibody to one or more gene products predictive of outcome, preferably to one or more gene product which otherwise is predictive of a negative outcome, so that the antibody may function as an inhibitor of a gene product. Preferably the antibody is a human or humanized antibody, especially if it is to be used for therapeutic purposes. A human antibody is an antibody having the amino acid sequence of a human immunoglobulin and include antibodies produced by human B cells, or isolated from human sera, human immunoglobulin libraries or from animals transgenic for one or more human immunoglobulins and that do not express endogenous immunoglobulins, as described in U.S. Pat. No. 5,939,598 by Kucherlapati et al., for example. Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. U.S.A., 90:2551-2555 (1993); Jakobovits et al., Nature, 362:255-258 (1993); Bruggemann et al., Year in Immuno., 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985); Boerner et al., J. Immunol., 147(1):86-95 (1991)).

Antibodies generated in non-human species can be "humanized" for administration in humans in order to reduce their antigenicity. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Residues from a complementary determining region (CDR) of a human recipient antibody are replaced by hydroxylation, methylation, amidation, and the attachment of carbohydrate or lipid moieties, cofactors, and the like.

In certain aspects of the present invention, a therapeutic method may rely on an antibody to one or more gene products predictive of outcome, preferably to one or more gene product which otherwise is predictive of a negative outcome, so that the antibody may function as an inhibitor of a gene product.

Preferably the antibody is a human or humanized antibody, especially if it is to be used for therapeutic purposes. A human antibody is an antibody having the amino acid sequence of a human immunoglobulin and include antibodies produced by human B cells, or isolated from human sera, human immunoglobulin libraries or from animals transgenic for one or more human immunoglobulins and that do not express endogenous immunoglobulins, as described in U.S. Pat. No. 5,939,598 by Kucherlapati et al., for example. Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. U.S.A., 90:2551-2555 (1993); Jakobovits et al., Nature, 362:255-258 (1993); Bruggemann et al., Year in Immuno., 7:33 (1993)). Human antibodies can also be produced in phage display libraries (Hoogenboom et al., J. Mol. Biol., 227:381 (1991); Marks et al., J. Mol. Biol., 222: 581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985); Boerner et al., J. Immunol., 147(1):86-95 (1991)).

Antibodies generated in non-human species can be "humanized" for administration in humans in order to reduce their antigenicity. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Residues from a complementary determining region (CDR) of a human recipient antibody are replaced by residues from a CDR of a non-human species (donor antibody) such as mouse, rat or rabbit having the desired specificity. Optionally, Fv framework residues of the human immunoglobulin are replaced by corresponding non-human residues. See Jones et al., Nature, 321:522-525 (1986); Riechmann et al., Nature, 332:323-327 (1988); and Presta, Curr. Op. Struct. Biol., 2:593-596 (1992). Methods for humanizing non-human antibodies are well known in the art. See Jones et al., Nature, 321:522-525 (1986); Riechmann et al., Nature, 332:323-327 (1988); Verhoeyen et al., Science, 239:1534-1536 (1988); and (U.S. Pat. No. 4,816,567).

Laboratory Applications

The present invention further includes an exemplary microchip for use in clinical settings for detecting gene expression levels of one or more genes described herein as being associated with outcome, risk classification, cytogenics or subtype in high risk B-ALL, including high risk pediatric B-ALL. In a preferred embodiment, the microchip contains DNA probes specific for the target gene(s). Also provided by the invention is a kit that includes means for measuring expression levels for the polypeptide product(s) of one or more such genes, including any of the genes listed in Table 1G and 1F below, preferably one or more of (CENTG2); PTPRM; STAP1; CCNJ; PCDH17; MCAM; CAPN3; CABLES1; and GPR155 as positive outcome predictor genes/gene products or one or more of MUC4; GPR110; IGJ; NRXN3; CD99; CRLF2; ENAM; TP53INP1; IFITM1; IFITM2; IFITM3; TTYH2; SEMA6A; TNFSF4; and SLC37A3, as negative outcome predictors, preferably a combination of these genes/gene products. In certain preferred embodiments, the microchip contains DNA probes for all 24 genes which are set forth in Table 1P and 1F or any one of the two sets of gene products in Tables 1P or 1F, preferably at least two or more gene products described above for Table 1P or 1F alone with at least one additional gene taken from the other of Table 1P or 1F. Various probes can be provided onto the microchip representing any number and any variation of gene products as otherwise described in Table 1P or 1F. In a preferred embodiment, the kit is an immunoreagent kit and contains one or more antibodies specific for the polypeptide(s) of interest.

Relevant portion of the below cited references are referenced and incorporated herein. In addition, previously published WO 2004/053074 (Jun. 24, 2004) is incorporated by reference in its entirety herein.

In the present invention, sophisticated computational tools and statistical methods were used to reduce the comprehensive molecular profiles to a more limited set of 24 genes (a gene expression "classifier") that is highly predictive of overall outcome in high risk B-ALL, including high risk pediatric B-ALL.

As described in the following examples, the inventors examined pre-treatment specimens from 207 patients with high risk B-precursor acute lymphoblastic leukemia (ALL) who were uniformly treated on Children's Oncology Group Trial COG P9906. Gene expression profiles were correlated with clinical features, treatment responses, and relapse free survivals (RFS). The use of four different unsupervised clustering methods showed significant overlap in the classification of these patients. Two clusters contained all children with either t(1;19)(q23;p13) translocations or MLL rearrangements. The other six clusters were novel and not associated with recurrent chromosomal abnormalities or distinctive clinical features. One of these clusters (R6; n=21) had significantly better 4-year RFS of 95% as compared to the 4-year RFS of 61% for the entire cohort (P"0.002). A cluster of children (R8; n=24) with dismal outcomes was found with a 4 year RFS of only 21% (P<0.001). A significant proportion of these children (63%; 15/24) were of Hispanic/Latino ethnicity. Specific gene alterations in this unique subset of ALL provide the basis for up-front identification of these extremely high risk individuals and allow for the possibility of targeted therapy

EXAMPLES

Material and Methods
Patients

COG P9906 enrolled 272 eligible children and adolescents with higher risk ALL between Mar. 15, 2000 to Apr. 25, 2003. This trial targeted a subset of patients with NCI high risk clinical features[2] defined by a sliding age and white blood cell count criteria[8] that identified a group that experienced very poor outcomes (44% 4-year RFS) in prior Pediatric Oncology Group clinical trials. Patients were first enrolled on the COG P9000 classification study and received a 4-drug induction. Patients with 5-25% blasts in the bone marrow (BM) at day 29 of induction received 2 additional weeks of extended induction therapy using the same agents. Patients with less than 5% BM blasts following 4-6 weeks of induction therapy were eligible to participate in COG P9906 if they met the age/WBC criteria described previously or had overt central nervous system (CNS3) or testicular involvement. Patients with favorable (trisomy 4+10; TEL/AML1) or unfavorable (Philadelphia chromosome-positive or hypodiploid with less than 44 chromosomes) genetic features were excluded, with the exception that those with favorable genetic features and CNS3 status or testicular involvement were included.[9] Patients enrolled in COG P9906 were treated uniformly with an "augmented BFM" regimen that included two delayed intensification phases analogous to that described previously.[10,11]

All patients had minimal residual disease (MRD) testing performed by flow cytometry in a single central reference laboratory as described previously.[12] Testing was performed at day 8 on peripheral blood (PB), and at end induction and end of interim maintenance (week 22) on BM. Cases were defined as MRD positive or negative using a threshold of 0.01%. Outcome data for all patients were frozen as of October 2006. The median time to event or censoring was 3.7 years.

Expression data were obtained on 207 cryopreserved specimens with >80% leukemic blasts, stored in the COG leukemia repository (University of New Mexico) and selected solely on the basis of specimen availability. The clinical variables and outcome of the 207 patients studied were highly similar to those of the entire cohort of 272 eligible patients (Table 5S). The NCI and participating institutions approved the treatment protocol through their respective Institutional Review Boards (IRBs). All patients or their patients/guardians provided informed consent prior to trial enrollment.

Nucleic Acids and Microarrays

RNA was purified from cryopreserved samples by the Trizol method and was quantified by spectrophotometry. Generation of cDNA, cRNA and biotin-labeled probes was performed as previously described.[7] Samples were analyzed using the Human Genome U133 Plus 2.0 arrays (Affymetrix, Santa Clara, Calif.). Signal intensities and expression data were generated with the Affymetrix GCOS 1.4 software package. A mask to remove study-specific uninformative probe pairs was applied to all the arrays (details in Supplement). The default Affymetrix normalization (all genes; intensity of 500) was used. This gene expression dataset may be accessed via the National Cancer Institute caArray site (array.nci.nih.gov/caarray/) and at Gene Expression Omnibus (ncbi.nlm.nih.gov/geo/). A direct link to this dataset is provided for the reviewers at: ncbi.nlm.nih.gov/geo/query/acc.cgi?token=lrqbxguwqyqaapk&acc=GSE11877.

Unsupervised Clustering Methods

Microarray expression data were available from an initial 54,668 probe sets after masking removed seven probe sets (Table S1). Four complementary unsupervised clustering methods were used: traditional hierarchical clustering, VxInsight (VX)[13], and hierarchical clustering using outlier genes identified by Cancer Outlier Profile Analysis (COPA)[14] and Recognition of Outliers by Sampling Ends (ROSE). Descriptions of the details of each of these methods and their application to the data sets are supplied as supplementary information.

In an effort to simplify the nomenclature for the clusters the numbering from the hierarchical clustering groups was applied to the other methods. Each method cluster is prefixed by a letter indicating the method used to identify it (H=hierarchical clustering, V=VxInsight, C=COPA and R=ROSE). Clusters from each method were compared to those of the hierarchical clustering and then the group numbers were assigned based upon maximum similarity.

Generation of Gene Lists

Although the genes used for hierarchical clustering were sufficient for distinguishing the groups, they were far from comprehensive in characterizing them. Consequently, we used the group membership to reevaluate all 54,668 probes and sort them by their average rank order. This generates tables of the highest and lowest expressed probes across each group that are, presumably, reflective of their nature. Because these samples have so many probe sets with very low expression, this analysis was not informative at the low end of the rank order. At the high end, however, it worked quite well to identify genes for which each cluster had overexpression. These top 50 probe sets for all R-clusters are given in the Supplement. The creation of gene lists by VX has been described previously[13] and is also detailed in the Supplement.

Statistical Methods

Statistical analysis for each group was performed by comparing group membership to all samples not in that group. Log rank analysis was used to evaluate RFS.[15] Kaplan-Meier survival analysis and hazard ratios were also calculated for comparisons of group RFS.[16,17] Higher hazard ratios indicate that a group has poorer RFS relative to the remainder of the cohort while lower hazard ratios indicate the opposite. Events in all RFS analysis are relapses following remission. Two-sided Satterthwaite t-tests and Mann-Whitney rank sum tests were used to analyze intensities and age/WBC counts, respectively; Fisher's exact test was used to evaluate the binary variables.[16]

Results

Patient Cohort

To determine if we could identify novel clinically-relevant leukemic subgroups, gene expression profiles were obtained from a retrospective cohort of 207 previously untreated ALL patients who were enrolled on the COG P9906 higher risk ALL trial. The cohort had a slight male predominance (66%) with one-quarter of the children being of Hispanic/Latino ethnicity. At diagnosis, the median white blood cell count was elevated at 62,300/µL and high numbers of blasts were identified in the CNS in 10% (20/201 for which data were available) of children. Mixed lineage leukemia (MLL) or E2A/PBX1 translocations were present in 10% and 11% of cases, respectively. RFS and overall survival at 4 years were 61% and 83% respectively. Clinical details are shown in Table 5S.

Clustering Analysis

Figure 1B:
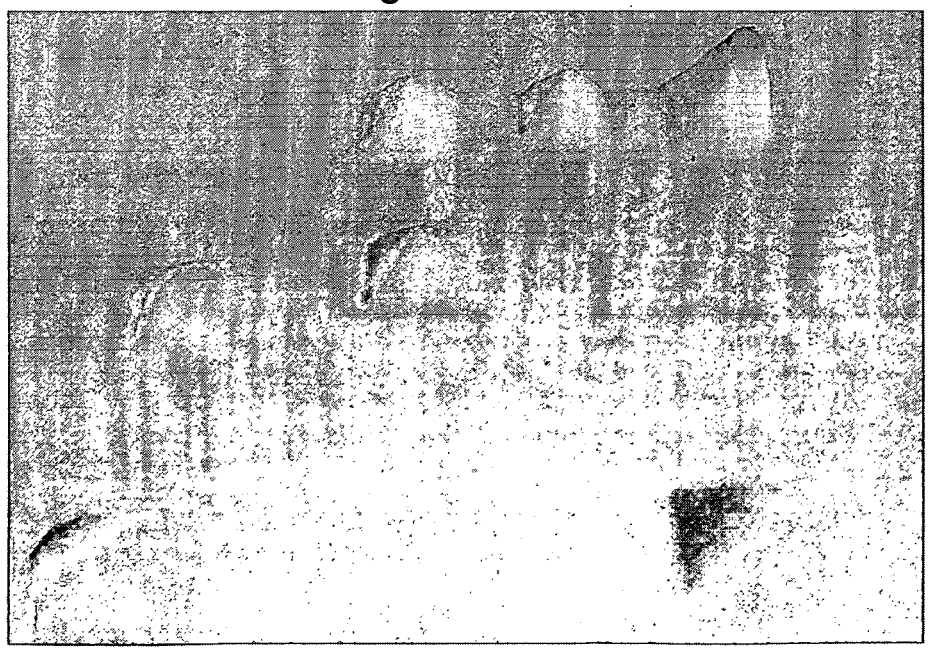

Multiple approaches were taken to identify highly-related groups of patients, under the assumption that the most robust clusters would be independently partitioned by more than one algorithm. Unsupervised two-dimensional hierarchical clustering based on the association of gene signatures identified 8 clusters (H1-8) (FIG. 1A). VxInsight identified 7 clusters (V1-7), as shown in FIG. 1B. The strong overlap between the clusters identified by these methods is also shown in FIG. 1B. The samples grouped in H1 were predominately found in V1. There was a similar overlap of H2 and H6 with V2 and V6, respectively. The samples identified as H8 in the hierarchical clustering were predominately found in V8, although some of these patients were also grouped into V4.

Figure 2B:
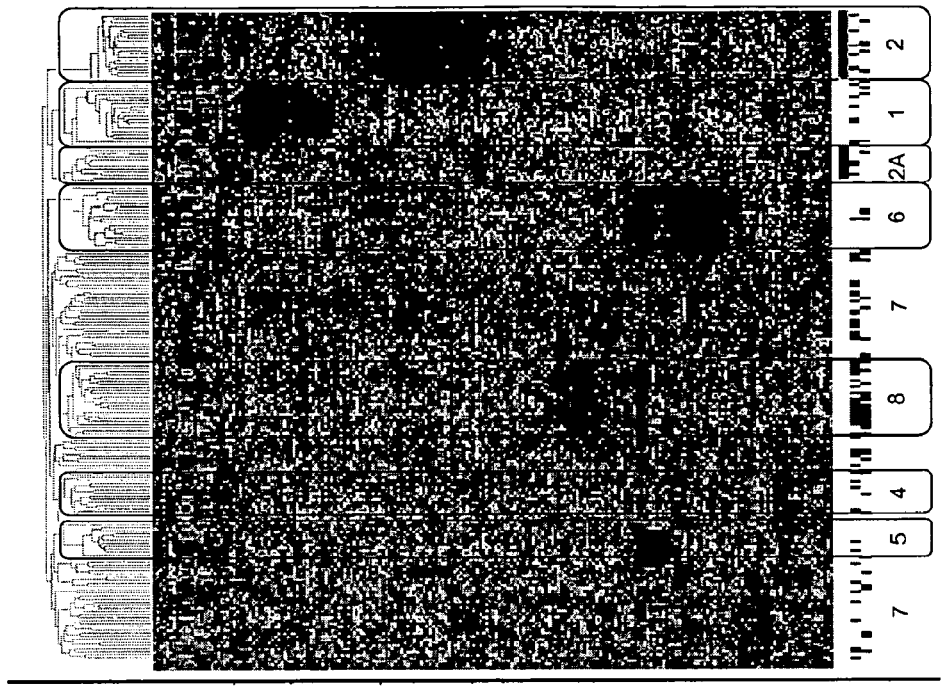
FIG. 2 shows the hierarchical heat map that identifies outlier clusters. In Panel A the 209 COPA probe sets are shown in rows and the 207 samples in columns. In Panel B the 215 ROSE probe sets are shown in rows. The colored boxes indicate the identification of significant clusters. The colored bars across the bottom denote translocations, outcome and race as described in FIG. 1. The similarities between the groups identified by the ROSE or COPA and hierarchical clustering are shown in FIG. 2C.
FIG. 2C shows a 3-D plot of cluster membership from different clustering methods. Each of the three clustering methods is shown on an axis: HC=hierarchical clusters, RC=ROSE/COPA clusters and Vx=VxInsight clusters. Cluster numbers are given across each axis with the exception of RC9, which represents cluster 2A.
Figure 2A:
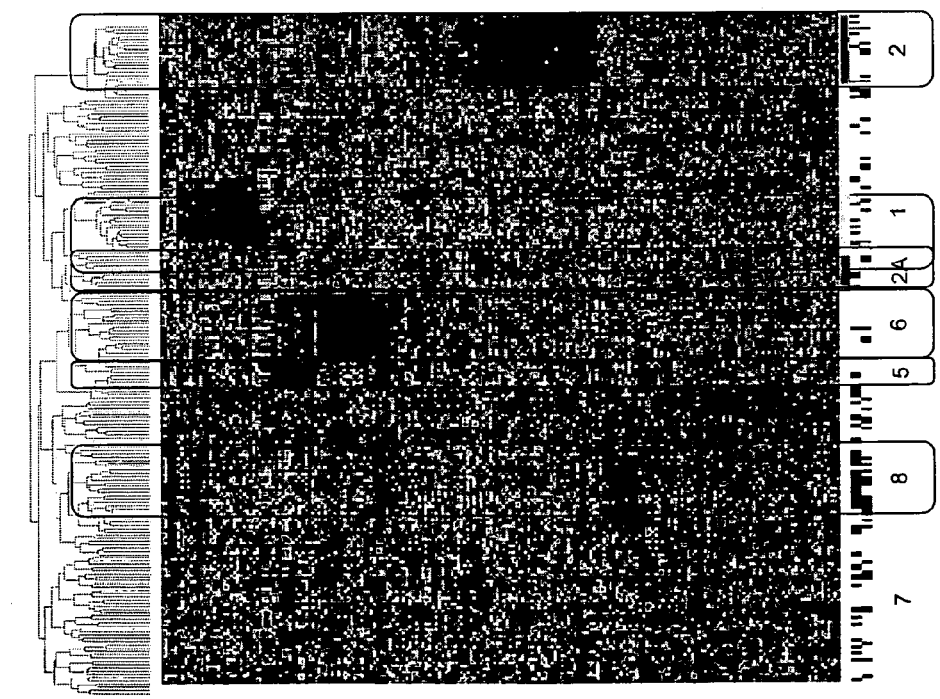
Figure 2C:
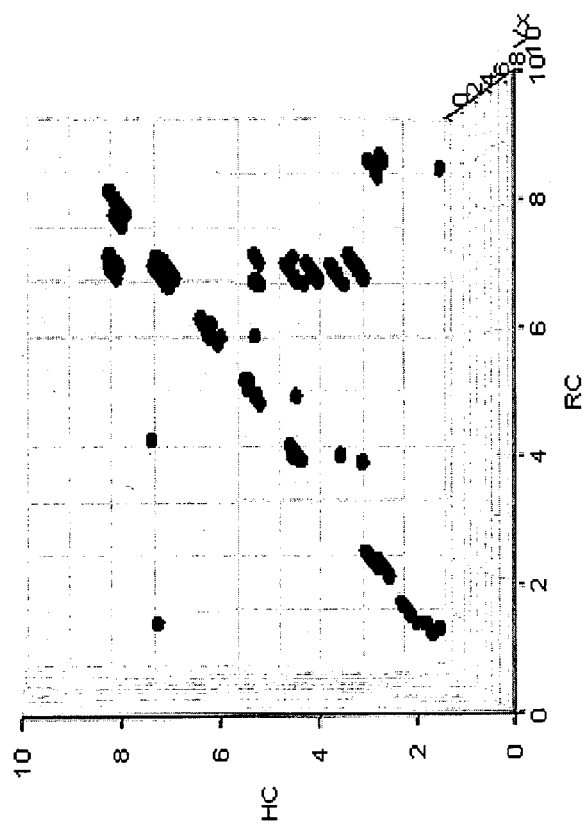

Hierarchical clustering using outlier genes also identified related groups within the population of ALL patients. Both COPA (FIG. 2A) and ROSE (FIG. 2B) analysis segregated patients into distinctive clusters that were assigned labels indicting the overlap of the members with groups identified in the hierarchical clustering shown in FIG. 1A. The similarities between the groups identified by the ROSE or COPA and hierarchical clustering are shown in FIG. 2C. The most highly related groups across all methods were determined by the largest number of shared samples: Cluster 1 (14), Cluster 2 (23), Cluster 6 (15) and Cluster 8 (17).

For each of the clustering methods we performed $\chi2$ analysis to determine if there appeared to be a relationship between selected clinically-relevant variables and cluster assignment.

The best statistical correlations with known translocations (MLL and E2A/PBX1) were found in the ROSE clusters, shown in Table 1A (a more complete relationship of the clinical correlates of both ROSE and hierarchical clusters are presented in the Supplement Tables 3S and 4S). Shaded cells in Table 1A highlight those specific variables that were determined by Fisher's Exact Tests to be highly significant between cluster groups. Both of the known chromosomal translocations in this cohort were assigned to specific clusters with 100% accuracy: cluster R1 contained exclusively the MLL translocations while all of the 41;19) E2A/PBX1 translocations clustered together in R2.

TABLE 1A

Association of Clinical Features with ROSE Clusters

| | | R1 | R2 | R2A | R4 | R5 | R6 | R7 | R8 | total | P (CHISQ) |
|---|---|---|---|---|---|---|---|---|---|---|---|
| Sex | Male | 11/21 | 11/23 | 6/11 | 11/13 | 8/11 | 17/21 | 56/83 | 17/24 | 137/207 | 0.1 |
| Translocation | MLL | 21/21 | 0/23 | 0/11 | 0/13 | 0/11 | 0/21 | 0/83 | 0/24 | 21/207 | <0.001 |
| | t(1;19) | 0/21 | 23/23 | 0/11 | 0/13 | 0/11 | 0/21 | 0/83 | 0/24 | 23/207 | <0.001 |
| Outcome | Relapse | 7/21 | 6/23 | 3/11 | 3/13 | 2/10 | 1/20 | 30/81 | 18/23 | 70/202 | <0.001 |
| MRD (d29) | Positive | 9/17 | 0/20 | 1/9 | 2/13 | 8/11 | 6/21 | 22/77 | 19/23 | 67/191 | <0.001 |
| Race | Hispanic | 4/21 | 6/23 | 2/11 | 2/13 | 0/10 | 3/20 | 19/83 | 15/24 | 51/205 | 0.001 |

TABLE 1B

Hazard Ratios and Logrank p-values for Clusters 6 and 8

| | Good Outcome Clusters | | | | Poor Outcome Clusters | | | |
|---|---|---|---|---|---|---|---|---|
| | R6 | C6 | H6 | V6 | R8 | C8 | H8 | V8 |
| P (log-rank) | 0.010 | 0.010 | 0.015 | 0.112 | <0.001 | <0.001 | <0.001 | 0.006 |
| Hazard Ratio | 0.117 | 0.117 | 0.126 | 0.404 | 3.740 | 3.187 | 2.736 | 1.959 |

There was no significant difference in the male/female ratio in any of the clusters, however all of the other clinical features showed notable correlations with one or more of the clusters. In particular, outcome (RFS) varied significantly among the clusters (p<0.001). The significance of this initial $\chi 2$ RFS finding was determined primarily to be influenced by two different clusters, R6 and R8. The Fisher's Exact Test of the RFS for these clusters revealed that R6 had a significantly better outcome than the remainder of the cohort (p=0.002) while R8 had a much poorer outcome (p<0.001). The 4-year RFS for R6 was 94.7% v. 63.6% for non-R6 and 20.9% for R8 v. 72.1% for non-R8. As is shown in Table 1B, cluster 6 and cluster 8 from all four methods partition patients into notably good (Cluster 6) and poor (Cluster 8) outcome groups and those cases clustered by ROSE had the best (R6; HR=0.117) and worst (R8; HR=3.74) hazard ratios.

Figure 3A:
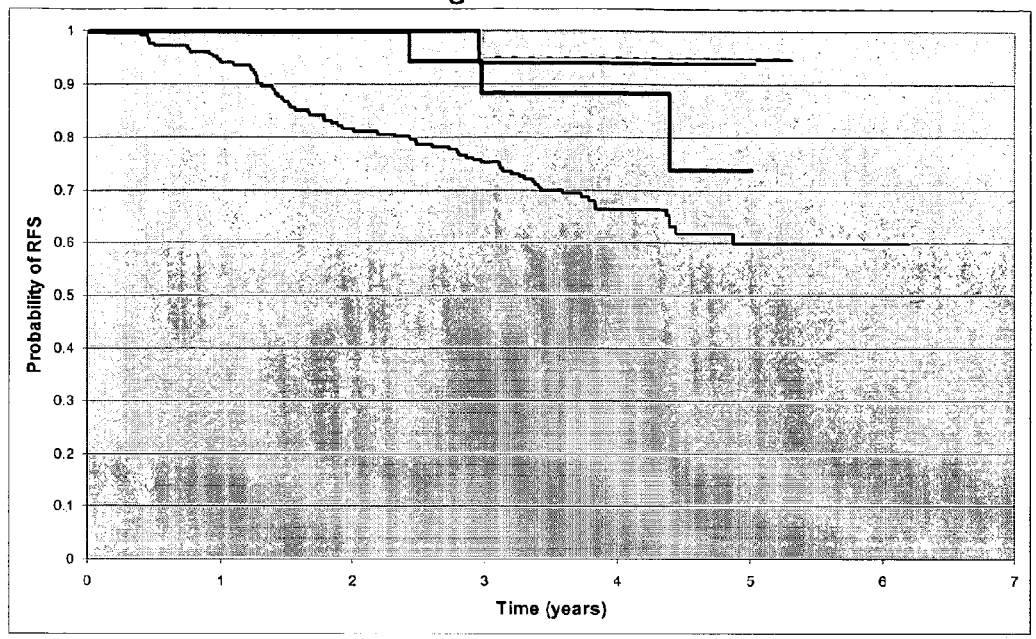
FIG. 3 shows Kaplan-Meier plots for clusters with aberrant outcome. RFS survival are shown for cluster 6 (Panel A) and cluster 8 (Panel B) for patients identified by multiple algorithms. In panel 3B, the data for all 207 samples are shown with the line furthermost to the right. In panel 3B, H8 is represented by the central line in the graph, V8 is represented by the line second from the right, R8 is represented by the line running from the top of the graph to the bottom and is furthermost to the left and C8 is represented by the line which overlaps with R8 on the left of the graph.
Figure 3B:
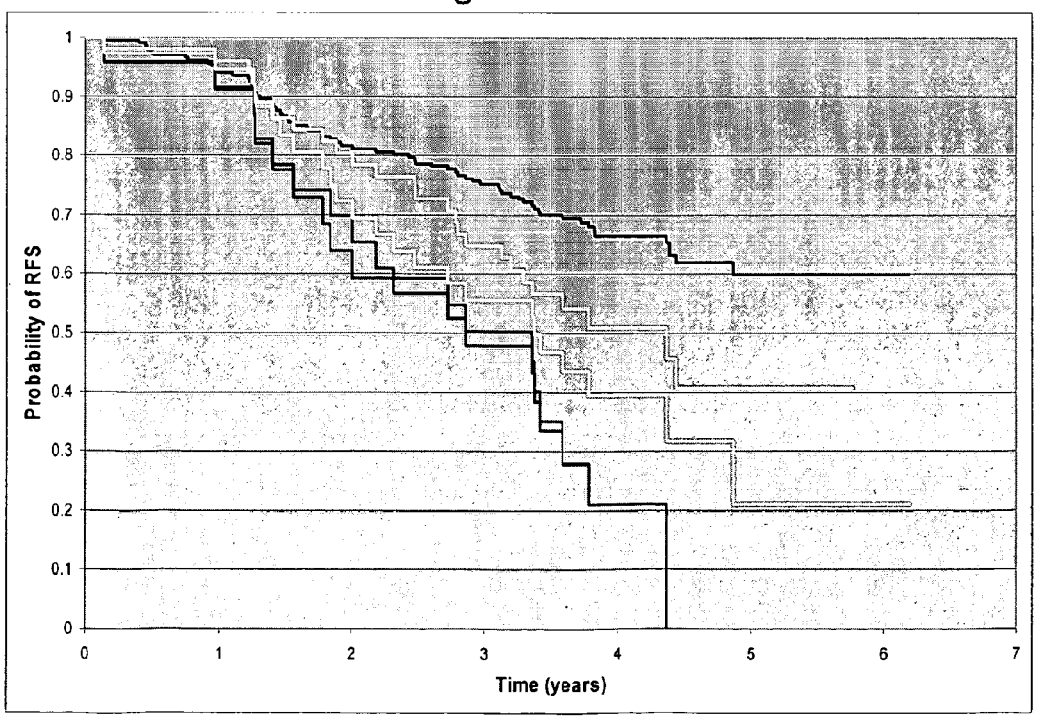

The Kaplan-Meier plot shown in FIG. 3A presents the RFS for cluster 6 segregated by each statistical method. Both ROSE and COPA identified exactly the same patients, while hierarchical clustering differed by only one. The log rank p-values for these three methods were also essentially identical (ROSE and COPA=0.010; hierarchical clustering=0.015), as would be expected based on their membership. While the patients clustered by VxInsight had a somewhat better outcome, these data were not as definitive as those generated by the other analyses, and only trended toward statistical significance (p=0.112). The Kaplan-Meier plot for the poor outcome clusters is shown in FIG. 3B. All four methods identified a population that fared significantly worse than the cohort as determined by log rank analysis (Table 1B).

Day 29 MRD also differed between ROSE clusters (p<0.001; Table 1A). A Fisher's Exact Test indicated that R8 had a higher proportion of MRD positive patients on day 29, as might be expected given their eventual poor outcome. Surprisingly, R6, comprising patients with a very good outcome, did not have a corresponding marked increase in MRD negative cases. In addition, all of the patients assigned to R2 (t(1;19) E2A/PBX1 translocations) were MRD negative on day 29, despite the fact that the RFS for this group was not different than that seen for the entire cohort. Similarly, R5 had a significant increase in MRD positive patients at day 29 without a corresponding alteration in RFS.

Finally, race also varied significantly across the ROSE clusters (p<0.001). While Hispanic/Latino patients were present in all clusters except R5, the proportion of Hispanics in R8, the cluster associated with the poorest outcome, was markedly higher than that in every other cluster (p<0.001). None of the other clusters had a significantly disproportionate number of any ethnic groups.

Method Validation in an Independent Data Set

Figure 4A:
FIG. 4 shows the validation of ROSE in CCG 1961 data set. In Panel A a heat map generated as described in FIG. 2B identifies groups of samples with similar patterns of genes expression. The colored boxes indicate the clusters with similarities to those shown in the primary data set. In Panel B the RFS curve for cluster R8 in Panel A is shown in red, while the RFS for samples not in that group is shown in black.
Figure 4B:
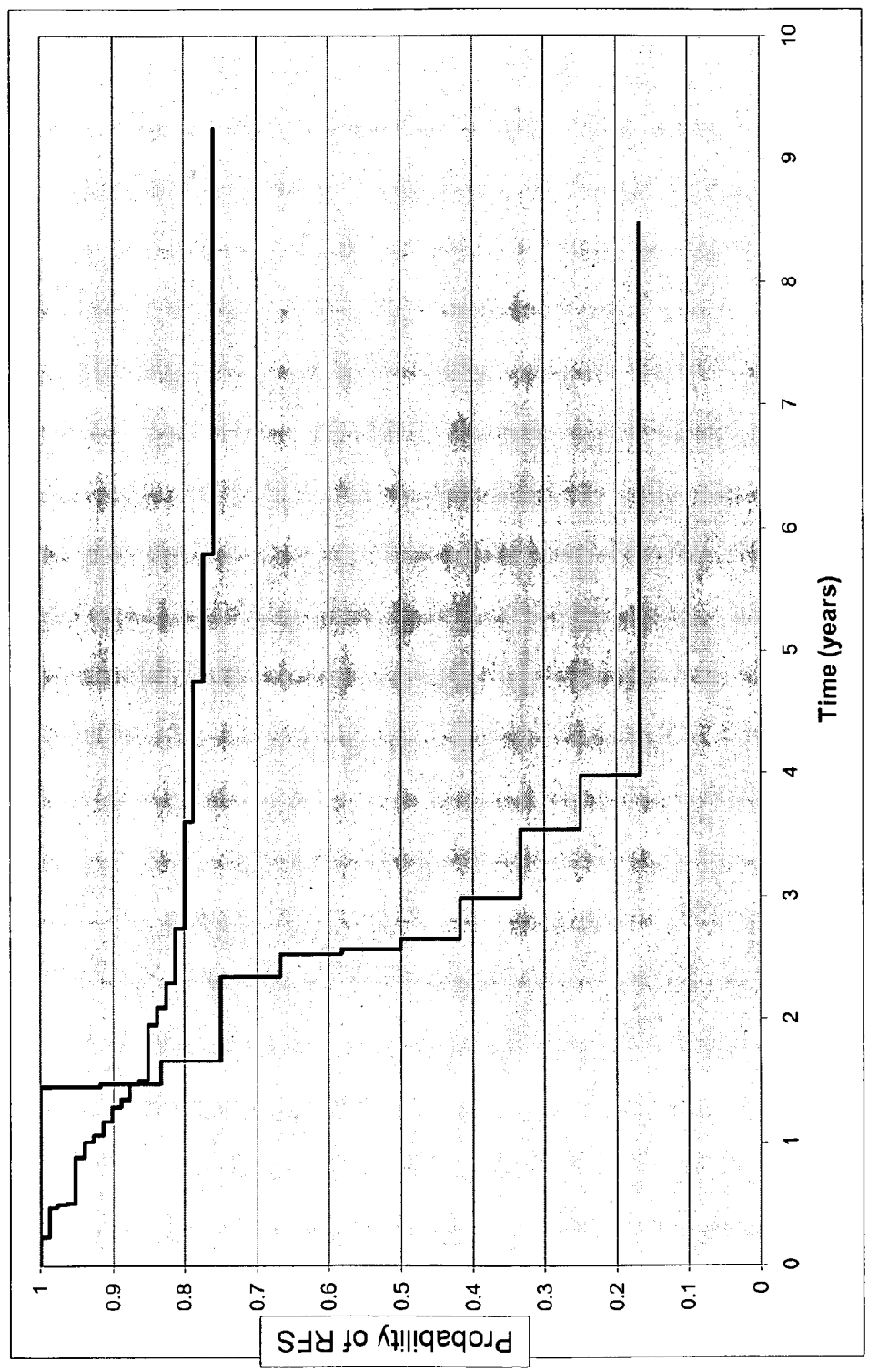

The validity of the ROSE analysis as a method to accurately segregate patients based on outcome was assessed in an independent data set of 99 children and adolescents with NCI high risk ALL treated on the CCG 1961 trial of standard vs. augmented BFM therapy.[11] Bhojwani et al recently reported U133plus2.0 microarray data from 99 patients enrolled in this trial.[18] The CCG 1961 patient cohort was selected to be representative of patients with good vs. poor early marrow responses, and sustained remission vs. relapse (see Bhojwani et al[18] for description,), and is therefore enriched for patients that experienced relapse. The microarray data obtained from the 99 CCG 1961[18] patients was clustered by ROSE as shown in FIG. 4A. These data were masked similarly to P9906 and the same threshold for cluster identification (7-fold) was applied. The full details are described in the Supplement. Several relevant groups were identified despite the lower number of patients. A novel cluster not seen in the P9906 cohort because of their low representation contained all of the patients with t(12;21) translocations. We also identified subgroups analogous to R1 and R2, consisting of patients with MLL rearrangements or t(1;19) E2A/PBX1 translocations, respectively. In addition, clusters with expression patterns corresponding to R6 (Good Outcome Cluster) and R8 (Poor Outcome Cluster) were identified in the CCG 1961 patients. R6 only contained 6 samples, precluding a meaningful statistical analysis of RFS. The Kaplan-Meier plot for the larger R8 cluster (13 patients) in CCG 1961 is shown in FIG. 4B. In a manner similar to what was seen in the P9906 patients, the ROSE analysis identified a group of patients with a markedly low probability of RFS (log rank p<0.001; HR=4.22). These results confirm the robust nature of the prediction of poor outcome in the R8 cluster.

The top 50 probe sets as determined by the highest average rank order for clusters R6 and R8 are shown in Tables 2 and 3. The corresponding probes sets for the remainder of the clusters are presented as Supplementary Data. A number of these probe sets are designated only as "transcribed" loci by Affymetrix. We mapped the position of many of these using the UCSC Genome Browser (genome.ucsc.edu/) to regions in the vicinity of the well-characterized genes also identified in the clustering analysis. The probe sets identified in this fashion are shown with an asterisk next to their gene name in Tables 2 and 3. Regions immediately 3' of GAB1, GPR110 and CD99 were present in the top R8 rank order probe sets. Intronic sequences in SLC37A3, CD99 and NRXN3 were also identified. Many of the genes associated with R8 are transmembrane proteins involved in cell signaling and adhesion (e.g. GPR110, IFITM1-3, MUC4, NRXN3, and CD99). A number of interferon-induced genes appear in this list as well (IFITM1-3 and SEMA6A), consistent with a gene pattern associated with an immune response. Only 3 of the genes (CD99, IGJ, and GAB1) are correlated with specific developmental patterns in lymphocytes.

TABLE 2

Top 50 Rank Order Genes for R6 (asterisks denote gene assignments using UCSC Genome Browser)

| Probe Set ID | Gene | Gene Title | EntrezID | Band |
| --- | --- | --- | --- | --- |
| 220059_at | STAP1 | signal transducing adaptor family member 1 | 26228 | 4q13.2 |
| 228240_at | CENTG2* | Full-length cDNA clone CS0DM002YA18 of Fetal liver of Homo sapiens (human) | — | 2q37.2 |
| 204066_s_at | CENTG2 | centaurin, gamma 2 | 116987 | 2p24.3-p24.1 |
| 233225_at | CENTG2* | CDNA FLJ36087 fis, clone TESTI2020283 | — | 2q37.2 |
| 206756_at | CHST7 | carbohydrate (N-acetylglucosamine 6-O) sulfotransferase 7 | 56548 | Xp11.23 |
| 240758_at | CENTG2* | — | — | 2q37.2 |
| 1554343_a_at | STAP1 | signal transducing adaptor family member 1 | 26228 | 4q13.2 |
| 230537_at | PCDH17* | — | — | 13q21.1 |
| 203921_at | CHST2 | carbohydrate (N-acetylglucosamine-6-O) sulfotransferase 2 | 9435 | 3q24 |
| 230179_at | LOC285812 | hypothetical protein LOC285812 | 285812 | 6p23 |
| 219821_s_at | GFOD1 | glucose-fructose oxidoreductase domain containing 1 | 54438 | 6pter-p22.1 |
| 1554486_a_at | C6orf114 | chromosome 6 open reading frame 114 | 85411 | 6p23 |
| 209593_s_at | TOR1B | torsin family 1, member B (torsin B) | 27348 | 9q34 |
| 203329_at | PTPRM | protein tyrosine phosphatase, receptor type, M | 5797 | 18p11.2 |
| 227289_at | PCDH17 | protocadherin 17 | 27253 | 13q21.1 |
| 1552398_a_at | CLEC12A | C-type lectin domain family 12, member A | 160364 | 12p13.2 |
| 242457_at | — | Transcribed locus | — | 5q21.1 |
| 205656_at | PCDH17 | protocadherin 17 | 27253 | 13q21.1 |
| 1555579_s_at | PTPRM | protein tyrosine phosphatase, receptor type, M | 5797 | 18p11.2 |
| 1556593_s_at | — | CDNA FLJ40061 fis, clone TESOP2000083 | — | 3q23 |
| 228863_at | PCDH17 | protocadherin 17 | 27253 | 13q21.1 |
| 202336_s_at | PAM | peptidylglycine alpha-amidating monooxygenase | 5066 | 5q14-q21 |
| 235968_at | CENTG2 | centaurin, gamma 2 | 116987 | 2p24.3-p24.1 |
| 225611_at | — | — | — | 5q12.3 |
| 210944_s_at | CAPN3 | calpain 3, (p94) | 825 | 15q15.1-q21.1 |
| 211340_s_at | MCAM | melanoma cell adhesion molecule | 4162 | 11q23.3 |
| 233038_at | CENTG2* | CDNA: FLJ22776 fis, clone KAIA1582 | — | 2q37.2 |
| 219470_x_at | CCNJ | cyclin J | 54619 | 10pter-q26.12 |
| 244665_at | ITGA6* | Transcribed locus | — | 2q31.1 |
| 230954_at | C20orf112 | chromosome 20 open reading frame 112 | 140688 | 20q11.1-q11.23 |
| 211890_x_at | CAPN3 | calpain 3, (p94) | 825 | 15q15.1-q21.1 |
| 226342_at | SPTBN1 | spectrin, beta, non-erythrocytic 1 | 6711 | 2p21 |
| 202746_at | ITM2A | integral membrane protein 2A | 9452 | Xq13.3-Xq21.2 |
| 209087_x_at | MCAM | melanoma cell adhesion molecule | 4162 | 11q23.3 |
| 223130_s_at | MYLIP | myosin regulatory light chain interacting protein | 29116 | 6p23-p22.3 |
| 228098_s_at | MYLIP | myosin regulatory light chain interacting protein | 29116 | 6p23-p22.3 |

TABLE 2-continued

Top 50 Rank Order Genes for R6 (asterisks denote gene assignments using UCSC Genome Browser)

| Probe Set ID | Gene | Gene Title | EntrezID | Band |
|---|---|---|---|---|
| 225613_at | MAST4 | microtubule associated serine/threonine kinase family member 4 | 375449 | 5q12.3 |
| 40016_g_at | MAST4 | microtubule associated serine/threonine kinase family member 4 | 375449 | 5q12.3 |
| 232227_at | AF161442* | HSPC324 | — | 9q34.3 |
| 202747_s_at | ITM2A | integral membrane protein 2A | 9452 | Xq13.3-Xq21.2 |
| 228097_at | MYLIP | myosin regulatory light chain interacting protein | 29116 | 6p23-p22.3 |
| 229091_s_at | CCNJ | cyclin J | 54619 | 10pter-q26.12 |
| 204836_at | GLDC | glycine dehydrogenase (decarboxylating) | 2731 | 9p22 |
| 201656_at | ITGA6 | integrin, alpha 6 | 3655 | 2q31.1 |
| 215177_s_at | ITGA6 | integrin, alpha 6 | 3655 | 2q31.1 |
| 214475_x_at | CAPN3 | calpain 3, (p94) | 825 | 15q15.1-q21.1 |
| 1558621_at | CABLES1 | Cdk5 and Abl enzyme substrate 1 | 91768 | 18q11.2 |
| 229597_s_at | WDFY4 | WDFY family member 4 | 57705 | 10q11.23 |
| 231166_at | GPR155 | G protein-coupled receptor 155 | 151556 | 2q31.1 |
| 239956_at | — | CDNA FLJ40061 fis, clone TESOP2000083 | — | 3q23 |

TABLE 3

Top 50 Rank Order Genes for R8 (asterisks denote gene assignments using UCSC Genome Browser)

| Probe Set ID | Gene | Gene Title | EntrezID | Band |
|---|---|---|---|---|
| 236489_at | GPR110* | Transcribed locus | — | 6p12.3 |
| 212592_at | IGJ | Immunoglobulin J polypeptide, linker protein for immunoglobulin alpha and mu polypeptides | 3512 | 4q21 |
| 217109_at | MUC4 | mucin 4, cell surface associated | 4585 | 3q29 |
| 240586_at | ENAM | Enamelin | 10117 | 4q13.3 |
| 205795_at | NRXN3 | neurexin 3 | 9369 | 14q31 |
| 238689_at | GPR110 | G protein-coupled receptor 110 | 266977 | 6p12.3 |
| 217110_s_at | MUC4 | mucin 4, cell surface associated | 4585 | 3q29 |
| 236750_at | NRXN3* | Transcribed locus | — | 14q31.1 |
| 242051_at | CD99* | Transcribed locus | — | Xp22.33; Yp11.31 |
| 204895_x_at | MUC4 | mucin 4, cell surface associated | 4585 | 3q29 |
| 201029_s_at | CD99 | CD99 molecule | 4267 | Xp22.32; Yp11.3 |
| 201028_s_at | CD99 | CD99 molecule | 4267 | Xp22.32; Yp11.3 |
| 229114_at | GAB1* | CDNA clone IMAGE:4801326 | — | 4q31.21 |
| 206873_at | CA6 | carbonic anhydrase VI | 765 | 1p36.2 |
| 201876_at | PON2 | paraoxonase 2 | 5445 | 7q21.3 |
| 222154_s_at | LOC26010 | viral DNA polymerase-transactivated protein 6 | 26010 | 2q33.1 |
| 210830_s_at | PON2 | paraoxonase 2 | 5445 | 7q21.3 |
| 235988_at | GPR110 | G protein-coupled receptor 110 | 266977 | 6p12.3 |
| 216565_x_at | LOC391020 | interferon induced transmembrane protein pseudogene | 391020 | 1p36.11 |
| 215021_s_at | NRXN3 | neurexin 3 | 9369 | 14q31 |
| 225912_at | TP53INP1 | tumor protein p53 inducible nuclear protein 1 | 94241 | 8q22 |
| 226002_at | GAB1* | CDNA clone IMAGE:4801326 | — | 4q31.21 |
| 214022_s_at | IFITM1 | interferon induced transmembrane protein 1 (9-27) | 8519 | 11p15.5 |
| 212203_x_at | IFITM3 | interferon induced transmembrane protein 3 (1-8U) | 10410 | 11p15.5 |
| 1563357_at | SERPINB9* | MBNA; cDNA DKFZp564C203 (from clone DKFZp564C203) | — | 6p25.2 |
| 225998_at | GAB1 | GRB2-associated binding protein 1 | 2549 | 4q31.21 |
| 201315_x_at | IFITM2 | interferon induced transmembrane protein 2 (1-8D) | 10581 | 11p15.5 |

TABLE 3-continued

Top 50 Rank Order Genes for R8 (asterisks denote gene assignments using UCSC Genome Browser)

| Probe Set ID | Gene | Gene Title | EntrezID | Band |
|---|---|---|---|---|
| 201601_x_at | IFITM1 | interferon induced transmembrane protein 1 (9-27) | 8519 | 11p15.5 |
| 230643_at | WNT9A | wingless-type MMTV integration site family, member 9A | 7483 | 1q42 |
| 212974_at | DENND3 | DENN/MADD domain containing 3 | 22898 | 8q24.3 |
| 203435_s_at | MME | membrane metallo-endopeptidase | 4311 | 3q25.1-q25.2 |
| 223741_s_at | TTYH2 | tweety homolog 2 (*Drosophila*) | 94015 | 17q24 |
| 212975_at | DENND3 | DENN/MADD domain containing 3 | 22898 | 8q24.3 |
| 207426_s_at | TNFSF4 | tumor necrosis factor (ligand) superfamily, member 4 (tax-transcriptionally activated glycoprotein 1, 34 kDa) | 7292 | 1q25 |
| 52731_at | FLJ20294 | hypothetical protein FLJ20294 | 55626 | 11p11.2 |
| 215028_at | SEMA6A | sema domain, transmembrane domain (TM), and cytoplasmic domain, (semaphorin) 6A | 57556 | 5q23.1 |
| 229649_at | NRXN3 | neurexin 3 | 9369 | 14q31 |
| 1559315_s_at | LOC144481 | hypothetical protein LOC144481 | 144481 | 12q22 |
| 205983_at | DPEP1 | dipeptidase 1 (renal) | 1800 | 16q24.3 |
| 226840_at | H2AFY | H2A histone family, member Y | 9555 | 5q31.3-q32 |
| 230161_at | CD99* | Transcribed locus | — | Xp22.33; Yp11.31 |
| 223304_at | SLC37A3 | solute carrier family 37 (glycerol-3-phosphate transporter), member 3 | 84255 | 7q34 |
| 218862_at | ASB13 | ankyrin repeat and SOLS box-containing 13 | 79754 | 10p15.1 |
| 213939_s_at | RUFY3 | RUN and FYVE domain containing 3 | 22902 | 4q13.3 |
| 207112_s_at | GAB1 | GRB2-associated binding protein 1 | 2549 | 4q31.21 |
| 227856_at | C4orf32 | chromosome 4 open reading frame 32 | 132720 | 4q25 |
| 238880_at | GTF3A | general transcription factor IIIA | 2971 | 13q12.3-q13.1 |
| 1569666_s_at | SLC37A3* | *Homo sapiens*, clone IMAGE:5581630, mRNA | — | 7q34 |
| 209365_s_at | ECM1 | extracellular matrix protein 1 | 1893 | 1q21 |
| 203373_at | SOCS2 | suppressor of cytokine signaling 2 | 8835 | 12q |

Sequences 3' of CENTG2, CHST2 and MAST4 as well as introns of CENTG2 and ITGA6 were among the high ranking probe sets forming the R6 signature. This pattern of expression suggests the possibility of alternative splicing or a generalized elevation in expression within certain chromosomal regions. Several of the genes forming the R6 signature are also postulated to be involved with cell signaling and adhesion (CENTG2, CLEC12A, GPR155, MCAM, ITM2A, PCDH17, and PTPRM). In addition, two cyclin associated genes (CCNJ and CABLES1) are preferentially associated with the Good Outcome Cluster. While the R6 genes are more commonly expressed in lymphocytes, there is no obvious pattern of expression that is associated with a particular stage of differentiation or cell type.

Discussion

Gene expression profiling studies of pediatric ALLs have shown marked heterogeneity.[3] In approximately 35-40% of all cases, specialized molecular techniques and gene cloning have identified recurring genetic abnormalities that are associated with drug responsiveness, prediction of relapse, and overall survival.[4] These genetic abnormalities are primarily seen in children who have either better treatment outcomes and "low risk" disease (such as TEL/AML1 or trisomies of chromosomes 4, 10, and 17) or poor outcomes and "very high risk" disease (such as BCR/ABL or hypodiploidy). Classification of the remaining children for determination of risk stratified therapy relies on clinical parameters such as patient age, presenting white blood cell count, and response to induction therapy. We used a series of unsupervised clustering algorithms to analyze gene expression profiles from a retrospective cohort of ALL patients with a clinical profile that suggested that they were at high risk for relapse. These methods identified overlapping groups of transcripts that defined clusters with important cytogenetic and clinical characteristics.

We used four different unsupervised clustering algorithms to analyze the gene expression data in pretreatment specimens from a cohort of 207 children with high-risk ALL (HR-ALL). This type of analysis, without knowledge of prior class definitions, allows for identification of fundamental subsets of patients sharing similar gene expression signatures. The composite result is a separation of the HR-ALL cases into eight distinct clusters based on traditional hierarchal clustering methods. The additional three methods show significant overlap in cluster membership with traditional hierarchical clustering, but allow for greater discrimination of unique gene signatures that relate to outcome differences. The strength of this type of approach is apparent when using the more restrictive clustering algorithms (ROSE and COPA), in the effective identification and clustering of HR-ALL specimens with translocations into two distinct clusters (clusters 1 and 2) using an unsupervised approach.

As had been seen in other studies,[19,20] we discovered gene signatures characteristic of specific chromosomal abnormalities common in ALL. In the primary data set we found two clusters that contained 100% of the t(1;19) translocations and MLL rearrangements. In the validation data we also found a signature that defined subjects with a t(12;21) translocation.

This pattern was not seen in the original data because only three patients with this lesion were enrolled in COG P9906. Interestingly, both the ROSE and COPA analysis identified a distinct cluster with a signature related to that seen in t(1;19) subjects. While the pattern of gene expression was distinct enough that the samples did not cluster together with the t(1;19) patients, the similarities were sufficient to conclude that these patients share a fundamental underlying process that was observed even in the absence of the translocation.

Two of the clusters described by multiple unsupervised algorithms had remarkable differences in RFS compared to the cohort as a whole, even though all the patients enrolled in COG P9906 were identified as being at higher risk of relapse based on clinical characteristics (age and white blood cell count). Cluster 8 identified by all the statistical methods consisted of patients that fared far worse that the 60% RFS seen in the entire population. Only 20% of the 37 patients identified by hierarchical clustering were disease-free at 5 years, while all of the 24 patients segregated by ROSE relapsed or were censored. In contrast, Cluster 6 identified by ROSE/COPA and hierarchical clustering consisted of a group of approximately 20 patients with a 95% rate of RFS. Therefore we identified a marked heterogeneity in treatment response even in a group of children who had been preselected in a high risk category. Whether the patients in cluster 6 are actually children who would respond well to less aggressive therapy, or who are good responders to the intensive treatment of COG P9906 and would fail conventional protocols is not clear. It is clear however that cluster 8 consists of patients that relapse at very high rates and are candidates for novel treatment regimes.

End induction MRD has been shown to be a robust predictor of RFS in many studies, including COG P9906.[9,21,22] Interestingly, although the patient numbers in subgroups are relatively small, the predictive power of some gene signatures seemed to provide more information than day 29 MRD. Although the overall MRD positivity of Cluster 8 was highly predictive of eventual relapse, this was not the case for many of the other clusters. In particular, the MRD status of cluster 6 was not statistically different from the entire cohort even though only 1/21 patients in this group relapsed, and the patient who relapsed was day 29 MRD negative. Similarly, although all patients in cluster 2, all of whom had the t(1;19), were MRD negative at day 29, the relapse risk for these patients was quite similar to that of the overall group of P9906 patients. These findings are consistent with the observation of Borowtiz et al[9] that the most robust risk stratification algorithms integrate genetic features of the leukemia and early treatment response as measured by end induction MRD. It is also possible that further characterization of additional high risk ALL patients will result in a high enough number of patients in each cohort that more conclusive statements concerning the predictive role of MRD can be made.

It has been previously reported that Hispanic children with B-precursor ALL have poorer responses to therapy.[23,24] While we found that patients of Hispanic/Latino ethnicity were found in all the clusters, they were preferentially represented in cluster 8, the poor outcome group. Twelve of the 15 (80%) of the Hispanics in this cluster relapsed, compared to 11/36 (31%) of the Hispanics not in cluster 8. Since the relapse rate for non-Hispanics in cluster 8 was also high (6/9; 67%) it seems that we identified patients of all races who relapsed, not just simply Hispanic patients. It is possible that the nature of the pattern of gene expression identified in studies such as that reported here will provide some insight into preferential susceptibilities of specific ethnic groups to high risk ALLs.

The pattern of gene expression in individual cohorts will provide insights into fundamental biological pathways that underlie the neoplastic diseases, as well as providing a potential population of genes and pathways that can be targeted by novel therapies. The top-ranked members of the clusters that predict both good and poor outcome were dominated by genes involved in cell signaling and adhesion. CD99 is overexpressed in a variety of tumors[25,26] and has served as a therapeutic target in investigational therapies.[27] Overexpression of MUC4 has been associated with a poor prognosis in a variety of solid tumors[28,29] but has not been previously linked to outcome in leukemias. In contrast GAB1 has been shown to be predictive of favorable response in BCR/ABL-ALL[30] and its expression has been correlated with responsiveness to imatinib in rheumatoid arthritis.[31] The CABLES1 gene has been described as a growth suppressor[32,33] and is frequently deleted in solid tumors[34,35] although it has not been previously described as playing a significant role in leukemia. Its overexpression in the good outcome group is consistent with the suppressed growth and senescence that might be expected in light of the excellent RFS of this group of patients.

There are similarities between the genes that we describe here and those reported in other studies. Cluster 6 (good outcome group) shares some features with the "novel" cluster of patients initially described by Yeoh et al[5] and later reinvestigated by Ross et al.[36] This novel cluster from the previous studies has also been reported to be frequently associated with deletions of the ERG gene.[37] We analyzed the publicly available Affymetrix U133A data from the second study by ROSE and identified a distinct cluster of 13 members. Comparison of the top rank order of this group to cluster 6 resulted in a set of 50 genes from the top 200 that were identical, even though the U133A array has less than half the probe sets on U133 Plus 2.0 arrays used in our studies. Despite the similarities in the composition of the clusters, the earlier studies did not find a correlation to clinical features, contrasted with the favorable prognosis patients in our group of high risk patients. Several genes with expression patterns associated with the R8 poor outcome cluster are also among those previously identified as distinguishing the BCR/ABL subtype of ALL from other childhood ALL subtypes.[33] These shared genes include MUC4, GPR110, CD99, IGJ and IFITM3. This overlap in expression pattern between these two distinctive high-risk ALL subgroups suggests a biological similarity despite the lack of BCR/ABL translocation in the R8 group.

A recent report[35] measured gene expression in a series of ALL patients and proposed a three gene predictor of relapse. The single gene within this set whose induction was predictive of relapse was IGJ, a top-ranked gene in our poor outcome cluster. However none of the other genes identified in the extended data set in this paper as being related to relapse overlapped with those described here. There are a number of potential reasons for this discrepancy, although differences in clustering techniques might well be the basis of the differences. The Random Forest technique used by Hoffman et al.[38] did not cluster the data of Ross et al.[36] in a manner that predicted outcome, while the combination of techniques used here extracted informative groups.

This gene expression profiling study highlights the divergent mechanisms and pathways of leukemic transformation that are not recognized by current methods of pediatric ALL diagnosis, classification and risk assignment. No bias was induced during cluster selection in this analysis of HR-ALL, and therefore these expression clusters likely represent the true intrinsic biology in this cohort of patients. We are now determining the novel underlying genetic abnormalities associated with each of these clusters through correlated studies of whole genome copy number change and direct gene sequencing in a National Cancer Institute—Sponsored TARGET project. The identification of new genetic abnormalities will allow for targeted therapy in this group of patients who have historically have had a poor response on their therapeutic trials.

Further Details of Analysis

Masking and Filtering of Probe Sets

Masking of Probe Set

Prior to any intensity analysis, the microarray data were first masked to remove those probes found to be uninformative in a majority of the samples. Removal of these probe pairs improves the overall quality of the data and eliminates many non-specific signals that are shared by a particular sample type. This was accomplished by evaluating the signals for all probes across all 207 samples and then identifying those probe pairs for which the mismatch (MM) signals exceeded their corresponding perfect match signals (PM) in more than 60% of the samples. Masking removed 94,767 probe pairs and had some impact on 38,588 probe sets (71%). As shown in Table 1C, the net impact of masking was a significant increase in the number of present calls coupled with a dramatic decrease in the number of absent. The masked data also removed 7 probe sets entirely (none of which represented human genes). This resulted in the number of available probe sets on the microarray being reduced from 54,675 to 54,668.

TABLE 1C

Overall impact of masking on microarray calls

| | Present | Marginal | Absent | No call |
|---|---|---|---|---|
| Raw | 34.9 | 1.7 | 63.3 | 0 |
| Masked | 48.0 | 3.1 | 48.9 | 0 (7) |

Filtering of Probe Sets

All four unsupervised learning methods began with the full complement of probe sets (54,688 after masking). VxInsight (VX) used the intensity values for the probe sets called either present or marginal (as determine by GCOS 1.4) and treated those with absent calls as missing data. Traditional hierarchical clustering method (HC) applied two separate filtering methods to refine the number of starting probes. First, only those probe sets having present calls in more than 50% of the samples were included (23,775). This list was then distilled further by removing those genes that are known to simply determine sex (XIST, SRY, etc.) and those probe sets that by t-test analysis were comparable to these sex-related genes (1,828 total). The final number of evaluable probe sets was 21,947. The expression patterns for these probe sets were then analyzed and ordered by their variance. The 100 probe sets with the highest variance were used for clustering. ROSE and COPA simply removed the Affymetrix controls (probe sets with AFFX prefix) and used all of the remaining 54,615 probe sets for analysis.

Gene Selection for Clustering

ROSE Gene Selection in P9906

Figure 1C:
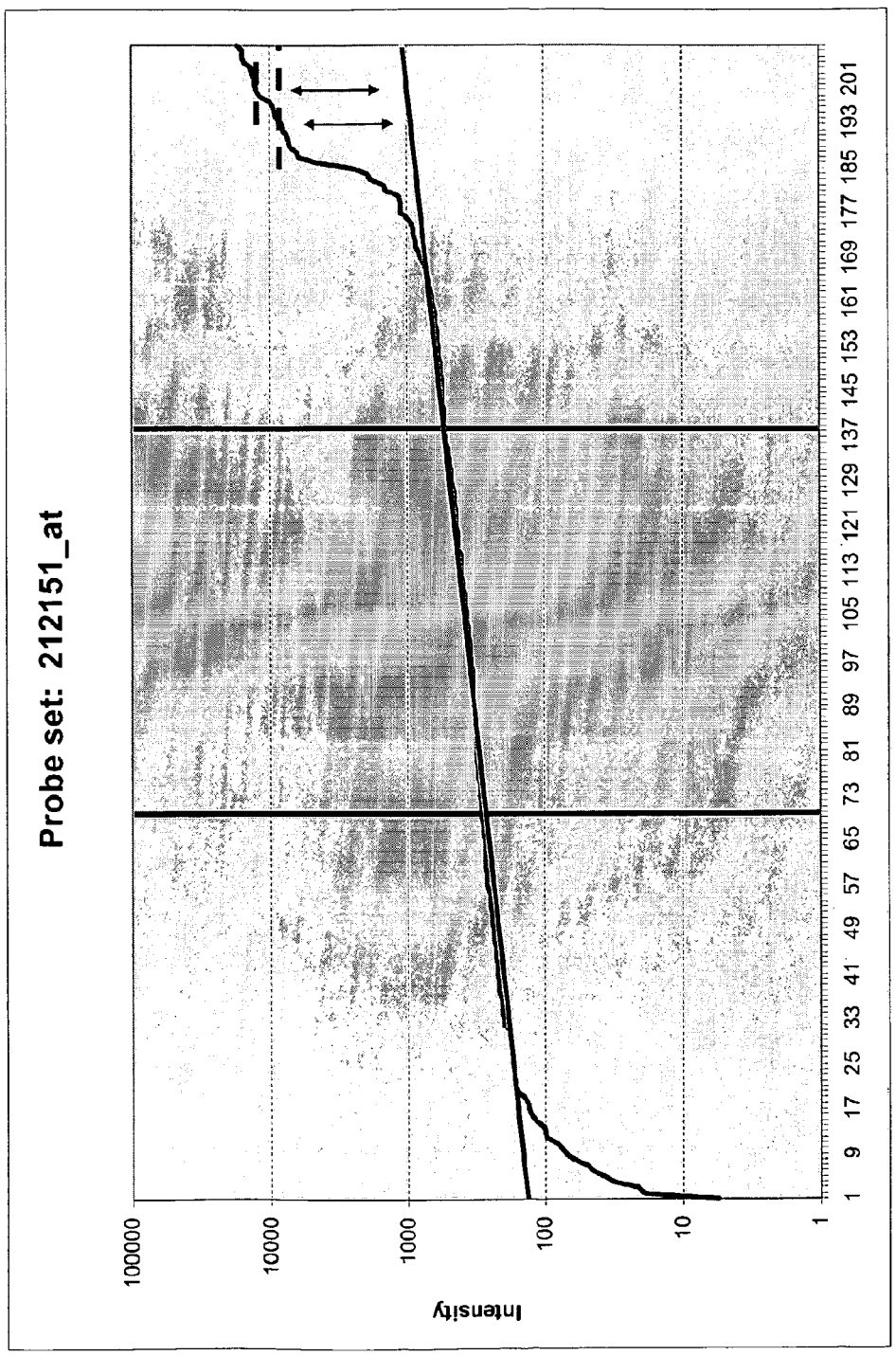

The intensity values for each of the 54,615 probe sets were individually plotted in ascending order. The plots were divided into thirds and the intensities from the middle third were used to generate trend lines by least squares analysis. Groups of 2*k (where k is an integer from 2 to one third of the sample size) were sampled from each end of the intensity plots and the median intensities of these groups were compared to the trend lines. FIG. 1C illustrates how this is done. Increasing sized groups were sampled from each end until the median intensity of a group failed to exceed the desired threshold. The largest value of k for which each probe set surpassed the threshold was recorded. The probe sets were then ordered by their maximum k values. In this study a probe set was selected for clustering if 6≤k≤30 and the median intensity of the sampled group was at least 7-fold its corresponding value on the trend line. This range of k values was selected in order to find groups in the range of 12 or more members (greater than 5% of the population size) and not exceeding 60 members. Groups smaller than 5% of the population were unlikely to yield any statistically significant results while those of approximately ⅓ the sample size or greater were likely to identify clinical features such as gender. The 7-fold threshold was chosen to minimize the impact of signal noise on probe set selection and also to limit the total number of probe sets to be used for clustering. Lower thresholds result in the inclusion of many more probe sets while higher thresholds dramatically reduce the number. Only 215 probe sets out of 54,615 satisfied these criteria of 7× threshold and k values between 6 and 30, inclusive.

ROSE Gene Selection in CCG 1961

Masking was applied to the CCG 1961 data set exactly the same way as in P9906. The same 7-fold threshold for intensity was also used. Because of the smaller number of patients in this data set a probe set was selected for clustering if 6≤k≤20, rather than an upper k of 30. Due to the noise of some of these microarrays, a lower limit intensity of 150 was applied (roughly twice the background across all chips). This prevented misleading signals at, or below, the level of background from giving a misleadingly high slope to the trend line. This was accomplished by substituting the value of 150 for any lower intensity. This process also dampened the apparent deviation of low signals from median.

COPA Gene Selection

As with ROSE, the intensities of the remaining 54,615 probe sets were used for the selection of COPA genes. The COPA method was applied essentially as described by Tomlins et al.[1] First, the median expression for each probe set was set to zero. Secondly, the median absolute deviation (MAD) was calculated and the intensities for each probe set were divided by its MAD. Finally, these MAD-normalized intensities at the $95^{th}$ percentile for each probe set were sorted. In order to make the comparison of COPA and ROSE more direct, an equal number of probe sets were selected from the top of sorted list of $95^{th}$ percentile COPA probe sets. From these 215 probe sets it was determined that 6 corresponded to the XIST gene and would simply segregate the boys and girls. After removal of these XIST probe sets 209 remained for clustering.

Clustering and Grouping Methods

COPA and ROSE Clustering

The hierarchical clustering of COPA and ROSE genes were performed using EPCLUST (an online tool that is part of the Expression Profiler suite at www.bioinf.ebc.ee).[2] The data for each probe set were converted to values of $\log_2$ (intensity/median) and were uploaded to EPCLUST. Hierarchical clustering was performed using linear correlation based distance (Pearson, centered) and average linkage (weighted group average, WPGMA). A threshold branch distance was applied and all clusters containing more than 10 members (greater than 5% of the samples) were retained and labeled.

Gene List Preparation with VxInsight

A gene-by-gene comparison of expression levels between pairs of groups was computed using analysis of variance followed by a sort to put the genes into decreasing order by the resulting F-statistic. To estimate the stability of this gene list, two bootstrap calculations are made under the appropriate null hypotheses. First, we ask about the list stability given the groupings. In this case bootstraps are resampled with replacement from within the indicated groups and processed with analysis of variance, just as for the actual measurements. The collection of resulting gene orders is examined to determine the 95% confidence bands for the rankings of individual genes. Next we compute a p-value for the observed rankings under the null hypothesis that, Ho: there is no difference in gene expression between the two groups. When Ho is, indeed, true, the best empirical distribution would be the combination of all values without respect to their group labels. To test the hypothesis we create ten thousand bootstraps by sampling from the combined expression levels, ignoring the group labels. Each bootstrap is processed exactly the same as the original array measurements. A p-value is accumulated by counting the fraction of times that we observe a bootstrap where a gene's ranking is at or above its order in the real experiment.

Overlap of Cluster Methods

Clusters from each of the different methods were compared for maximum overlap. For the purposes of this analysis ROSE and COPA groups were considered to be the same, and the ROSE membership was used for the comparison. This analysis showed that several clusters of patients were common to each of the methods. In particular, clusters 1 (containing the MLL translocations), 2 (E2A-PBX1 translocations), 2A (similar to E2A-PBX1 translocations), 6 (good outcome patients) and 8 (poor outcome patients) exhibited the best overlap across all three methods. FIG. 2C highlights the membership similarity across the methods.

Table 2C gives the adjusted Rand indices showing the agreement across the three methods.[3] This illustrates that the ROSE and hierarchical clustering are the most closely related, although all three methods are significantly similar.

TABLE 2C

Adjusted Rand Indices for Clustering Method Comparison

|  | Rose Clusters | | Hierarchical Clusters | | VX Clusters | |
| --- | --- | --- | --- | --- | --- | --- |
|  | ARI | P | ARI | P | ARI | P |
| Rose Clusters | — | — | 0.4024 | <0.0001 | 0.1858 | <0.0001 |
| Hierarchical Clusters | 0.4024 | <0.0001 | — | — | 0.2180 | <0.0001 |
| VX Clusters | 0.1858 | <0.0001 | 0.2180 | <0.0001 | — | — |

Cohort Composition

Clinical Features of ROSE and Hierarchical Clusters

The variable "range" in Tables 3S and 4S refers to the values at the $10^{th}$ to $90^{th}$ percentiles.

TABLE 3S

Clinical features of ROSE clusters

| | | R1 | R2 | R2A | R4 | R5 | R6 | R7 | R8 | Total | P |
| --- | --- | --- | --- | --- | --- | --- | --- | --- | --- | --- | --- |
| Cases | | 21 | 23 | 11 | 13 | 11 | 21 | 83 | 24 | 207 | |
| Age | ≥10 Yrs | 9 (43%) | 15 (65%) | 10 (91%) | 10 (77%) | 10 (91%) | 18 (86%) | 42 (51%) | 18 (75%) | 132 (64%) | 0.001 |
| | <10 Yrs | 12 (57%) | 8 (35%) | 1 (9%) | 3 (23%) | 1 (9%) | 3 (14%) | 41 (49%) | 6 (25%) | 75 (36%) | |
| | Median | 4.67 | 13.09 | 15.32 | 13.95 | 14.67 | 14.45 | 10.92 | 14.11 | 13.09 | <0.001 |
| | range | 1.19-15.51 | 2.91-16.13 | 11.20-17.29 | 2.22-17.23 | 11.85-17.33 | 9.82-17.90 | 1.93-16.80 | 5.71-17.74 | 215-17.34 | |
| Sex | Female | 10 (48%) | 12 (52%) | 5 (45%) | 2 (15%) | 3 (27%) | 4 (19%) | 27 (33%) | 7 (29%) | 70 (34%) | 0.18 |
| | Male | 11 (52%) | 11 (48%) | 6 (55%) | 11 (85%) | 8 (73%) | 17 (81%) | 56 (67%) | 17 (71%) | 137 (66%) | |
| WBC | ≥50K | 16 (76%) | 12 (52%) | 4 (36%) | 2 (15%) | 5 (45%) | 9 (43%) | 46 (55%) | 14 (58%) | 108 (52%) | 0.039 |
| | <50K | 5 (24%) | 11 (48%) | 7 (64%) | 11 (85%) | 6 (55%) | 12 (57%) | 37 (45%) | 10 (42%) | 99 (48%) | |
| | Median (K/μL) | 125.8 | 67.2 | 27 | 13.3 | 32.6 | 26 | 68.6 | 153.8 | 62.3 | 0.007 |
| | range | 17.3-489.0 | 6.2-170.9 | 3.8-270.0 | 2.3-75.3 | 16.5-179.0 | 2.3-209.6 | 3.5-191.6 | 6.6-440.0 | 4.0-237.4 | |
| Race | Hispanic/Latino | 4 (19%) | 6 (26%) | 2 (18%) | 2 (15%) | 0 (0%) | 3 (15%) | 19 (23%) | 15 (62%) | 51 (25%) | 0.004 |
| | Others | 17 (81%) | 17 (74%) | 9 (82%) | 11 (85%) | 10 (100%) | 17 (85%) | 64 (77%) | 9 (38%) | 154 (75%) | |
| MLL | Negative | 0 (0%) | 23 (100%) | 11 (100%) | 13 (100%) | 11 (100%) | 21 (100%) | 83 (100%) | 24 (100%) | 186 (90%) | <0.001 |
| | Positive | 21 (100%) | 0 (0%) | 0 (0%) | 0 (0%) | 0 (0%) | 0 (0%) | 0 (0%) | 0 (0%) | 21 (10%) | |
| E2A/PBX | Negative | 21 (100%) | 0 (0%) | 11 (100%) | 13 (100%) | 11 (100%) | 21 (100%) | 83 (100%) | 24 (100%) | 184 (89%) | <0.001 |
| | Positive | 0 (0%) | 23 (100%) | 0 (0%) | 0 (0%) | 0 (0%) | 0 (0%) | 0 (0%) | 0 (0%) | 23 (11%) | |
| CNS | No blasts | 16 (76%) | 21 (91%) | 9 (82%) | 10 (77%) | 8 (73%) | 17 (81%) | 59 (71%) | 20 (83%) | 160 (77%) | 0.465 |
| | <5 blasts | 4 (19%) | 1 (4%) | 0 (0%) | 2 (15%) | 1 (9%) | 4 (19%) | 11 (13%) | 3 (12%) | 26 (13%) | |
| | ≥5 blasts | 1 (5%) | 1 (4%) | 2 (18%) | 1 (8%) | 2 (18%) | 0 (0%) | 13 (16%) | 1 (4%) | 21 (10%) | |
| D29 MRD | Negative | 8 (47%) | 20 (100%) | 8 (89%) | 11 (85%) | 3 (27%) | 15 (71%) | 55 (71%) | 4 (17%) | 124 (65%) | <0.001 |
| | Positive | 9 (53%) | 0 (0%) | 1 (11%) | 2 (15%) | 8 (73%) | 6 (29%) | 22 (29%) | 19 (83%) | 67 (35%) | |
| Relapse-free survival | 1 year | 0.762 | 0.913 | 0.909 | 1.000 | 1.000 | 1.000 | 0.976 | 0.915 | | <0.001 |
| | 2 years | 0.667 | 0.739 | 0.818 | 0.923 | 1.000 | 1.000 | 0.828 | | | |
| | 3 years | 0.667 | 0.739 | 0.818 | 0.846 | 0.900 | 0.947 | 0.766 | | | |
| | 4 years | 0.667 | 0.739 | 0.727 | 0.762 | 0.788 | 0.947 | 0.661 | 0.697 | | |
| | 5 years | 0.667 | 0.739 | 0.727 | 0.762 | 0.788 | 0.947 | 0.529 | 0.479 | | |

TABLE 4S

Clinical features of Hierarchical clusters

| | | H1 | H2 | H3 | H4 | H5 | H6 | H7 | H8 | Total | P |
|---|---|---|---|---|---|---|---|---|---|---|---|
| Cases | | 21 | 33 | 27 | 27 | 17 | 20 | 25 | 37 | 207 | |
| Age | ≥10 Yrs | 10 (48%) | 24 (73%) | 6 (22%) | 24 (89%) | 14 (82%) | 17 (85%) | 11 (44%) | 26 (70%) | 132 (64%) | <0.001 |
| | <10 Yrs | 11 (52%) | 9 (27%) | 21 (78%) | 3 (11%) | 3 (18%) | 3 (15%) | 14 (98%) | 11 (30%) | 75 (36%) | |
| | Median | 9.07 | 13.52 | 3.59 | 14.63 | 14.67 | 14.37 | 6.87 | 13.71 | 13.09 | <0.001 |
| | range | 1.26-15.51 | 3.35-17.28 | 1.35-14.24 | 9.58-17.23 | 7.44-17.36 | 9.44-17.94 | 1.84-17.08 | 3.37-17.82 | 2.15-17.34 | |
| Sex | Female | 9 (43%) | 17 (52%) | 11 (41%) | 3 (11%) | 5 (29%) | 4 (20%) | 9 (36%) | 12 (32%) | 70 (34%) | 0.042 |
| | Male | 12 (57%) | 16 (48%) | 16 (59%) | 24 (89%) | 12 (71%) | 16 (80%) | 16 (64%) | 25 (68%) | 137 (66%) | |
| WBC | ≥50K | 15 (71%) | 16 (48%) | 16 (59%) | 6 (22%) | 7 (41%) | 9 (45%) | 15 (60%) | 24 (65%) | 108 (52%) | 0.012 |
| | <50K | 6 (29%) | 17 (52%) | 11 (41%) | 21 (78%) | 10 (59%) | 11 (55%) | 10 (40%) | 13 (35%) | 99 (48%) | |
| | Median (K/μL) | 3 (14%) | 8 (24%) | 3 (11%) | 6 (22%) | 3 (19%) | 3 (16%) | 6 (24%) | 19 (51%) | 51 (25%) | 0.018 |
| | range | 18 (86%) | 25 (76%) | 24 (89%) | 21 (78%) | 13 (81%) | 16 (84%) | 19 (76%) | 18 (49%) | 154 (75%) | |
| Race | Hispanic/Latino | 3 (14%) | 8 (24%) | 3 (11%) | 6 (22%) | 3 (19%) | 3 (16%) | 6 (24%) | 19 (51%) | 51 (25%) | 0.018 |
| | Others | 18 (86%) | 25 (76%) | 24 (89%) | 21 (78%) | 13 (81%) | 16 (84%) | 19 (76%) | 18 (49%) | 154 (75%) | |
| MLL | Negative | 21 (100%) | 10 (30%) | 27 (100%) | 27 (100%) | 17 (100%) | 20 (100%) | 25 (100%) | 37 (100%) | 184 (89%) | <0.001 |
| | Positive | 0 (0%) | 23 (70%) | 0 (0%) | 0 (0%) | 0 (0%) | 0 (0%) | 0 (0%) | 0 (0%) | 23 (11%) | |
| E2A/PBX | Negative | 21 (100%) | 10 (30%) | 27 (100%) | 27 (100%) | 17 (100%) | 20 (100%) | 25 (100%) | 37 (100%) | 184 (89%) | <0.001 |
| | Positive | 0 (0%) | 23 (70%) | 0 (0%) | 0 (0%) | 0 (0%) | 0 (0%) | 0 (0%) | 0 (0%) | 23 (11%) | |
| CNS | No blasts | 16 (76%) | 29 (88%) | 16 (59%) | 23 (85%) | 12 (71%) | 16 (80%) | 20 (80%) | 28 (76%) | 160 (77%) | 0.102 |
| | <5 blasts | 4 (19%) | 1 (3%) | 3 (11%) | 2 (7%) | 3 (18%) | 4 (20%) | 2 (8%) | 7 (19%) | 26 (13%) | |
| | ≥5 blasts | 1 (5%) | 3 (9%) | 8 (30%) | 2 (7%) | 2 (12%) | | 3 (12%) | 2 (5%) | 21 (10%) | |
| D29 MRD | Negative | 8 (50%) | 28 (97%) | 16 (70%) | 19 (73%) | 9 (53%) | 14 (70%) | 18 (72%) | 12 (34%) | 124 (65%) | <0.001 |
| | Positive | 8 (50%) | 1 (3%) | 7 (30%) | 7 (27%) | 8 (47%) | 6 (30%) | 7 (28%) | 23 (66%) | 67 (35%) | |
| Relapse-free survival | 1 years | 0.762 | 0.909 | 1.000 | 0.962 | 1.000 | 1.000 | 0.960 | 0.945 | | 0.002 |
| | 2 years | 0.667 | 0.758 | 0.846 | 0.801 | 1.000 | 1.000 | 0.880 | 0.723 | | |
| | 3 years | 0.667 | 0.758 | 0.808 | 0.761 | 0.878 | 0.944 | 0.798 | 0.556 | | |
| | 4 years | 0.667 | 0.727 | 0.731 | 0.623 | 0.816 | 0.944 | 0.620 | 0.395 | | |
| | 5 years | 0.667 | 0.727 | 0.639 | 0.554 | 0.816 | 0.944 | 0.517 | 0.211 | | |

Comparison of 207 Samples to Entire Cohort

The 207 samples that were tested in this study were select from a total of 272 eligible patients on the basis of their availability. There were 65 patients for which the sample criteria for inclusions were not met. Typically, this reflected that the blast count was too low (<80%). In some cases this was due to insufficient amount of banked sample or failure or the sample to meet the microarray QC standards. In an effort to address whether the samples we tested are representative of the full cohort we compared the clinical variables of our 207 samples to the remaining 65. All variables except age and WBC count were evaluated by Fisher's exact test. Age and WBC counts were analyzed using Mann-Whitney rank sum testing. The following table reflects the raw numbers and associated p-values from these analyses. All variables not reaching significance at p<0.05 are shaded with gray.

TABLE 5S

Comparison of the 207 Tested Samples to the 65 Not Tested

| Variable | Value | 65 | 207 | Comparison | P |
|---|---|---|---|---|---|
| Sex | Male | 52/65 | 137/207 | M v F | 0.044 |
| Race | Caucasian | 33/62 | 126/205 | Cauc v known | 0.301 |
| | Hispanic | 15/62 | 51/205 | Hisp v known | 1.000 |
| | Black | 7/62 | 13/205 | Black v known | 0.267 |
| | Hawaiian | 1/62 | 1/205 | Hawaiian v known | 0.411 |
| | Asian | 3/62 | 7/205 | Asian v known | 0.702 |
| | Am. Indian | 2/62 | 3/205 | AmInd v known | 0.329 |
| | Other | 1/62 | 4/205 | Other v known | 1.000 |

TABLE 5S-continued

Comparison of the 207 Tested Samples to the 65 Not Tested

| Variable | Value | 65 | 207 | Comparison | P |
|---|---|---|---|---|---|
| MLL | Positive | 4/65 | 20/207 | Pos v Neg | 0.462 |
| TEL | Positive | 1/65 | 3/205 | Pos v Neg | 1.000 |
| TRISOM | Positive | 4/61 | 5/206 | Pos v Neg | 0.124 |
| E2A | Positive | 5/64 | 23/207 | Pos v Neg | 0.638 |
| CNS | Positive | 11/65 | 47/207 | Pos v Neg | 0.387 |
| TESTIC | Positive | 2/54 | 4/143 | Pos v Neg | 0.666 |
| CONGEN | Downs | 0/40 | 8/162 | Downs v known | 0.362 |
| D29 MRD | >0.01% | 40/59 | 124/191 | Pos v Neg | 0.755 |
| D8 MRD | >0.01% | 18/59 | 31/184 | Pos v Neg | 0.027 |
| AGE (days) | Median | 5056.0 | 4782.0 | Mann-Whitney | 0.026 |
| WBC | Median | 4.5 | 62.3 | Mann-Whitney | 0.000 |

Only four variables (age, WBC count, D8 MRD and sex) reached levels of significance. The WBC count by itself is indicative of why these samples were not included in the testing. The median WBC count for the 65 samples omitted from this study is 4.5 K/μL. This is more than ten fold lower than the median for the 207 samples that we tested and is even below the median WBC count for individuals without leukemia. The majority of the other variables are quite comparable between the two groups. None of the variables identified in this paper as having noteworthy correlations with specific clusters (Hispanic race, age and D29 MRD status, in particular) were significantly different between the two groups.

Probesets Used For Clustering

TABLE 6S

| 100 Probe sets used to define H-Groups | | | |
|---|---|---|---|
| Probe Set ID | Gene Symbol | Gene Title | Chrom |
| 1552924_a_at | PITPNM2 | phosphatidylinositol transfer protein, membrane-associated 2 | 12q24.31 |
| 1554026_a_at | MYO10 | myosin X | 5p15.1-p14.3 |
| 1555270_a_at | WFS1 | Wolfram syndrome 1 (wolframin) | 4p16 |
| 1556037_s_at | HHIP | hedgehog interacting protein | 4q28-q32 |
| 1557411_s_at | SLC25A43 | solute carrier family 25, member 43 | Xq24 |
| 1563335_at | IRGM | immunity-related GTPase family, M | 5q33.1 |
| 201105_at | LGALS1 | lectin, galactoside-binding, soluble, 1 (galectin 1) | 22q13.1 |
| 201212_at | LGMN | legumain | 14q32.1 |
| 201669_s_at | MARCKS | myristoylated alanine-rich protein kinase C substrate | 6q22.2 |
| 201876_at | PON2 | paraoxonase 2 | 7q21.3 |
| 202242_at | TSPAN7 | tetraspanin 7 | Xp11.4 |
| 202336_s_at | PAM | peptidylglycine alpha-amidating monooxygenase | 5q14-q21 |
| 202976_s_at | RHOBTB3 | Rho-related BTB domain containing 3 | 5q15 |
| 203434_s_at | MME | membrane metallo-endopeptidase | 3q25.1-q25.2 |
| 203948_s_at | MPO | myeloperoxidase | 17q23.1 |
| 204066_s_at | CENTG2 | centaurin, gamma 2 | 2p24.3-p24.1 |
| 204115_at | GNG11 | guanine nucleotide binding protein (G protein), gamma 11 | 7q21 |
| 204304_s_at | PROM1 | prominin 1 | 4p15.32 |
| 204438_at | MRC1 /// MRC1L1 | mannose receptor, C type 1 /// mannose receptor, C type 1-like 1 | 10p12.33 |
| 204439_at | IFI44L | interferon-induced protein 44-like | 1p31.1 |
| 204848_x_at | HBG1 /// HBG2 | hemoglobin, gamma A /// hemoglobin, gamma G | 11p15.5 |
| 204913_s_at | SOX11 | SRY (sex determining region Y)-box 11 | 2p25 |
| 205289_at | BMP2 | bone morphogenetic protein 2 | 20p12 |
| 205290_s_at | BMP2 | bone morphogenetic protein 2 | 20p12 |
| 206067_s_at | WT1 | Wilms tumor 1 | 11p13 |
| 207173_x_at | CDH11 | cadherin 11, type 2, OB-cadherin (osteoblast) | 16q22.1 |
| 207978_s_at | NR4A3 | nuclear receptor subfamily 4, group A, member 3 | 9q22 |
| 209167_at | GPM6B | glycoprotein M6B | Xp22.2 |
| 209191_at | TUBB6 | tubulin, beta 6 | 18p11.21 |
| 209480_at | HLA-DQB1 | major histocompatibility complex, class II, DQ beta 1 | 6p21.3 |
| 209959_at | NR4A3 | nuclear receptor subfamily 4, group A, member 3 | 9q22 |
| 210512_s_at | VEGFA | vascular endothelial growth factor A | 6p12 |
| 210517_s_at | AKAP12 | A kinase (PRKA) anchor protein (gravin) 12 | 6q24-q25 |
| 210993_s_at | SMAD1 | SMAD family member 1 | 4q31 |
| 211597_s_at | HOP | homeodomain-only protein | 4q11-q12 |
| 212154_at | SDC2 | syndecan 2 | 8q22-q23 |
| 212192_at | KCTD12 | potassium channel tetramerisation domain containing 12 | 13q22.3 |
| 212592_at | IGJ | Immunoglobulin J polypeptide, linker protein for immunoglobulin alpha and mu polypeptides | 4q21 |
| 213371_at | LDB3 | LIM domain binding 3 | 10q22.3-q23.2 |
| 213831_at | HLA-DQA1 | major histocompatibility complex, class II, DQ alpha 1 | 6p21.3 |
| 213880_at | LGR5 | leucine-rich repeat-containing G protein-coupled receptor 5 | 12q22-q23 |
| 213894_at | THSD7A | thrombospondin, type I, domain containing 7A | 7p21.3 |
| 214039_s_at | LAPTM4B | lysosomal associated protein transmembrane 4 beta | 8q22.1 |
| 214366_s_at | ALOX5 | arachidonate 5-lipoxygenase | 10q11.2 |
| 215028_at | SEMA6A | sema domain, transmembrane domain (TM), and cytoplasmic domain, (semaphorin) 6A | 5q23.1 |
| 215177_s_at | ITGA6 | integrin, alpha 6 | 2q31.1 |
| 215721_at | IGHG1 | immunoglobulin heavy constant gamma 1 (G1m marker) | 14q32.33 |
| 217022_s_at | IGHA1 /// IGHA2 | immunoglobulin heavy constant alpha 1 /// immunoglobulin heavy constant alpha 2 (A2m marker) | 14q32.33 |
| 218469_at | GREM1 | gremlin 1, cysteine knot superfamily, homolog (Xenopus laevis) | 15q13-q15 |
| 218625_at | NRN1 | neuritin 1 | 6p25.1 |
| 218793_s_at | SCML1 | sex comb on midleg-like 1 (Drosophila) | Xp22.2-p22.1 |
| 218880_at | FOSL2 | FOS-like antigen 2 | 2p23.3 |
| 218899_s_at | BAALC | brain and acute leukemia, cytoplasmic | 8q22.3 |
| 219666_at | MS4A6A | membrane-spanning 4-domains, subfamily A, member 6A | 11q12.1 |
| 220448_at | KCNK12 | potassium channel, subfamily K, member 12 | 2p22-p21 |
| 220450_at | hCG_1778643 | hCG1778643 | 4q31.22 |
| 222101_s_at | DCHS1 | dachsous 1 (Drosophila) | 11p15.4 |
| 222154_at | LOC26010 | viral DNA polymerase-transactivated protein 6 | 2q33.1 |
| 223449_at | SEMA6A | sema domain, transmembrane domain (TM), and cytoplasmic domain, (semaphorin) 6A | 5q23.1 |
| 223600_s_at | KIAA1683 | KIAA1683 | 19p13.1 |
| 223708_at | C1QTNF4 | C1q and tumor necrosis factor related protein 4 | 11q11 |
| 225496_s_at | SYTL2 | synaptotagmin-like 2 | 11q14 |
| 225548_at | SHROOM3 | shroom family member 3 | 4q21.1 |
| 225681_at | CTHRC1 | collagen triple helix repeat containing 1 | 8q22.3 |
| 225962_at | ZNRF1 | zinc and ring finger 1 | 16q23.1 |
| 226244_at | CLEC14A | C-type lectin domain family 14, member A | 14q21.1 |
| 226764_at | LOC152485 | hypothetical protein LOC152485 | 4q31.22 |
| 227361_at | HS3ST3B1 | heparan sulfate (glucosamine) 3-O-sulfotransferase 3B1 | 17p12-p11.2 |
| 227486_at | NT5E | 5'-nucleotidase, ecto (CD73) | 6q14-q21 |
| 227530_at | AKAP12 | A kinase (PRKA) anchor protein (gravin) 12 | 6q24-q25 |

TABLE 6S-continued

100 Probe sets used to define H-Groups

| Probe Set ID | Gene Symbol | Gene Title | Chrom |
|---|---|---|---|
| 227798_at | SMAD1 | SMAD family member 1 | 4q31 |
| 227923_at | SHANK3 | SH3 and multiple ankyrin repeat domains 3 | 22q13.3 |
| 228083_at | CACNA2D4 | calcium channel, voltage-dependent, alpha 2/delta subunit 4 | 12p13.33 |
| 228297_at | — | Transcribed locus | — |
| 228434_at | BTNL9 | butyrophilin-like 9 | 5q35.3 |
| 228667_at | AGPAT4 | 1-acylglycerol-3-phosphate O-acyltransferase 4 (lysophosphatidic acid acyltransferase, delta) | 6q26 |
| 228737_at | TOX2 | TOX high mobility group box family member 2 | 20q13.12 |
| 228854_at | — | Transcribed locus | — |
| 228988_at | ZNF711 | zinc finger protein 711 | Xq21.1-q21.2 |
| 229072_at | — | CDNA clone IMAGE:5259272 | — |
| 229830_at | — | Transcribed locus | — |
| 229902_at | FLT4 | fms-related tyrosine kinase 4 | 5q35.3 |
| 231935_at | ARPP-21 | cyclic AMP-regulated phosphoprotein, 21 kD | 3p22.3 |
| 232231_at | RUNX2 | runt-related transcription factor 2 | 6p21 |
| 235099_at | CMTM8 | CKLF-like MARVEL transmembrane domain containing 8 | 3p22.3 |
| 235652_at | — | CDNA FLJ37623 fis, clone BRCOC2014013 | — |
| 236203_at | — | — | — |
| 236918_s_at | LRRC34 | leucine rich repeat containing 34 | 3q26.2 |
| 238018_at | hCG_1990170 | hypothetical protein LOC285016 | 2p25.3 |
| 238429_at | TMEM71 | transmembrane protein 71 | 8q24.22 |
| 238919_at | — | Full-length cDNA clone CS0DF024YN04 of Fetal brain of *Homo sapiens* (human) | — |
| 240179_at | — | — | — |
| 240336_at | HBM | hemoglobin, mu | 16p13.3 |
| 241535_at | LOC728176 | hypothetical protein LOC728176 | 2p25.3 |
| 241844_x_at | TMEM156 | transmembrane protein 156 | 4p14 |
| 242468_at | — | — | — |
| 243756_at | — | — | — |
| 244413_at | CLECL1 | C-type lectin-like 1 | 12p13.31 |
| 244623_at | KCNQ5 | potassium voltage-gated channel, KQT-like subfamily, member 5 | 6q14 |
| 244665_at | — | Transcribed locus | — |

TABLE 7S

215 ROSE Probe sets used to define R-Groups

| Probe Set ID | Gene Symbol | Gene Title | Chrom |
|---|---|---|---|
| 1552398_a_at | CLEC12A | C-type lectin domain family 12, member A | 12p13.2 |
| 1552511_a_at | CPA6 | carboxypeptidase A6 | 8q13.2 |
| 1552767_a_at | HS6ST2 | heparan sulfate 6-O-sulfotransferase 2 | Xq26.2 |
| 1553963_at | RHOB | ras homolog gene family, member B | 2p24 |
| 1554343_a_at | STAP1 | signal transducing adaptor family member 1 | 4q13.2 |
| 1554633_a_at | MYT1L | myelin transcription factor 1-like | 2p25.3 |
| 1555579_s_at | PTPRM | protein tyrosine phosphatase, receptor type, M | 18p11.2 |
| 1555745_a_at | LYZ | lysozyme (renal amyloidosis) | 12q15 |
| 1556210_at | — | CDNA FLJ38810 fis, clone LIVER2006251 | — |
| 1557534_at | LOC339862 | hypothetical protein LOC339862 | 3p24.3 |
| 1558214_s_at | CTNNA1 | catenin (cadherin-associated protein), alpha 1, 102 kDa | 5q31 |
| 1558708_at | NRXN1 | neurexin 1 | 2p16.3 |
| 1559394_a_at | — | Full length insert cDNA clone ZC65D06 | — |
| 1559459_at | LOC613266 | hypothetical LOC613266 | 20p12.1 |
| 1559477_s_at | MEIS1 | Meis homeobox 1 | 2p14-p13 |
| 1561025_at | — | CDNA FLJ23762 fis, clone HEP18324 | — |
| 1561765_at | — | MRNA adjacent to 3' end of integrated HPV16 (INT475) | — |
| 1563396_x_at | — | *Homo sapiens*, clone IMAGE:4281761, mRNA | — |
| 1566825_at | — | CDNA FLJ31010 fis, clone HLUNG2000174 | — |
| 1567387_at | — | — | — |
| 1568603_at | CADPS | Ca2+-dependent secretion activator | 3p14.2 |
| 1569591_at | F11 | coagulation factor XI (plasma thromboplastin antecedent) | 4q35 |
| 200799_at | HSPA1A | heat shock 70 kDa protein 1A | 6p21.3 |
| 201105_at | LGALS1 | lectin, galactoside-binding, soluble, 1 (galectin 1) | 22q13.1 |
| 201579_at | FAT | FAT tumor suppressor homolog 1 (*Drosophila*) | 4q35 |
| 201656_at | ITGA6 | integrin, alpha 6 | 2q31.1 |
| 201842_s_at | EFEMP1 | EGF-contaIning fibulin-like extracellular matrix protein 1 | 2p16 |
| 202178_at | PRKCZ | protein kinase C, zeta | 1p36.33-p36.2 |
| 202207_at | ARL4C | ADP-ribosylation factor-like 4C | 2q37.1 |
| 202273_at | PDGFRB | platelet-derived growth factor receptor, beta polypeptide | 5q31-q32 |
| 202336_s_at | PAM | peptidylglycine alpha-amidating monooxygenase | 5q14-q21 |
| 202409_at | IGF2 /// INS-IGF2 | insulin-like growth factor 2 (somatomedin A) /// insulin- insulin-like growth factor 2 | 11p15.5 |

TABLE 7S-continued

215 ROSE Probe sets used to define R-Groups

| Probe Set ID | Gene Symbol | Gene Title | Chrom |
| --- | --- | --- | --- |
| 202411_at | IFI27 | interferon, alpha-inducible protein 27 | 14q32 |
| 202859_x_at | IL8 | interleukin 8 | 4q13-q21 |
| 202917_s_at | S100A8 | S100 calcium binding protein A8 | 1q21 |
| 202988_s_at | RGS1 | regulator of G-protein signaling 1 | 1q31 |
| 203290_at | HLA-DQA1 | major histocompatibility complex, class II, DQ alpha 1 | 6p21.3 |
| 203329_at | PTPRM | protein tyrosine phosphatase, receptor type, M | 18p11.2 |
| 203476_at | TPBG | trophoblast glycoprotein | 6q14-q15 |
| 203535_at | S100A9 | S100 calcium binding protein A9 | 1q21 |
| 203695_s_at | DFNA5 | deafness, autosomal dominant 5 | 7p15 |
| 203726_s_at | LAMA3 | laminin, alpha 3 | 18q11.2 |
| 203757_s_at | CEACAM6 | carcinoembryonic antigen-related cell adhesion molecule 6 (non-specific cross reacting antigen) | 19q13.2 |
| 203865_s_at | ADARB1 | adenosine deaminase, RNA-specific, B1 (RED1 homolog rat) | 21q22.3 |
| 203910_at | ARHGAP29 | Rho GTPase activating protein 29 | 1p22.1 |
| 203921_at | CHST2 | carbohydrate (N-acetylglucosamine-6-O) sulfotransferase 2 | 3q24 |
| 203948_s_at | MPO | myeloperoxidase | 17q23.1 |
| 203949_at | MPO | myeloperoxidase | 17q23.1 |
| 204014_at | DUSP4 | dual specificity phosphatase 4 | 8p12-p11 |
| 204066_s_at | CENTG2 | centaurin, gamma 2 | 2p24.3-p24.1 |
| 204069_at | MEIS1 | Meis homeobox 1 | 2p14-p13 |
| 204114_at | NID2 | nidogen 2 (osteonidogen) | 14q21-q22 |
| 204150_at | STAB1 | stabilin 1 | 3p21.1 |
| 204304_s_at | PROM1 | prominin 1 | 4p15.32 |
| 204419_x_at | HBG2 | hemoglobin, gamma G | 11p15.5 |
| 204439_at | IFI44L | interferon-induced protein 44-like | 1p31.1 |
| 204704_s_at | ALDOB | aldolase B, fructose-bisphosphate | 9q21.3-q22.2 |
| 204848_x_at | HBG1 /// HBG2 | hemoglobin, gamma A /// hemoglobin, gamma G | 11p15.5 |
| 204895_x_at | MUC4 | mucin 4, cell surface associated | 3q29 |
| 204913_s_at | SOX11 | SRY (sex determining region Y)-box 11 | 2p25 |
| 204914_s_at | SOX11 | SRY (sex determining region Y)-box 11 | 2p25 |
| 204915_s_at | SOX11 | SRY (sex determining region Y)-box 11 | 2p25 |
| 205239_at | AREG /// LOC727738 | amphiregulin (schwannoma-derived growth factor) /// similar to Amphiregulin precursor (AR) (Colorectum cell-derived growth factor) (CRDGF) | 4q13-q21 /// 4q13.3 |
| 205253_at | PBX1 | pre-B-cell leukemia homeobox 1 | 1q23 |
| 205347_s_at | TMSL8 | thymosin-like 8 | Xq21.33-q22.3 |
| 205413_at | MPPED2 | metallophosphoesterase domain containing 2 | 11p13 |
| 205445_at | PRL | prolactin | 6p22.2-p21.3 |
| 205489_at | CRYM | crystallin, mu | 16p13.11-p12.3 |
| 205656_at | PCDH17 | protocadherin 17 | 13q21.1 |
| 205844_at | VNN1 | vanin 1 | 6q23-q24 |
| 205899_at | CCNA1 | cyclin A1 | 13q12.3-q13 |
| 205950_s_at | CA1 | carbonic anhydrase I | 8q13-q22.1 |
| 206028_s_at | MERTK | c-mer proto-oncogene tyrosine kinase | 2q14.1 |
| 206067_s_at | WT1 | Wilms tumor 1 | 11p13 |
| 206070_s_at | EPHA3 | EPH receptor A3 | 3p11.2 |
| 206181_at | SLAMF1 | signaling lymphocytic activation molecule family member 1 | 1q22-q23 |
| 206258_at | ST8SIA5 | ST8 alpha-N-acetyl-neuraminide alpha-2,8-sialyltransferase 5 | 18q21.1 |
| 206298_at | ARHGAP22 | Rho GTPase activating protein 22 | 10q11.22 |
| 206310_at | SPINK2 | serine peptidase inhibitor, Kazal type 2 (acrosin-trypsin inhibitor) | 4q12 |
| 206413_s_at | TCL1B /// TCL6 | T-cell leukemia/lymphoma 1B /// T-cell leukemia/lymphoma 6 | 14q32.1 |
| 206478_at | KIAA0125 | KIAA0125 | 14q32.33 |
| 206633_at | CHRNA1 | cholinergic receptor, nicotinic, alpha 1 (muscle) | 2q24-q32 |
| 206952_at | G6PC | glucose-6-phosphatase, catalytic subunit | 17q21 |
| 207173_x_at | CDH11 | cadherin 11, type 2, OB-cadherin (osteoblast) | 16q22.1 |
| 207831_x_at | DHPS | deoxyhypusine synthase | 19p13.2-p13.1 |
| 208303_s_at | CRLF2 | cytokine receptor-like factor 2 | Xp22.3; Yp11.3 |
| 208567_s_at | KCNJ12 | potassium inwardly-rectifying channel, subfamily J, member 12 | 17p11.1 |
| 209101_at | CTGF | connective tissue growth factor | 6q23.1 |
| 209291_at | ID4 | inhibitor of DNA binding 4, dominant negative helix-loop-helix protein | 6p22-p21 |
| 209604_s_at | GATA3 | GATA binding protein 3 | 10p15 |
| 209875_s_at | SPP1 | secreted phosphoprotein 1 (osteopontin, bone sialoprotein I, early T-lymphocyte activation 1) | 4q21-q25 |
| 209897_s_at | SLIT2 | slit homolog 2 (Drosophila) | 4p15.2 |
| 209905_at | HOXA9 | homeobox A9 | 7p15-p14 |
| 210016_at | MYT1L | myelin transcription factor 1-like | 2p25.3 |
| 210150_s_at | LAMA5 | laminin, alpha 5 | 20q13.2-q13.3 |
| 210664_s_at | TFPI | tissue factor pathway inhibitor (lipoprotein-associated coagulation inhibitor) | 2q32 |
| 210665_at | TFPI | tissue factor pathway inhibitor (lipoprotein-associated coagulation inhibitor) | 2q32 |
| 210869_s_at | MCAM | melanoma cell adhesion molecule | 11q23.3 |
| 211341_at | POU4F1 | POU class 4 homeobox 1 | 13q31.1 |
| 211506_s_at | IL8 | interleukin 8 | 4q13-q21 |

TABLE 7S-continued

215 ROSE Probe sets used to define R-Groups

| Probe Set ID | Gene Symbol | Gene Title | Chrom |
|---|---|---|---|
| 211657_at | CEACAM6 | carcinoembryonic antigen-related cell adhesion molecule 6 (non-specific cross reacting antigen) | 19q13.2 |
| 212062_at | ATP9A | ATPase, Class II, type 9A | 20q13.2 |
| 212077_at | CALD1 | caldesmon 1 | 7q33 |
| 212094_at | PEG10 | paternally expressed 10 | 7q21 |
| 212148_at | PBX1 | pre-B-cell leukemia homeobox 1 | 1q23 |
| 212151_at | PBX1 | pre-B-cell leukemia homeobox 1 | 1q23 |
| 212192_at | KCTD12 | potassium channel tetramerisation domain containing 12 | 13q22.3 |
| 213005_s_at | ANKRD15 | ankyrin repeat domain 15 | 9p24.3 |
| 213150_at | HOXA10 | homeobox A10 | 7p15-p14 |
| 213258_at | TFPI | tissue factor pathway inhibitor (lipoprotein-associated coagulation inhibitor) | 2q32 |
| 213317_at | CLIC5 | chloride intracellular channel 5 | 6p21.1-p12.1 |
| 213362_at | PTPRD | protein tyrosine phosphatase, receptor type, D | 9p23-p24.3 |
| 213371_at | LDB3 | LIM domain binding 3 | 10q22.3-q23.2 |
| 213479_at | NPTX2 | neuronal pentraxin II | 7q21.3-q22.1 |
| 213515_x_at | HBG1 /// HBG2 | hemoglobin, gamma A /// hemoglobin, gamma G | 11p15.5 |
| 213714_at | CACNB2 | calcium channel, voltage-dependent, beta 2 subunit | 10p12 |
| 213844_at | HOXA5 | homeobox A5 | 7p15-p14 |
| 213880_at | LGR5 | leucine-rich repeat-containing G protein-coupled receptor 5 | 12q22-q23 |
| 214146_s_at | PPBP | pro-platelet basic protein (chemokine (C-X-C motif) ligand 7) | 4q12-q13 |
| 214537_at | HIST1H1D | histone cluster 1, H1d | 6p21.3 |
| 214651_s_at | HOXA9 | homeobox A9 | 7p15-p14 |
| 215177_s_at | ITGA6 | integrin, alpha 6 | 2q31.1 |
| 215379_x_at | IGL | immunoglobulin lambda locus | 22q11.1-q11.2 |
| 215692_s_at | MPPED2 | metallophosphoesterase domain containing 2 | 11p13 |
| 217109_at | MUC4 | mucin 4, cell surface associated | 3q29 |
| 217281_x_at | IL8 | interleukin 8 | 4q13-q21 |
| 217963_s_at | NGFRAP1 | nerve growth factor receptor (TNFRSF16) associated protein 1 | Xq22.2 |
| 218086_at | NPDC1 | neural proliferation, differentiation and control, 1 | 9q34.3 |
| 218847_at | IGF2BP2 | insulin-like growth factor 2 mRNA binding protein 2 | 3q27.2 |
| 219463_at | C20orf103 | chromosome 20 open reading frame 103 | 20p12 |
| 219489_s_at | NXN | nucleoredoxin | 17p13.3 |
| 220059_at | STAP1 | signal transducing adaptor family member 1 | 4q13.2 |
| 220377_at | FAM30A | family with sequence similarity 30, member A | 14q32.33 |
| 220416_at | ATP8B4 | ATPase, Class I, type 8B, member 4 | 15q21.2 |
| 221254_s_at | PITPNM3 | PITPNM family member 3 | 17p13 |
| 221417_x_at | EDG8 | endothelial differentiation, sphingolipid G-protein-coupled receptor, 8 | 19p13.2 |
| 221933_at | NLGN4X | neuroligin 4, X-linked | Xp22.32-p22.31 |
| 222934_s_at | CLEC4E | C-type lectin domain family 4, member E | 12p13.31 |
| 223121_s_at | SFRP2 | secreted frizzled-related protein 2 | 4q31.3 |
| 223216_x_at | FBXO16 /// ZNF395 | zinc finger protein 395 /// F-box protein 16 | 8p21.1 |
| 223786_at | CHST6 | carbohydrate (N-acetylglucosamine 6-O) sulfotransferase 6 | 16q22 |
| 224215_s_at | DLL1 | delta-like 1 (*Drosophila*) | 6q27 |
| 225483_at | VPS26B | vacuolar protein sorting 26 homolog B (*S. pombe*) | 11q25 |
| 225496_s_at | SYTL2 | synaptotagmin-like 2 | 11q14 |
| 225681_at | CTHRC1 | collagen triple helix repeat containing 1 | 8q22.3 |
| 226282_at | — | Full length insert cDNA clone ZE03F06 | — |
| 226415_at | KIAA1576 | KIAA1576 protein | 16q23.1 |
| 226733_at | PFKFB2 | 6-phosphofructo-2-kinase/fructose-2,6-biphosphatase 2 | 1q31 |
| 226913_s_at | SOX8 | SRY (sex determining region Y)-box 8 | 16p13.3 |
| 227099_s_at | LOC387763 | hypothetical LOC387763 | 11p11.2 |
| 227289_at | PCDH17 | protocadherin 17 | 13q21.1 |
| 227439_at | ANKS1B | ankyrin repeat and sterile alpha motif domain containing 1B | 12q23.1 |
| 227440_at | ANKS1B | ankyrin repeat and sterile alpha motif domain containing 1B | 12q23.1 |
| 227441_s_at | ANKS1B | ankyrin repeat and sterile alpha motif domain containing 1B | 12q23.1 |
| 227949_at | PHACTR3 | phosphatase and actin regulator 3 | 20q13.32 |
| 228017_s_at | C20orf58 | chromosome 20 open reading frame 58 | 20q13.33 |
| 228057_at | DDIT4L | DNA-damage-inducible transcript 4-like | 4q23 |
| 228262_at | MAP7D2 | MAP7 domain containing 2 | Xp22.12 |
| 228434_at | BTNL9 | butyrophilin-like 9 | 5q35.3 |
| 228462_at | IRX2 | iroquois homeobox 2 | 5p15.33 |
| 228863_at | PCDH17 | protocadherin 17 | 13q21.1 |
| 229233_at | NRG3 | neuregulin 3 | 10q22-q23 |
| 229461_x_at | NEGR1 | neuronal growth regulator 1 | 1p31.1 |
| 229638_at | IRX3 | iroquois homeobox 3 | 16q12.2 |
| 229661_at | SALL4 | sal-like 4 (*Drosophila*) | 20q13.13-q13.2 |
| 229975_at | — | Transcribed locus | — |
| 229985_at | BTNL9 | Butyrophilin-like 9 | 5q35.3 |
| 230110_at | MCOLN2 | mucolipin 2 | 1p22 |
| 230128_at | IGL@ | Immunoglobulin lambda locus | 22q11.1-q11.2 |
| 230130_at | SLIT2 | Slit homolog 2 (*Drosophila*) | 4p15.2 |
| 230472_at | IRX1 | iroquois homeobox 1 | 5p15.3 |
| 230537_at | — | — | — |

TABLE 7S-continued

215 ROSE Probe sets used to define R-Groups

| Probe Set ID | Gene Symbol | Gene Title | Chrom |
|---|---|---|---|
| 230687_at | SLC13A3 | solute carrier family 13 (sodium-dependent dicarboxylate transporter), member 3 | 20q12-q13.1 |
| 230803_s_at | ARHGAP24 | Rho GTPase activating protein 24 | 4q21.23-q21.3 |
| 230817_at | FAM84B | Family with sequence similarity 84, member B | 8q24.21 |
| 231040_at | — | CDNA FLJ43172 fis, clone FCBBF3007242 | — |
| 231166_at | GPR155 | G protein-coupled receptor 155 | 2q31.1 |
| 231223_at | CSMD1 | CUB and Sushi multiple domains 1 | 8p23.2 |
| 231257_at | TCERG1L | transcription elongation regulator 1-like | 10q26.3 |
| 231455_at | FLJ42418 | FLJ42418 protein | 2p25.2 |
| 231771_at | GJB6 | gap junction protein, beta 6 | 13q11-q12.1\|13q12 |
| 231899_at | ZC3H12C | zinc finger CCCH-type containing 12C | 11q22.3 |
| 232231_at | RUNX2 | runt-related transcription factor 2 | 6p21 |
| 232523_at | MEGF10 | multiple EGF-like-domains 10 | 5q33 |
| 232636_at | SLITRK4 | SLIT and NTRK-like family, member 4 | Xq27.3 |
| 232914_s_at | SYTL2 | synaptotagmin-like 2 | 11q14 |
| 233225_at | — | CDNA FLJ36087 fis, clone TESTI2020283 | — |
| 233847_x_at | — | Uncharacterized gastric protein ZA31P | — |
| 234261_at | — | MRNA; cDNA DKFZp761M10121 (from clone DKFZp761M10121) | — |
| 234945_at | FAM54A | family with sequence similarity 54, member A | 6q23.3 |
| 235521_at | HOXA3 | homeobox A3 | 7p15-p14 |
| 235625_at | VPS41 | vacuolar protein sorting 41 homolog (*S. cerevisiae*) | 7p14-p13 |
| 235666_at | ITGA8 | integrin, alpha 8 | 10p13 |
| 235911_at | LOC440995 | Hypothetical gene supported by BC034933; BC068085 | 3q29 |
| 235988_at | GPR110 | G protein-coupled receptor 110 | 6p12.3 |
| 236430_at | TMED6 | transmembrane emp24 protein transport domain containing 6 | 16q22.1 |
| 236489_at | — | Transcribed locus | — |
| 236773_at | — | Transcribed locus | — |
| 238018_at | hCG_1990170 | hypothetical protein LOC285016 | 2p25.3 |
| 238689_at | GPR110 | G protein-coupled receptor 110 | 6p12.3 |
| 239657_x_at | — | — | — |
| 240179_at | — | — | — |
| 240619_at | — | Transcribed locus | — |
| 240758_at | — | — | — |
| 241535_at | LOC728176 | hypothetical protein LOC728176 | 2p25.3 |
| 241647_x_at | — | Transcribed locus | — |
| 241960_at | CSMD1 | CUB and Sushi multiple domains 1 | 8p23.2 |
| 242172_at | MEIS1 | Meis homeobox 1 | 2p14-p13 |
| 242385_at | RORB | RAR-related orphan receptor B | 9q22 |
| 242457_at | — | Transcribed locus | — |
| 242468_at | — | — | — |
| 243533_x_at | — | — | — |
| 244665_at | — | Transcribed locus | — |
| 38487_at | STAB1 | stabilin 1 | 3p21.1 |
| 46665_at | SEMA4C | sema domain, immunoglobulin domain (Ig), transmembrane domain (TM) and short cytoplasmic domain, (semaphorin) 4C | 2q11.2 |

TABLE 8S

215 COPA Probe sets used to define C-Groups (6 XIST probe sets in gray font)

| Probe Set ID | Gene Symbol | Gene Title | Chrom |
|---|---|---|---|
| 1552398_a_at | CLEC12A | C-type lectin domain family 12, member A | 160364 |
| 1553613_s_at | FOXC1 | forkhead box C1 | 2296 |
| 1553629_a_at | FAM71B | family with sequence similarity 71, member B | 153745 |
| 1554343_a_at | STAP1 | signal transducing adaptor family member 1 | 26228 |
| 1554633_a_at | MYT1L | myelin transcription factor 1-like | 23040 |
| 1555579_s_at | PTPRM | protein tyrosine phosphatase, receptor type, M | 5797 |
| 1555745_a_at | LYZ | lysozyme (renal amyloidosis) | 4069 |
| 1557534_at | LOC339862 | hypothetical protein LOC339862 | 339862 |
| 1559477_s_at | MEIS1 | Meis homeobox 1 | 4211 |
| 1559696_at | — | Full length insert cDNA clone YW24B11 | — |
| 1566772_at | — | MRNA; cDNA DKFZp547L1918 (from clone DKFZp547L1918) | — |
| 1568603_at | CADPS | Ca2+-dependent secretion activator | 8618 |
| 200799_at | HSPA1A | heat shock 70 kDa protein 1A | 3303 |
| 200800_s_at | HSPA1A///HSPA1B | heat shock 70 kDa protein 1A///heat shock 70 kDa protein 1B | 3303///3304 |
| 201105_at | LGALS1 | lectin, galactoside-binding, soluble, 1 (galectin 1) | 3956 |
| 201215_at | PLS3 | plastin 3 (T isoform) | 5358 |
| 201579_at | FAT | FAT tumor suppressor homolog 1 (*Drosophila*) | 2195 |
| 201656_at | ITGA6 | integrin, alpha 6 | 3655 |
| 201842_s_at | EFEMP1 | EGF-containing fibulin-like extracellular matrix protein 1 | 2202 |
| 202018_s_at | LOC728320///LTF | lactotransferrin///similar to lactotransferrin | 4057///728320 |

TABLE 8S-continued

215 COPA Probe sets used to define C-Groups (6 XIST probe sets in gray font)

| Probe Set ID | Gene Symbol | Gene Title | Chrom |
|---|---|---|---|
| 202178_at | PRKCZ | protein kinase C, zeta | 5590 |
| 202411_at | IFI27 | interferon, alpha-inducible protein 27 | 3429 |
| 202859_x_at | IL8 | interleukin 8 | 3576 |
| 202917_s_at | S100A8 | S100 calcium binding protein A8 | 6279 |
| 203131_at | PDGFRA | platelet-derived growth factor receptor, alpha polypeptide | 5156 |
| 203153_at | IFIT1 | interferon-induced protein with tetratricopeptide repeats 1 | 3434 |
| 203290_at | HLA-DQA1 | major histocompatibility complex, class II, DQ alpha 1 | 3117 |
| 203329_at | PTPRM | protein tyrosine phosphatase, receptor type, M | 5797 |
| 203335_at | PHYH | phytanoyl-CoA 2-hydroxylase | 5264 |
| 203476_at | TPBG | trophoblast glycoprotein | 7162 |
| 203535_at | S100A9 | S100 calcium binding protein A9 | 6280 |
| 203695_s_at | DFNA5 | deafness, autosomal dominant 5 | 1687 |
| 203757_s_at | CEACAM6 | carcinoembryonic antigen-related cell adhesion molecule 6 (non-specific cross reacting antigen) | 4680 |
| 203865_s_at | ADARB1 | adenosine deaminase, RNA-specific, B1 (RED1 homolog rat) | 104 |
| 203921_at | CHST2 | carbohydrate (N-acetylglucosamine-6-O) sulfotransferase 2 | 9435 |
| 203948_s_at | MPO | myeloperoxidase | 4353 |
| 203949_at | MPO | myeloperoxidase | 4353 |
| 203973_s_at | CEBPD | CCAAT/enhancer binding protein (C/EBP), delta | 1052 |
| 204014_at | DUSP4 | dual specificity phosphatase 4 | 1846 |
| 204066_s_at | CENTG2 | centaurin, gamma 2 | 116987 |
| 204069_at | MEIS1 | Meis homeobox 1 | 4211 |
| 204114_at | NID2 | nidogen 2 (osteonidogen) | 22795 |
| 204134_at | PDE2A | phosphodiesterase 2A, cGMP-stimulated | 5138 |
| 204150_at | STAB1 | stabilin 1 | 23166 |
| 204273_at | EDNRB | endothelin receptor type B | 1910 |
| 204304_s_at | PROM1 | prominin 1 | 8842 |
| 204351_at | S100P | S100 calcium binding protein P | 6286 |
| 204363_at | F3 | coagulation factor III (thromboplastin, tissue factor) | 2152 |
| 204419_x_at | HBG2 | hemoglobin, gamma G | 3048 |
| 204439_at | IFI44L | interferon-induced protein 44-like | 10964 |
| 204469_at | PTPRZ1 | protein tyrosine phosphatase, receptor-type, Z polypeptide 1 | 5803 |
| 204482_at | CLDN5 | claudin 5 (transmembrane protein deleted in velocardiofacial syndrome) | 7122 |
| 204745_x_at | MT1G | metallothionein 1G | 4495 |
| 204848_x_at | HBG1///HBG2 | hemoglobin, gamma A///hemoglobin, gamma G | 3047///3048 |
| 204895_x_at | MUC4 | mucin 4, cell surface associated | 4585 |
| 204913_s_at | SOX11 | SRY (sex determining region Y)-box 11 | 6664 |
| 204914_s_at | SOX11 | SRY (sex determining region Y)-box 11 | 6664 |
| 204915_s_at | SOX11 | SRY (sex determining region Y)-box 11 | 6664 |
| 205239_at | AREG///LOC727738 | amphiregulin (schwannoma-derived growth factor)///similar to Amphiregulin precursor (AR) (Colorectum cell-derived growth factor) (CRDGF) | 374///727738 |
| 205253_at | PBX1 | pre-B-cell leukemia homeobox 1 | 5087 |
| 205347_s_at | TMSL8 | thymosin-like 8 | 11013 |
| 205445_at | PRL | prolactin | 5617 |
| 205489_at | CRYM | crystallin, mu | 1428 |
| 205656_at | PCDH17 | protocadherin 17 | 27253 |
| 205844_at | VNN1 | vanin 1 | 8876 |
| 205863_at | S100A12 | S100 calcium binding protein A12 | 6283 |
| 205899_at | CCNA1 | cyclin A1 | 8900 |
| 205950_s_at | CA1 | carbonic anhydrase I | 759 |
| 206070_s_at | EPHA3 | EPH receptor A3 | 2042 |
| 206258_at | ST8SIA5 | ST8 alpha-N-acetyl-neuraminide alpha-2,8-sialyltransferase 5 | 29906 |
| 206310_at | SPINK2 | serine peptidase inhibitor, Kazal type 2 (acrosin-trypsin inhibitor) | 6691 |
| 206413_s_at | TCL1B///TCL6 | T-cell leukemia/lymphoma 1B///T-cell leukemia/lymphoma 6 | 27004///9623 |
| 206461_x_at | MT1H///MT1P2 | metallothionein 1H///metallothionein 1 pseudogene 2 | 4496///645745 |
| 206478_at | KIAA0125 | KIAA0125 | 9834 |
| 206633_at | CHRNA1 | cholinergic receptor, nicotinic, alpha 1 (muscle) | 1134 |
| 206836_at | SLC6A3 | solute carrier family 6 (neurotransmitter transporter, dopamine), member 3 | 6531 |
| 207110_at | KCNJ12 | potassium inwardly-rectifying channel, subfamily J, member 12 | 3768 |
| 207173_x_at | CDH11 | cadherin 11, type 2, OB-cadherin (osteoblast) | 1009 |
| 208173_at | IFNB1 | interferon, beta 1, fibroblast | 3456 |
| 208303_s_at | CRLF2 | cytokine receptor-like factor 2 | 64109 |
| 208567_s_at | KCNJ12 | potassium inwardly-rectifying channel, subfamily J, member 12 | 3768 |
| 208581_x_at | MT1X | metallothionein 1X | 4501 |
| 208937_s_at | ID1 | inhibitor of DNA binding 1, dominant negative helix-loop-helix protein | 3397 |
| 209289_at | NFIB | nuclear factor I/B | 4781 |
| 209290_s_at | NFIB | nuclear factor I/B | 4781 |
| 209291_at | ID4 | inhibitor of DNA binding 4, dominant negative helix-loop-helix protein | 3400 |
| 209301_at | CA2 | carbonic anhydrase II | 760 |
| 209369_at | ANXA3 | annexin A3 | 306 |
| 209728_at | HLA-DRB4 | major histocompatibility complex, class II, DR beta 4 | 3126 |

TABLE 8S-continued

215 COPA Probe sets used to define C-Groups (6 XIST probe sets in gray font)

| Probe Set ID | Gene Symbol | Gene Title | Chrom |
|---|---|---|---|
| 209757_s_at | MYCN | v-myc myelocytomatosis viral related oncogene, neuroblastoma derived (avian) | 4613 |
| 209897_s_at | SLIT2 | slit homolog 2 (*Drosophila*) | 9353 |
| 209905_at | HOXA9 | homeobox A9 | 3205 |
| 210016_at | MYT1L | myelin transcription factor 1-like | 23040 |
| 210254_at | MS4A3 | membrane-spanning 4-domains, subfamily A, member 3 (hematopoietic cell-specific) | 932 |
| 210664_s_at | TFPI | tissue factor pathway inhibitor (lipoprotein-associated coagulation inhibitor) | 7035 |
| 210665_at | TFPI | tissue factor pathway inhibitor (lipoprotein-associated coagulation inhibitor) | 7035 |
| 211338_at | IFNA2 | interferon, alpha 2 | 3440 |
| 211456_x_at | MT1P2 | metallothionein 1 pseudogene 2 | 645745 |
| 211506_s_at | IL8 | interleukin 8 | 3576 |
| 211560_s_at | ALAS2 | aminolevulinate, delta-, synthase 2 (sideroblastic/hypochromic anemia) | 212 |
| 211597_s_at | HOP | homeodomain-only protein | 84525 |
| 211639_x_at | SKAP2 | Src kinase associated phosphoprotein 2 | 8935 |
| 211657_at | CEACAM6 | carcinoembryonic antigen-related cell adhesion molecule 6 (non-specific cross reacting antigen) | 4680 |
| 212062_at | ATP9A | ATPase, Class II, type 9A | 10079 |
| 212094_at | PEG10 | paternally expressed 10 | 23089 |
| 212104_s_at | RBM9 | RNA binding motif protein 9 | 23543 |
| 212148_at | PBX1 | pre-B-cell leukemia homeobox 1 | 5087 |
| 212151_at | PBX1 | pre-B-cell leukemia homeobox 1 | 5087 |
| 212185_x_at | MT2A | metallothionein 2A | 4502 |
| 212592_at | IGJ | Immunoglobulin J polypeptide, linker protein for immunoglobulin alpha and mu polypeptides | 3512 |
| 212859_x_at | MT1E | metallothionein 1E | 4493 |
| 213005_s_at | ANKRD15 | ankyrin repeat domain 15 | 23189 |
| 213258_at | TFPI | tissue factor pathway inhibitor (lipoprotein-associated coagulation inhibitor) | 7035 |
| 213317_at | CLIC5 | chloride intracellular channel 5 | 53405 |
| 213371_at | LDB3 | LIM domain binding 3 | 11155 |
| 213479_at | NPTX2 | neuronal pentraxin II | 4885 |
| 213515_x_at | HBG1///HBG2 | hemoglobin, gamma A///hemoglobin, gamma G | 3047///3048 |
| 213844_at | HOXA5 | homeobox A5 | 3202 |
| 214218_s_at | XIST | X (inactive)-specific transcript | 7503 |
| 214349_at | — | Transcribed locus | — |
| 214651_s_at | HOXA9 | homeobox A9 | 3205 |
| 214774_x_at | TOX3 | TOX high mobility group box family member 3 | 27324 |
| 215177_s_at | ITGA6 | integrin, alpha 6 | 3655 |
| 215214_at | IGL@ | Immunoglobulin lambda locus | 3535 |
| 215379_x_at | IGL@///IGLJ3///IGLV2-14///IGLV3-25 | immunoglobulin lambda locus///immunoglobulin lambda variable 3-25///immunoglobulin lambda variable 2-14///immunoglobulin lambda joining 3 | 28793///28815///28831///3535 |
| 215692_s_at | MPPED2 | metallophosphoesterase domain containing 2 | 744 |
| 215784_at | CD1E | CD1e molecule | 913 |
| 216336_x_at | MT1A///MT1M///MT1P2 | metallothionein 1A///metallothionein 1M///metallothionein 1 pseudogene 2 | 4489///4499///645745 |
| 216401_x_at | — | Immunoglobulin kappa light chain (IGKV gene), cell line JVM-2, clone 1 | — |
| 216491_x_at | IGHM | immunoglobulin heavy constant mu | 3507 |
| 216853_x_at | IGL@ | Immunoglobulin lambda locus | 3535 |
| 216984_x_at | IGL@ | Immunoglobulin lambda locus | 3535 |
| 217083_at | MAPKAPK5 | Mitogen-activated protein kinase-activated protein kinase 5 | 8550 |
| 217109_at | MUC4 | mucin 4, cell surface associated | 4585 |
| 217110_s_at | MUC4 | mucin 4, cell surface associated | 4585 |
| 217148_x_at | IGLV2-14 | immunoglobulin lambda variable 2-14 | 28815 |
| 217179_x_at | — | Anti-thyroglobulin light chain variable region | — |
| 217235_x_at | — | Immunoglobulin (mAb56) light chain V region mRNA, partial sequence | — |
| 217258_x_at | IVD | Isovaleryl Coenzyme A dehydrogenase | 3712 |
| 217963_s_at | NGFRAP1 | nerve growth factor receptor (TNFRSF16) associated protein 1 | 27018 |
| 219463_at | C20orf103 | chromosome 20 open reading frame 103 | 24141 |
| 219489_s_at | NXN | nucleoredoxin | 64359 |
| 220010_at | KCNE1L | KCNE1-like | 23630 |
| 220059_at | STAP1 | signal transducing adaptor family member 1 | 26228 |
| 220416_at | ATP8B4 | ATPase, Class I, type 8B, member 4 | 79895 |
| 221215_s_at | RIPK4 | receptor-interacting serine-threonine kinase 4 | 54101 |
| 221254_at | PITPNM3 | PITPNM family member 3 | 83394 |
| 221728_x_at | XIST | X (inactive)-specific transcript | 7503 |
| 221766_s_at | FAM46A | family with sequence similarity 46, member A | 55603 |
| 221933_at | NLGN4X | neuroligin 4, X-linked | 57502 |
| 222288_at | — | Transcribed locus, moderately similar to XP_517655.1 similar to KIAA0825 protein [Pan troglodytes] | — |

TABLE 8S-continued

215 COPA Probe sets used to define C-Groups (6 XIST probe sets in gray font)

| Probe Set ID | Gene Symbol | Gene Title | Chrom |
| --- | --- | --- | --- |
| 222934_s_at | CLEC4E | C-type lectin domain family 4, member E | 26253 |
| 223121_s_at | SFRP2 | secreted frizzled-related protein 2 | 6423 |
| 223278_at | GJB2 | gap Junction protein, beta 2, 26 kDa | 2706 |
| 223786_at | SFTPA1///SFTPA1B///SFTPA2///SFTPA2B | surfactant, pulmonary-associated protein A1B///surfactant, pulmonary-associated protein A2B///surfactant, pulmonary-associated protein A1///surfactant, pulmonary-associated protein A2 | 6435///6436///653509///729238 |
| 223786_at | CHST6 | carbohydrate (N-acetylglucosamine 6-O) sulfotransferase 6 | 4166 |
| 224215_s_at | DLL1 | delta-like 1 (*Drosophila*) | 28514 |
| 224588_at | XIST | X (inactive)-specific transcript | 7503 |
| 224589_at | XIST | X (inactive)-specific transcript | 7503 |
| 224590_at | XIST | X (inactive)-specific transcript | 7503 |
| 225496_s_at | SYTL2 | synaptotagmin-like 2 | 54843 |
| 255660_at | SEMA6A | sema domain, transmembrane domain (TM), and cytoplasmic domain, (semaphorin) 6A | 57556 |
| 225681_at | CTHRC1 | collagen triple helix repeat containing 1 | 115908 |
| 226282_at | — | Full length insert cDNA done ZE03F06 | — |
| 226415_at | KIAA1576 | KIAA1576 protein | 57687 |
| 226621_at | — | — | — |
| 226676_at | ZNF521 | zinc finger protein 521 | 25925 |
| 226677_at | ZNF521 | zinc finger protein 521 | 25925 |
| 226757_at | IFIT2 | interferon-induced protein with tetratricopeptide repeats 2 | 3433 |
| 226913_s_at | SOX8 | SRY (sex determining region Y)-box 8 | 30812 |
| 227099_s_at | LOC387763 | hypothetical LOC387763 | 387763 |
| 227289_at | PCDH17 | protocadherin 17 | 27253 |
| 227439_at | ANKS1B | ankyrin repeat and sterile alpha motif domain containing 1B | 56899 |
| 227441_s_at | ANKS1B | ankyrin repeat and sterile alpha motif domain containing 1B | 56899 |
| 227671_at | XIST | X (inactive)-specific transcript | 7503 |
| 227949_at | PHACTR3 | phosphatase and actin regulator 3 | 116154 |
| 228017_s_at | C20orf58 | chromosome 20 open reading frame 58 | 128414 |
| 228057_at | DDIT4L | DNA-damage-inducible transcript 4-like | 115265 |
| 228434_at | BTNL9 | butyrophilin-like 9 | 153579 |
| 228462_at | IRX2 | iroquois homeobox 2 | 153572 |
| 228854_at | — | Transcribed locus | — |
| 228863_at | PCDH17 | protocadherin 17 | 27253 |
| 229233_at | NRG3 | neuregulin 3 | 10718 |
| 229461_x_at | NEGR1 | neuronal growth regulator 1 | 257194 |
| 229638_at | IRX3 | iroquois homeobox 3 | 79191 |
| 229661_at | SALL4 | sal-like 4 (*Drosophila*) | 57167 |
| 229985_at | BTNL9 | Butyrophilin-like 9 | 153579 |
| 230128_at | IGL@ | Immunoglobulin lambda locus | 3535 |
| 230472_at | IRX1 | iroquois homeobox 1 | 79192 |
| 230537_at | — | — | — |
| 231040_at | — | CDNA FLJ43172 fis, clone FCBBF3007242 | — |
| 231223_at | CSMD1 | CUB and Sushi multiple domains 1 | 64478 |
| 231257_at | TCERG1L | transcription elongation regulator 1-like | 256536 |
| 231771_81 | GJB6 | gap junction protein, beta 6 | 10804 |
| 232231_at | RUNX2 | runt-related transcription factor 2 | 860 |
| 232523_at | MEGF10 | multiple EGF-like-domains 10 | 84466 |
| 235988_at | GPR110 | G protein-coupled receptor 110 | 266977 |
| 236489_at | — | Transcribed locus | — |
| 237613_at | FOXR1 | forkhead box R1 | 283150 |
| 238018_at | hCG_1990170 | hypothetical protein LOC285016 | 285016 |
| 238423_at | SYTL3 | synaptotagmin-like 3 | 94120 |
| 238689_at | GPR110 | G protein-coupled receptor 110 | 266977 |
| 238900_at | HLA-DRB1///HLA-DRB3///LOC730415 | major histocompatibility complex, class II, DR beta 1///major histocompatibility complex, class II, DR beta 3///hypothetical protein LOC730415 | 3123///3125///730415 |
| 240179_at | — | — | — |
| 240336_at | HBM | hemoglobin, mu | 3042 |
| 240758_at | — | — | — |
| 240794_at | NPAS4 | Neuronal PAS domain protein 4 | 266743 |
| 241960_at | CSMD1 | CUB and Sushi multiple domains 1 | 64478 |
| 242172_at | MEIS1 | Meis homeobox 1 | 4211 |
| 242457_at | — | Transcribed locus | — |
| 242468_at | — | — | — |
| 242747_at | — | — | — |
| 243533_x_at | — | — | — |
| 244463_at | ADAM23 | ADAM metallopeptidase domain 23 | 8745 |
| 244665_at | — | Transcribed locus | — |

Probesets Associated with Rose Clusters (by Average Rank Order)

TABLE 9S

| Top 50 R1 | | | | | |
|---|---|---|---|---|---|
| Probe Set ID | Rank | Gene | Gene Title | EntrezID | Chrom |
| 242172_at | 196 | MEIS1 | Meis homeobox 1 | 4211 | 2p14-p13 |
| 1559477_s_at | 196 | MEIS1 | Meis homeobox 1 | 4211 | 2p14-p13 |
| 204069_at | 194 | MEIS1 | Meis homeobox 1 | 4211 | 2p14-p13 |
| 219463_at | 193 | C20orf103 | chromosome 20 open reading frame 103 | 24141 | 20p12 |
| 235479_at | 193 | CPEB2 | cytoplasmic polyadenylation element binding protein 2 | 132864 | 4p15.33 |
| 1558111_at | 193 | MBNL1 | muscleblind-like (Drosophila) | 4154 | 3q25 |
| 226415_at | 190 | KIAA1576 | KIAA1576 protein | 57687 | 16q23.1 |
| 227877_at | 189 | C5orf39 | chromosome 5 open reading frame 39 | 389289 | 5p12 |
| 235879_at | 189 | MBNL1 | Muscleblind-like (Drosophila) | 4154 | 3q25 |
| 226939_at | 188 | CPEB2 | cytoplasmic polyadenylation element binding protein 2 | 132864 | 4p15.33 |
| 213844_at | 187 | HOXA5 | homeobox A5 | 3202 | 7p15-p14 |
| 202976_s_at | 186 | RHOBTB3 | Rho-related BTB domain containing 3 | 22836 | 5q15 |
| 202975_s_at | 186 | RHOBTB3 | Rho-related BTB domain containing 3 | 22836 | 5q15 |
| 232645_at | 185 | LOC153684 | hypothetical protein LOC153684 | 153684 | 5p12 |
| 225202_at | 185 | RHOBTB3 | Rho-related BTB domain containing 3 | 22836 | 5q15 |
| 241681_at | 185 | — | Transcribed locus | — | 3q25.2 |
| 242414_at | 184 | QPRT | quinolinate phosphoribosyltransferase (nicotinate-nucleotide pyrophosphorylase (carboxylating)) | 23475 | 16p11.2 |
| 1568589_at | 184 | — | Clone FLB3512 mRNA sequence | — | 10q21.3 |
| 209905_at | 184 | HOXA9 | homeobox A9 | 3205 | 7p15-p14 |
| 238712_at | 183 | — | Transcribed locus | — | 3p14.1 |
| 228365_at | 182 | CPNE8 | copine VIII | 144402 | 12q12 |
| 235291_s_at | 182 | FLJ32255 | hypothetical protein LOC643977 | 643977 | 5p12 |
| 201105_at | 182 | LGALS1 | lectin, galactoside-binding, soluble, 1 (galectin 1) | 3956 | 22q13.1 |
| 204044_at | 181 | QPRT | quinolinate phosphoribosyltransferase (nicotinate-nucleotide pyrophosphorylase (carboxylating)) | 23475 | 16p11.2 |
| 238498_at | 181 | — | MRNA full length Insert cDNA clone EUROIMAGE 1090207 | — | 6q23.3 |
| 219988_s_at | 181 | C1orf164 | chromosome 1 open reading frame 164 | 55182 | 1p34.1 |
| 205899_at | 181 | CCNA1 | cyclin A1 | 8900 | 13q12.3-q13 |
| 227235_at | 181 | — | CDNA clone IMAGE:5302158 | — | 4q32.1 |
| 209822_s_at | 180 | VLDLR | very low density lipoprotein receptor | 7436 | 9p24 |
| 1556657_at | 180 | — | CDNA FLJ36459 (fis, clone THYMU2014762 | — | 3q25.2 |
| 215163_at | 180 | — | — | — | 3q27.2 |
| 222409_at | 180 | CORO1C | coronin, actin binding protein, 1C | 23603 | 12q24.1 |
| 232298_at | 179 | hCG_1806964 | hCG1806964 | 401093 | 3q25.1 |
| 212588_at | 179 | PTPRC | protein tyrosine phosphatase, receptor type, C | 5788 | 1q31-q32 |
| 214651_s_at | 179 | HOXA9 | homeobox A9 | 3205 | 7p15-p14 |
| 204304_s_at | 179 | PROM1 | prominin 1 | 8842 | 4p15.32 |
| 204526_s_at | 179 | TBC1D8 | TBC1 domain family, member 8 (with GRAM domain) | 11138 | 2q11.2 |
| 210555_s_at | 179 | NFATC3 | nuclear factor of activated T-cells, cytoplasmic, calcineurin-dependent 3 | 4775 | 16q22.2 |
| 209825_s_at | 178 | UCK2 | uridine-cytidine kinase 2 | 7371 | 1q23 |
| 240180_at | 178 | — | MRNA full length insert cDNA clone EUROIMAGE 1090207 | — | 6q23.3 |
| 201875_s_at | 178 | LOC644387 /// MPZL1 | myelin protein zero-like 1 /// similar to myelin protein zero-like 1 isoform a | 644387 /// 9019 | 1q24.2 /// 7q11.21 |
| 202890_at | 178 | MAP7 | microtubule-associated protein 7 | 9053 | 6q23.3 |
| 201153_s_at | 178 | MBNL1 | muscleblind-like (Drosophila) | 4154 | 3q25 |
| 226568_at | 178 | FAM102B | family with sequence similarity 102, member B | 284611 | 1p13.3 |
| 213147_at | 178 | HOXA10 | homeobox A10 | 3206 | 7p15-p14 |
| 206289_at | 178 | HOXA4 | homeobox A4 | 3201 | 7p15-p14 |
| 243605_at | 178 | — | Transcribed locus | — | 4p15.33 |
| 234032_at | 178 | — | PRO1550 | — | 9p13.2 |
| 209101_at | 178 | CTGF | connective tissue growth factor | 1490 | 6q23.1 |
| 227534_at | 177 | C9orf21 | chromosome 9 open reading frame 21 | 195827 | 9q22.32 |

TABLE 10S

| Top 50 R2 | | | | | |
|---|---|---|---|---|---|
| Probe Set ID | Rank | Gene | Gene Title | EntrezID | Chrom |
| 212148_at | 196 | PBX1 | pre-B-cell leukemia homeobox 1 | 5087 | 1q23 |
| 212151_at | 196 | PBX1 | pre-B-cell leukemia homeobox 1 | 5087 | 1q23 |
| 205253_at | 195 | PBX1 | pre-B-cell leukemia homeobox 1 | 5087 | 1q23 |
| 206028_s_at | 195 | MERTK | c-mer proto-oncogene tyrosine kinase | 10461 | 2q14.1 |
| 225235_at | 195 | TSPAN17 | tetraspanin 17 | 26262 | 5q35.3 |
| 227439_at | 195 | ANKS1B | ankyrin repeat and sterile alpha motif domain containing | 56899 | 12q23.1 |

TABLE 10S-continued

Top 50 R2

| Probe Set ID | Rank | Gene | Gene Title | EntrezID | Chrom |
|---|---|---|---|---|---|
| 227440_at | 195 | ANKS1B | ankyrin repeat and sterile alpha motif domain containing 1B | 56899 | 12q23.1 |
| 227441_s_at | 195 | ANKS1B | ankyrin repeat and sterile alpha motif domain containing 1B | 56899 | 12q23.1 |
| 227949_at | 195 | PHACTR3 | phosphatase and actin regulator 3 | 116154 | 20q13.32 |
| 232289_at | 195 | KCNJ12 | potassium inwardly-rectifying channel, subfamily J, member 12 | 3768 | 17p11.1 |
| 234261_at | 195 | — | MRNA; cDNA DKFZp761M10121 (from clone DKFZp761M10121) | — | 12q23.1 |
| 202178_at | 194 | PRKCZ | protein kinase C, zeta | 5590 | 1p36.33-p36.2 |
| 202206_at | 194 | ARL4C | ADP-ribosylation factor-like 4C | 10123 | 2q37.1 |
| 202207_at | 194 | ARL4C | ADP-ribosylation factor-like 4C | 10123 | 2q37.1 |
| 204114_at | 194 | NID2 | nidogen 2 (osteonidogen) | 22795 | 14q21-q22 |
| 211913_s_at | 194 | MERTK | c-mer proto-oncogene tyrosine kinase | 10461 | 2q14.1 |
| 46665_at | 194 | SEMA4C | sema domain, immunoglobulin domain (Ig), transmembrane domain (TM) and short cytoplasmic domain, (semaphorin) 4C | 54910 | 2q11.2 |
| 224022_x_at | 194 | WNT16 | wingless-type MMTV integration site family, member 16 | 51384 | 7q31 |
| 225483_at | 194 | VPS26B | vacuolar protein sorting 26 homolog B (*S. pombe*) | 112936 | 11q25 |
| 235911_at | 194 | LOC440995 | Hypothetical gene supported by BC034933; BC068085 | 440995 | 3q29 |
| 238778_at | 194 | MPP7 | membrane protein, palmitoylated 7 (MAGUK p55 subfamily member 7) | 143098 | 10p11.23 |
| 201579_at | 193 | FAT | FAT tumor suppressor homolog 1 (*Drosophila*) | 2195 | 4q35 |
| 202208_s_at | 193 | ARL4C | ADP-ribosylation factor-like 4C | 10123 | 2q37.1 |
| 212789_at | 193 | NCAPD3 | non-SMC condensin II complex, subunit D3 | 23310 | 11q25 |
| 223693_s_at | 193 | FLJ10324 | FLJ10324 protein | 55698 | 7p22.1 |
| 229247_at | 193 | FLJ37440 | hypothetical protein FLJ37440 | 129804 | 2q13 |
| 206181_at | 192 | SLAMF1 | signaling lymphocytic activation molecule family member 1 | 6504 | 1q22-q23 |
| 209558_s_at | 192 | HIP1R /// LOC728014 | huntingtin interacting protein 1 related /// similar to huntingtin interacting protein 1 related | 728014 /// 9026 | 12q24 /// 12q24.31 |
| 213005_s_at | 192 | ANKRD15 | ankyrin repeat domain 15 | 23189 | 9p24.3 |
| 38340_at | 192 | HIP1R /// LOC728014 | huntingtin interacting protein 1 related /// similar to huntingtin interacting protein 1 related | 728014 /// 9026 | 12q24 /// 12q24.31 |
| 230306_at | 192 | VPS26B | vacuolar protein sorting 26 homoiog B (*S. pombe*) | 112936 | 11q25 |
| 204225_at | 191 | HDAC4 | histone deacetylase 4 | 9759 | 2q37.3 |
| 229770_at | 191 | GLT1D1 | glycosyltransferase 1 domain containing 1 | 144423 | 12q24.32 |
| 243533_x_at | 191 | — | — | — | 12q23.1 |
| 206255_at | 190 | BLK | B lymphoid tyrosine kinase | 640 | 8p23-p22 |
| 210150_s_at | 190 | LAMA5 | laminin, alpha 5 | 3911 | 20q13.2-q13.3 |
| 225313_at | 190 | C20orf177 | chromosome 20 open reading frame 177 | 63939 | 20q13.2-q13.33 |
| 231040_at | 190 | — | CDNA FLJ43172 fis, clone FCBBF3007242 | — | 9q21.13 |
| 242385_at | 190 | RORB | RAR-related orphan receptor B | 6096 | 9q22 |
| 200790_at | 189 | ODC1 | ornithine decarboxylase 1 | 4953 | 2p25 |
| 205159_at | 189 | CSF2RB | colony stimulating factor 2 receptor, beta, low-affinity (granulocyte-macrophage) | 1439 | 22q13.1 |
| 242957_at | 189 | VWCE | von Willebrand factor C and EGF domains | 220001 | 11q12.2 |
| 208567_s_at | 188 | KCNJ12 | potassium inwardly-rectifying channel, subfamily J, member 12 | 3768 | 17p11.1 |
| 1559394_a_at | 188 | — | Full length insert cDNA clone ZC65D06 | — | 1p31.3 |
| 215807_s_at | 187 | PLXNB1 | plexin B1 | 5364 | 3p21.31 |
| 220911_s_at | 187 | KIAA1305 | KIAA1305 | 57523 | 14q12 |
| 234985_at | 187 | LDLRAD3 | low density lipoprotein receptor class A domain containing 3 | 143458 | 11p13 |
| 235666_at | 187 | ITGA8 | integrin, alpha 8 | 8516 | 10p13 |
| 202478_at | 186 | TRIB2 | tribbles homobg 2 (*Drosophila*) | 28951 | 2p25.1-p24.3 |
| 204202_at | 186 | IQCE | IQ motif containing E | 23288 | 7p22.2 |

TABLE 11S

Top 50 R2A

| Probe Set ID | Rank | Gene | Gene Title | EntrezID | Chrom |
|---|---|---|---|---|---|
| 205659_at | 201 | HDAC9 | histone deacetylase 9 | 9734 | 7p21.1 |
| 217869_at | 201 | HSD17B12 | hydroxysteroid (17-beta) dehydrogenase 12 | 51144 | 11p11.2 |
| 230128_at | 199 | IGL@ | Immunoglobulin lambda locus | 3535 | 22q11.1-q11.2 |

TABLE 11S-continued

Top 50 R2A

| Probe Set ID | Rank | Gene | Gene Title | EntrezID | Chrom |
|---|---|---|---|---|---|
| 230968_at | 197 | — | Full-length cDNA clone CS0DF032YA11 of Fetal brain of Homo sapiens (human) | — | 7p21.1 |
| 242616_at | 197 | — | Transcribed locus | — | 11p11.2 |
| 225496_s_at | 195 | SYTL2 | synaptotagmin-like 2 | 54843 | 11q14 |
| 202780_at | 195 | OXCT1 | 3-oxoacid CoA transferase 1 | 5019 | 5p13.1 |
| 204852_s_at | 195 | PTPN7 | protein tyrosine phosphatase, non-receptor type 7 | 5778 | 1q32.1 |
| 225961_at | 194 | KLHDC5 | ketch domain containing 5 | 57542 | 12p11.22 |
| 213502_x_at | 194 | LOC91316 | similar to bK246H3.1 (immunoglobulin lambda-like polypeptide 1, pre-B-cell specific) | 91316 | 22q11.23 |
| 215946_x_at | 194 | CTA-246H3.1 | similar to omega protein | 91353 | 22q11.23 |
| 218942_at | 193 | PIP4K2C | phosphatidylinsoitol-5-phosphate 4-kinase, type II, gamma | 79837 | 12q13.3 |
| 204891_s_at | 193 | LCK | lymphocyte-specific protein tyrosine kinase | 3932 | 1p34.3 |
| 1552496_a_at | 192 | COBL | cordon-bleu homolog (mouse) | 23242 | 7p12.1 |
| 213050_at | 192 | COBL | cordon-bleu homolog (mouse) | 23242 | 7p12.1 |
| 232914_s_at | 191 | SYTL2 | synaptotagmin-like 2 | 54843 | 11q14 |
| 1552760_at | 191 | HDAC9 | histone deacetylase 9 | 9734 | 7p21.1 |
| 235802_at | 191 | PLD4 | phospholipase D family, member 4 | 122618 | 14q32.33 |
| 237625_s_at | 191 | — | Immunoglobulin light chain variable region complementarity determining region (CDR3) mRNA | — | 2p11.2 |
| 213243_at | 190 | VPS13B | vacuolar protein sorting 13 homolog B (yeast) | 157680 | 8q22.2 |
| 204890_s_at | 190 | LCK | lymphocyte-specific protein tyrosine kinase | 3932 | 1p34.3 |
| 205484_at | 189 | SIT1 | signaling threshold regulating transmembrane adaptor 1 | 27240 | 9p13-p12 |
| 203263_s_at | 189 | ARHGEF9 | Cdc42 guanine nucleotide exchange factor (GEF) 9 | 23229 | Xq11.1 |
| 242952_at | 189 | — | — | — | 7p21.1 |
| 221584_s_at | 189 | KCNMA1 | potassium large conductance calcium-activated channel, subfamily M, alpha member 1 | 3778 | 10q22.3 |
| 216218_s_at | 189 | PLCL2 | phospholipase C-like 2 | 23228 | 3p24.3 |
| 201216_at | 188 | ERP29 | endoplasmic reticulum protein 29 | 10961 | 12q24.13 |
| 213348_at | 188 | CDKN1C | cyclin-dependent kinase inhibitor 1C (p57, Kip2) | 1028 | 11p15.5 |
| 1557252_at | 188 | — | CDNA FLJ36213 fis, clone THYMU2000671 | — | 11p11.2 |
| 223059_s_at | 188 | FAM107B | family with sequence similarity 107, member B | 83641 | 10p13 |
| 213309_at | 188 | PLCL2 | phospholipase C-like 2 | 23228 | 3p24.3 |
| 221671_x_at | 188 | IGKC /// IGKV1-5 /// IGKV2-24 | immunoglobulin kappa constant /// immunoglobulin kappa variable 1-5 /// immunoglobulin kappa variable 2-24 | 28299 /// 28923 /// 3514 | 2p12 |
| 223017_at | 187 | TXNDC12 | thioredoxin domain containing 12 (endoplasmic reticulum) | 51060 | 1p32.3 |
| 203865_s_at | 187 | ADARB1 | adenosine deaminase, RNA-specific, B1 (RED1 homolog rat) | 104 | 21q22.3 |
| 235721_at | 187 | DTX3 | deltex 3 homolog (Drosophila) | 196403 | 12q13.3 |
| 241871_at | 187 | CAMK4 | calcium/calmodulin-dependent protein kinase IV | 814 | 5q21.3 |
| 221651_x_at | 187 | IGKC /// IGKV1-5 /// IGKV2-24 | immunoglobulin kappa constant /// immunoglobulin kappa variable 1-5 /// immunoglobulin kappa variable 2-24 | 28299 /// 28923 /// 3514 | 2p12 |
| 202844_s_at | 186 | RALBP1 | ralA binding protein 1 | 10928 | 18p11.3 |
| 214785_at | 186 | VPS13A | vacuolar protein sorting 13 homolog A (S. cerevisiae) | 23230 | 9q21 |
| 204129_at | 186 | BCL9 | B-cell CLL/lymphoma 9 | 607 | 1q21 |
| 229029_at | 186 | — | — | — | 5q22.1 |
| 1553423_a_at | 186 | SLFN13 | schlafen family member 13 | 146857 | 17q12 |
| 224795_x_at | 186 | IGKC /// IGKV1-5 /// IGKV2-24 | immunoglobulin kappa constant /// immunoglobulin kappa variable 1-5 /// immunoglobulin kappa variable 2-24 | 28299 /// 28923 /// 3514 | 2p12 |
| 219517_at | 185 | ELL3 | elongation factor RNA polymerase II-like 3 | 80237 | 15q15.3 |
| 226325_at | 185 | ADSSL1 | adenylosuccinate synthase like 1 | 122622 | 14q32.33 |
| 219737_s_at | 185 | PCDH9 | protocadherin 9 | 5101 | 13q14.3-q21.1 |
| 214677_x_at | 185 | IGL@ /// IGLJ3 /// IGLV2-14 /// IGLV3-25 /// IGLV4-3 | immunoglobulin lambda locus /// immunoglobulin lambda variable 4-3 /// immunoglobulin lambda variable 3-25 /// immunoglobulin lambda variable 2-14 /// immunoglobulin lambda joining 3 | 28786 /// 28793 /// 28815 /// 28831 /// 3535 | 22q11.1-q11.2 /// 22q11.2 |
| 203431_s_at | 185 | RICS | Rho GTPase-activating protein | 9743 | 11q24-q25 |
| 210791_s_at | 185 | RICS | Rho GTPase-activating protein | 9743 | 11q24-q25 |
| 214836_x_at | 185 | IGKC /// IGKV1-5 | immunoglobulin kappa constant /// immunoglobulin kappa variable 1-5 | 28299 /// 3514 | 2p12 |

TABLE 12S

| | | | Top 50 R4 | | |
|---|---|---|---|---|---|
| Probe Set ID | Rank | Gene | Gene Title | EntrezID | Chrom |
| 229661_at | 201 | SALL4 | sal-like 4 (*Drosophila*) | 57167 | 20q13.13-q13.2 |
| 212062_at | 201 | ATP9A | ATPase, Class II, type 9A | 10079 | 20q13.2 |
| 209602_s_at | 197 | GATA3 | GATA binding protein 3 | 2625 | 10p15 |
| 1554903_at | 196 | FRMD8 | FERM domain containing 8 | 83786 | 11q13 |
| 1554905_x_at | 196 | FRMD8 | FERM domain containing 8 | 83786 | 11q13 |
| 227595_at | 196 | ZMYM6 | zinc finger, MYM-type 6 | 9204 | 1p34.2 |
| 1559916_a_at | 195 | — | *Homo sapiens*, clone IMAGE:4723617, mRNA | — | 7p22.2 |
| 1556385_at | 195 | — | CDNA FLJ39926 fis, clone SPLEN2021157 | — | 11q13.1 |
| 209604_s_at | 194 | GATA3 | GATA binding protein 3 | 2625 | 10p15 |
| 216129_at | 194 | ATP9A | ATPase, Class II, type 9A | 10079 | 20q13.2 |
| 219999_at | 194 | MAN2A2 | mannosidase, alpha, class 2A, member 2 | 4122 | 15q26.1 |
| 218589_at | 193 | P2RY5 | purinergic receptor P2Y, G-protein coupled, 5 | 10161 | 13q14 |
| 243121_x_at | 193 | — | — | — | 19q13.41 |
| 214211_at | 192 | FTH1 /// FTHL16 | ferritin, heavy polypeptide 1 /// ferritin, heavy polypeptide-like 16 | 2495 /// 2508 | 11q13 |
| 202530_at | 192 | MAPK14 | mitogen-activated protein kinase 14 | 1432 | 6p21.3-p21.2 |
| 204689_at | 192 | HHEX | hematopoietically expressed homeobox | 3087 | 10q23.33 |
| 222620_s_at | 192 | DNAJC1 | DnaJ (Hsp40) homolog, subfamily C, member 1 | 64215 | 10p12.31 |
| 1564164_at | 192 | C1orf218 | chromosome 1 open reading frame 218 | 54530 | 1q31.3 |
| 235142_at | 191 | LOC730411 /// ZBTB8 | zinc finger and BTB domain containing 8 /// similar to zinc finger and BTB domain containing 8 | 653121 /// 730411 | 1p35.1 |
| 202499_s_at | 191 | SLC2A3 | solute carrier family 2 (facilitated glucose transporter), member 3 | 6515 | 12p13.3 |
| 201379_s_at | 191 | TPD52L2 | tumor protein D52-like 2 | 7165 | 20q13.2-q13.3 |
| 229744_at | 191 | SSFA2 | Sperm specific antigen 2 | 6744 | 2q31.3 |
| 1557948_at | 191 | LOC653583 /// PHLDB3 | pleckstrin homology-like domain, family B, member 3 /// similar to pleckstrin homology-like domain, family B, member 1 | 284345 /// 653583 | 19q13.31 |
| 225799_at | 191 | C2orf59 /// LOC541471 | chromosome 2 open reading frame 59 /// hypothetical LOC541471 | 112597 /// 541471 | 2p11.2 /// 2q13 |
| 218927_s_at | 190 | CHST12 | carbohydrate (chondroitin 4) sulfotransferase 12 | 55501 | 7p22 |
| 202032_s_at | 190 | MAN2A2 | mannosidase, alpha, class 2A, member 2 | 4122 | 15q26.1 |
| 222621_at | 190 | DNAJC1 | DnaJ (Hsp40) homolog, subfamily C, member 1 | 64215 | 10p12.31 |
| 205423_at | 189 | AP1B1 | adaptor-related protein complex 1, beta 1 subunit | 162 | 22q12|22q12.2 |
| 200677_at | 189 | PTTG1IP | pituitary tumor-transforming 1 interacting protein | 754 | 21q22.3 |
| 228297_at | 189 | — | Transcribed locus | — | 1p21.3 |
| 210665_at | 189 | TFPI | tissue factor pathway inhibitor (lipoprotein-associated coagulation inhibitor) | 7035 | 2q32 |
| 210664_s_at | 189 | TFPI | tissue factor pathway inhibitor (lipoprotein-associated coagulation inhibitor) | 7035 | 2q32 |
| 218189_s_at | 189 | NANS | N-acetylneuraminic acid synthase (sialic acid synthase) | 54187 | 9p24.1-p23 |
| 228188_at | 189 | — | — | — | 2p23.2 |
| 60471_at | 189 | RIN3 | Ras and Rab interactor 3 | 79890 | 14q32.12 |
| 1563473_at | 188 | — | MRNA; cDNA DKFZp761L0320 (from clone DKFZp761L0320) | — | 20q11.23 |
| 225262_at | 188 | FOSL2 | FOS-like antigen 2 | 2355 | 2p23.3 |
| 203322_at | 188 | ADNP2 | ADNP homeobox 2 | 22850 | 18q23 |
| 215933_s_at | 188 | HHEX | hematopoietically expressed homeobox | 3087 | 10q23.33 |
| 227594_at | 188 | ZMYM6 | zinc finger, MYM-type 6 | 9204 | 1p34.2 |
| 226691_at | 188 | KIAA1856 | KIAA1856 protein | 84629 | 7p22.1 |
| 233877_at | 188 | — | CDNA FLJ20770 fis, clone COL06509 | — | 3q26.2 |
| 1560031_at | 188 | FRMD4A | FERM domain containing 4A | 55691 | 10p13 |
| 242216_at | 188 | — | Transcribed locus | — | 10p12.31 |
| 219457_s_at | 188 | RIN3 | Ras and Rab interactor 3 | 79890 | 14q32.12 |
| 244665_at | 187 | — | Transcribed locus | — | 2q31.1 |
| 202498_s_at | 187 | SLC2A3 | solute carrier family 2 (facilitated glucose transporter), member 3 | 6515 | 12p13.3 |
| 229410_at | 187 | — | MRNA; cDNA DKFZp564G0462 (from clone DKFZp564G0462) | — | 19p13.11 |
| 200748_s_at | 187 | FTH1 /// FTHL11 /// FTHL16 | ferritin, heavy polypeptide 1 /// ferritin, heavy polypeptide-like 11 /// ferritln, heavy polypeptide-like 16 | 2495 /// 2503 /// 2508 | 11q13 /// 8q21.13 |
| 213258_at | 187 | TFPI | tissue factor pathway inhibitor (lipoprotein-associated coagulation inhibitor) | 7035 | 2q32 |

TABLE 13S

Top 50 R5

| Probe Set ID | Rank | Gene | Gene Title | EntrezID | Chrom |
|---|---|---|---|---|---|
| 213920_at | 185 | CUTL2 | cut-like 2 (*Drosophila*) | 23316 | 12q24.11-q24.12 |
| 224734_at | 184 | HMGB1 | high-mobility group box 1 | 3146 | 13q12 |
| 212751_at | 184 | UBE2N | ubiquitin-conjugating enzyme E2N (UBC13 homolog, yeast) | 7334 | 12q22 |
| 241774_at | 184 | — | Transcribed locus | — | 14q23.1 |
| 202947_s_at | 182 | GYPC | glycophorin C (Gerbich blood group) | 2995 | 2q14-q21 |
| 201524_x_at | 182 | UBE2N | ublquitin-conjugating enzyme E2N (UBC13 homolog, yeast) | 7334 | 12q22 |
| 218447_at | 182 | C16orf61 | chromosome 16 open reading frame 61 | 56942 | 16q23.2 |
| 242064_at | 181 | SDK2 | sidekick homolog 2 (chicken) | 54549 | 17q25.1 |
| 210473_s_at | 180 | GPR125 | G protein-coupled receptor 125 | 166647 | 4p15.31 |
| 200056_s_at | 179 | C1D /// LOC727879 | nuclear DNA-binding protein /// similar to nuclear DNA-binding protein | 10438 /// 727879 | 10q22.3 /// 2p13-p12 |
| 201119_s_at | 179 | COX8A | cytochrome c oxidase subunit 8A (ubiquitous) | 1351 | 11q12-q13 |
| 205839_s_at | 179 | BZRAP1 | benzodiazepine receptor (peripheral) associated protein 1 | 9256 | 17q22-q23 |
| 225073_at | 179 | PPHLN1 | periphilin 1 | 51535 | 12q12 |
| 203948_s_at | 178 | MPO | myeloperoxidase | 4353 | 17q23.1 |
| 239274_at | 178 | — | Transcribed locus | — | 11q14.2 |
| 208657_s_at | 178 | 39700 | septin 9 | 10801 | 17q25 |
| 204005_s_at | 178 | PAWR | PRKC, apoptosis, WT1, regulator | 5074 | 12q21 |
| 226101_at | 178 | PRKCE | protein kinase C, epsilon | 5581 | 2p21 |
| 213222_at | 177 | PLCB1 | phospholipase C, beta 1 (phosphoinositide-specific) | 23236 | 20p12 |
| 233873_x_at | 177 | PAPD1 | PAP associated domain containing 1 | 55149 | 10p11.23 |
| 201015_s_at | 177 | JUP | junction plakoglobin | 3728 | 17q21 |
| 202824_s_at | 177 | TCEB1 | transcription elongation factor B (SIII), polypeptide 1 (15 kDa, elongin C) | 6921 | 8q21.11 |
| 218023_s_at | 177 | FAM53C | family with sequence similarity 53, member C | 51307 | 5q31 |
| 208195_at | 177 | TTN | titin | 7273 | 2q31 |
| 202123_s_at | 176 | ABL1 | v-abl Abelson murine leukemia viral oncogene homolog 1 | 25 | 9q34.1 |
| 227433_at | 176 | KIAA2018 | KIAA2018 | 205717 | 3q13.2 |
| 217788_s_at | 176 | GALNT2 | UDP-N-acetyl-alpha-D-galactosamine:polypeptide N-acetylgalactosaminyltransferase 2 (GalNAc-T2) | 2590 | 1q41-q42 |
| 227846_at | 176 | GPR176 | G protein-coupled receptor 176 | 11245 | 15q14-q15.1 |
| 212229_s_at | 176 | FBXO21 | F-box protein 21 | 23014 | 12q24.22 |
| 203476_at | 176 | TPBG | trophoblast glycoprotein | 7162 | 6q14-q15 |
| 200786_at | 175 | PSMB7 | proteasome (prosome, macropain) subunit, beta type, 7 | 5695 | 9q34.11-q34.12 |
| 223598_at | 175 | RAD23B | RAD23 homolog B (*S. cerevisiae*) | 5887 | 9q31.2 |
| 201827_at | 175 | SMARCD2 | SWI/SNF related, matrix associated, actin dependent regulator of chromatin, subfamily d, member 2 | 6603 | 17q23-q24 |
| 201754_at | 175 | COX6C | cytochrome c oxidase subunit Vic | 1345 | 8q22-q23 |
| 205401_at | 175 | AGPS | alkylglycerone phosphate synthase | 8540 | 2q31.2 |
| 223991_s_at | 175 | GALNT2 | UDP-N-acetyl-alpha-D-galactosamine:polypeptide N-acetylgalactosaminyltransferase 2 (GalNAc-T2) | 2590 | 1q41-q42 |
| 211031_s_at | 174 | CLIP2 | CAP-GLY domain containing linker protein 2 | 7461 | 7q11.23 |
| 223101_s_at | 174 | ARPC5L | actin related protein 2/3 complex, subunit 5-like | 81873 | 9q33.3 |
| 225694_at | 174 | CRKRS | Cdc2-related kinase, arginine/serine-rich | 51755 | 17q12 |
| 222794_x_at | 174 | PAPD1 | PAP associated domain containing 1 | 55149 | 10p11.23 |
| 203949_at | 174 | MPO | myeloperoxidase | 4353 | 17q23.1 |
| 217584_at | 174 | NPC1 | Niemann-Pick disease, type C1 | 4864 | 18q11-q12 |
| 220684_at | 174 | TBX21 | T-box 21 | 30009 | 17q21.32 |
| 209232_s_at | 174 | DCTN5 | dynactin 5 (p25) | 84516 | 16p12.1 |
| 204872_at | 174 | TLE4 | transducin-like enhancer of split 4 (E(sp1) homolog, *Drosophila*) | 7091 | 9q21.31 |
| 236375_at | 174 | — | Transcribed locus | — | 3p22.2 |
| 224830_at | 174 | NUDT21 | nudix (nucleoside diphosphate linked moiety X)-type motif 21 | 11051 | 16q13 |
| 1553380_at | 174 | PARP15 | poly (ADP-ribose) polymerase family, member 15 | 165631 | 3q21.1 |
| 224221_s_at | 173 | VAV3 | vav 3 guanine nucleotide exchange factor | 10451 | 1p13.3 |
| 211678_s_at | 173 | ZNF313 | zinc finger protein 313 | 55905 | 20q13.13 |

TABLE 14S

Top 50 R6 (* denotes probe sets mapped to gene by UCSC Genome Browser)

| Probe Set ID | Rank | Gene | Gene Title | EntrezID | Chrom |
|---|---|---|---|---|---|
| 220059_at | 196 | STAP1 | signal transducing adaptor family member 1 | 26228 | 4q13.2 |
| 228240_at | 196 | CENTG2* | Full-length cDNA clone CS0DM002YA18 of Fetal liver of *Homo sapiens* (human) | — | 2q37.2 |
| 204066_s_at | 196 | CENTG2 | centaurin, gamma 2 | 116987 | 2p24.3-p24.1 |
| 233225_at | 196 | CENTG2* | CDNA FLJ36087 fis, clone TESTI2020283 | — | 2q37.2 |
| 206756_at | 196 | CHST7 | carbohydrate (N-acetylglucosamine 6-O) sulfotransferase 7 | 56548 | Xp11.23 |
| 240758_at | 195 | CENTG2* | — | — | 2q37.2 |
| 1554343_a_at | 195 | STAP1 | signal transducing adaptor family member 1 | 26228 | 4q13.2 |
| 230537_at | 194 | PCDH17* | — | — | 13q21.1 |
| 203921_at | 194 | CHST2 | carbohydrate (N-acetylglucosamine-6-O) sulfotransferase 2 | 9435 | 3q24 |
| 230179_at | 193 | LOC285812 | hypothetical protein LOC285812 | 285812 | 6p23 |
| 219821_s_at | 192 | GFOD1 | glucose-fructose oxidoreductase domain containing 1 | 54438 | 6pter-p22.1 |
| 1554486_a_at | 192 | C6orf114 | chromosome 6 open reading frame 114 | 85411 | 6p23 |
| 209593_s_at | 192 | TOR1B | torsin family 1, member B (torsin B) | 27348 | 9q34 |
| 203329_at | 191 | PTPRM | protein tyrosine phosphatase, receptor type, M | 5797 | 18p11.2 |
| 227289_at | 191 | PCDH17 | protocadherin 17 | 27253 | 13q21.1 |
| 1552398_a_at | 191 | CLEC12A | C-type lectin domain family 12, member A | 160364 | 12p13.2 |
| 242457_at | 191 | — | Transcribed locus | — | 5q21.1 |
| 205656_at | 190 | PCDH17 | protocadherin 17 | 27253 | 13q21.1 |
| 1555579_s_at | 190 | PTPRM | protein tyrosine phosphatase, receptor type, M | 5797 | 18p11.2 |
| 1556593_s_at | 189 | — | CDNA FLJ40061 fis, clone TESOP2000083 | — | 3q23 |
| 228863_at | 189 | PCDH17 | protocadherin 17 | 27253 | 13q21.1 |
| 202336_s_at | 188 | PAM | peptidylglycine alpha-amidating monooxygenase | 5066 | 5q14-q21 |
| 235968_at | 187 | CENTG2 | centaurin, gamma 2 | 116987 | 2p24.3-p24.1 |
| 225611_at | 187 | — | — | — | 5q12.3 |
| 210944_s_at | 187 | CAPN3 | calpain 3, (p94) | 825 | 15q15.1-q21.1 |
| 211340_s_at | 187 | MCAM | melanoma cell adhesion molecule | 4162 | 11q23.3 |
| 233038_at | 187 | CENTG2* | CDNA: FLJ22776 fis, clone KAIA1582 | — | 2q37.2 |
| 219470_x_at | 187 | CCNJ | cyclin J | 54619 | 10pter-q26.12 |
| 244665_at | 186 | ITGA6* | Transcribed locus | — | 2q31.1 |
| 230954_at | 186 | C20orf112 | chromosome 20 open reading frame 112 | 140688 | 20q11.1-q11.23 |
| 211890_x_at | 186 | CAPN3 | calpain 3, (p94) | 825 | 15q15.1-q21.1 |
| 226342_at | 186 | SPTBN1 | spectrin, beta, non-erythrocytic 1 | 6711 | 2p21 |
| 202746_at | 186 | ITM2A | integral membrane protein 2A | 9452 | Xq13.3-Xq21.2 |
| 209087_x_at | 186 | MCAM | melanoma cell adhesion molecule | 4162 | 11q23.3 |
| 223130_s_at | 186 | MYLIP | myosin regulatory light chain interacting protein | 29116 | 6p23-p22.3 |
| 228098_s_at | 185 | MYLIP | myosin regulatory light chain interacting protein | 29116 | 6p23-p22.3 |
| 225613_at | 184 | MAST4 | microtubule associated serine/threonine kinase family member 4 | 375449 | 5q12.3 |
| 40016_g_at | 184 | MAST4 | microtubule associated serine/threonine kinase family member 4 | 375449 | 5q12.3 |
| 232227_at | 184 | AF161442* | HSPC324 | — | 9q34.3 |
| 202747_s_at | 184 | ITM2A | integral membrane protein 2A | 9452 | Xq13.3-Xq21.2 |
| 228097_at | 184 | MYLIP | myosin regulatory light chain interacting protein | 29116 | 6p23-p22.3 |
| 229091_s_at | 184 | CCNJ | cyclin J | 54619 | 10pter-q26.12 |
| 204836_at | 184 | GLDC | glycine dehydrogenase (decarboxylating) | 2731 | 9p22 |
| 201656_at | 183 | ITGA6 | integrin, alpha 6 | 3655 | 2q31.1 |
| 215177_s_at | 183 | ITGA6 | integrin, alpha 6 | 3655 | 2q31.1 |
| 214475_x_at | 183 | CAPN3 | calpain 3, (p94) | 825 | 15q15.1-q21.1 |
| 1558621_at | 183 | CABLES1 | Cdk5 and Abl enzyme substrate 1 | 91768 | 18q11.2 |
| 229597_s_at | 183 | WDFY4 | WDFY family member 4 | 57705 | 10q11.23 |
| 231166_at | 183 | GPR155 | G protein-coupled receptor 155 | 151556 | 2q31.1 |
| 239956_at | 182 | — | CDNA FLJ40061 fis, clone TESOP2000083 | — | 3q23 |

TABLE 15S

Top 50 R8 (* denotes probe sets mapped to gene by UCSC Genome Browser)

| Probe Set ID | Rank | Gene | Gene Title | EntrezID | Chrom |
|---|---|---|---|---|---|
| 236489_at | 190 | GPR110* | Transcribed locus | — | 6p12.3 |
| 212592_at | 189 | IGJ | Immunoglobulin J polypeptide, linker protein for immunoglobulin alpha and mu polypeptides | 3512 | 4q21 |
| 217109_at | 189 | MUC4 | mucin 4, cell surface associated | 4585 | 3q29 |
| 240586_at | 188 | ENAM | Enamelin | 10117 | 4q13.3 |
| 205795_at | 188 | NRXN3 | neurexin 3 | 9369 | 14q31 |
| 238689_at | 186 | GPR110 | G protein-coupled receptor 110 | 266977 | 6p12.3 |
| 217110_s_at | 185 | MUC4 | mucin 4, cell surface associated | 4585 | 3q29 |
| 236750_at | 185 | NRXN3* | Transcribed locus | — | 14q31.1 |
| 242051_at | 185 | CD99* | Transcribed locus | — | Xp22.33; Yp11.31 |
| 204895_x_at | 184 | MUC4 | mucin 4, cell surface associated | 4585 | 3q29 |
| 201029_s_at | 184 | CD99 | CD99 molecule | 4267 | Xp22.32; Yp11.3 |
| 201028_s_at | 183 | CD99 | CD99 molecule | 4267 | Xp22.32; Yp11.3 |
| 229114_at | 182 | GAB1* | CDNA done IMAGE:4801326 | — | 14q31.21 |
| 206873_at | 182 | CA6 | carbonic anhydrase VI | 765 | 1p36.2 |
| 201876_at | 182 | PON2 | paraoxonase 2 | 5445 | 7q21.3 |
| 222154_s_at | 182 | LOC26010 | viral DNA polymerase-transactivated protein 6 | 26010 | 2q33.1 |
| 210830_s_at | 181 | PON2 | paraoxonase 2 | 5445 | 7q21.3 |
| 235988_at | 181 | GPR110 | G protein-coupled receptor 110 | 266977 | 6p12.3 |
| 216565_x_at | 181 | LOC391020 | interferon induced transmembrane protein pseudogene | 391020 | 1p36.11 |
| 215021_s_at | 180 | NRXN3 | neurexin 3 | 9369 | 14q31 |
| 225912_at | 179 | TP53INP1 | tumor protein p53 inducible nuclear protein 1 | 94241 | 8q22 |
| 226002_at | 178 | GAB1* | CDNA clone IMAGE:4801326 | — | 4q31.21 |
| 214022_s_at | 178 | IFITM1 | interferon induced transmembrane protein 1 (9-27) | 8519 | 11p15.5 |
| 212203_x_at | 178 | IFITM3 | interferon induced transmembrane protein 3 (1-8U) | 10410 | 11p15.5 |
| 1563357_at | 178 | SERPINB9* | MRNA; cDNA DKFZp564C203 (from clone DKF4564C203) | — | 6p25.2 |
| 225998_at | 177 | GAB1 | GRB2-associated binding protein 1 | 2549 | 4q31.21 |
| 201315_x_at | 177 | IFITM2 | interferon induced transmembrane protein 2 (1-8D) | 10581 | 11p15.5 |
| 201601_x_at | 177 | IFITM1 | interferon Induced transmembrane protein 1 (9-27) | 8519 | 11p15.5 |
| 230643_at | 177 | WNT9A | wingless-type MMTV integration site family, member 9A | 7483 | 1q42 |
| 212974_at | 177 | DENND3 | DENN/MADD domain containing 3 | 22898 | 8q24.3 |
| 203435_s_at | 177 | MME | membrane metallo-endopeptidase | 4311 | 3q25.1-q25.2 |
| 223741_s_at | 177 | TTYH2 | tweety homolog 2 (Drosophila) | 94015 | 17q24 |
| 212975_at | 177 | DENND3 | DENN/MADD domain containing 3 | 22898 | 8q24.3 |
| 207426_s_at | 176 | TNFSF4 | tumor necrosis factor (ligand) superfamily, member 4 (tax-transcriptionally activated glycoprotein 1, 34 kDa) | 7292 | 1q25 |
| 52731_at | 175 | FLJ20294 | hypothetical protein FLJ20294 | 55626 | 11p11.2 |
| 215028_at | 175 | SEMA6A | sema domain, transmembrane domain (TM), and cytoplasmic domain, (semaphorin) 6A | 57556 | 5q23.1 |
| 229649_at | 175 | NRXN3 | neurexin 3 | 9369 | 14q31 |
| 1559315_s_at | 175 | LOC144481 | hypothetical protein LOC144481 | 144481 | 12q22 |
| 205983_at | 174 | DPEP1 | dipeptidase 1 (renal) | 1800 | 16q24.3 |
| 226840_at | 174 | H2AFY | H2A histone family, member Y | 9555 | 5q31.3-q32 |
| 230161_at | 174 | CD99* | Transcribed locus | — | Xp22.33; Yp11.31 |
| 223304_at | 174 | SLC37A3 | solute carrier family 37 (glycerol-3-phosphate transporter), member 3 | 84255 | 7q34 |
| 218862_at | 174 | ASB13 | ankyrin repeat and SOCS box-containing 13 | 79754 | 10p15.1 |
| 213939_s_at | 173 | RUFY3 | RUN and FYVE domain containing 3 | 22902 | 4q13.3 |
| 207112_s_at | 173 | GAB1 | GRB2-assoclated binding protein 1 | 2549 | 4q31.21 |
| 227856_at | 173 | C4orf32 | chromosome 4 open reading frame 32 | 132720 | 4q25 |
| 238880_at | 173 | GTF3A | general transcription factor IIIA | 2971 | 13q12.3-q13.1 |
| 1569666_s_at | 173 | SLC37A3* | Homo sapiens, clone IMAGE:5581630, mRNA | — | 7q34 |
| 209365_s_at | 173 | ECM1 | extracellular matrix protein 1 | 1893 | 1q21 |
| 203373_at | 173 | SOCS2 | suppressor of cytokine signaling 2 | 8835 | 12q |

Acknowledgements

This work was supported by NIH DHHS Grants: NCI Strategic Partnerships to Evaluate Cancer Gene Signatures (SPECS) Program NCI U01 CA114762 (Principal Investigator: CW) and NCI U10CA98543 Supporting the Children's Oncology Group and Statistical Center (Principal Investigator: GR), The National Childhood Cancer Foundation, and a Leukemia and Lymphoma Society Specialized Center of Research (SCOR) Program Grant 7388-06 (PI: CW). University of New Mexico Cancer Center Shared Facilities: KUGR Genomics, Biostatistics, and Bioinformatics & Computational Biology, partially supported by NCI P30 CA118100, were critical for this work. We would like to thank Malcolm Smith for many helpful discussions and his organizational efforts related to this entire project.

Authorship

RCH performed research, analyzed and interpreted data, performed statistical analysis and wrote the manuscript; XW analyzed and interpreted data and performed statistical analysis; GSD analyzed and interpreted data; KA performed research and analyzed and interpreted data; KKD analyzed and interpreted data; EJB performed statistical analysis; IMC designed research and analyzed and interpreted data; CSW wrote the manuscript; WW wrote the manuscript; SRA analyzed and interpreted data; SPH designed research; MD designed research and performed statistical analysis; JP performed research; AJC performed research; MJB performed research; WPB designed research; WLC designed research; BC designed research; GHR designed research; DB performed research; CLW designed research and wrote the manuscript.

FIGURE LEGENDS

FIG. 2. Hierarchical heat map that identifies outlier clusters. In Panel A the 209 COPA probe sets are shown in rows and the 207 samples in columns. In Panel B the 215 ROSE probe sets are shown in rows. The colored boxes indicate the identification of significant clusters. The colored bars across the bottom denote translocations, outcome and race as described in FIG. 1.

FIG. 3. Kaplan-Meier plots for clusters with aberrant outcome. RFS survival are shown for cluster 6 (Panel A) and cluster 8 (Panel B) for patients identified by multiple algorithms. The data for all 207 samples are shown with a black line. yellow=H8, light blue=V8, red=R8 and magenta=C8.

FIG. 4. Validation of ROSE in CCG 1961 data set. In Panel A a heat map generated as described in FIG. 2B identifies groups of samples with similar patterns of genes expression. The colored boxes indicate the clusters with similarities to those shown in the primary data set. In Panel B the RFS curve for cluster R8 in Panel A is shown in red, while the RFS for samples not in that group is shown in black.

REFERENCES

1. Ries L A G, Melbert D, Krapcho M, et al. SEER Cancer Statistics Review, 1975-2005. NIH publication. Bethesda, Md.: National Cancer Institute, Bethesda, Md.; 2008:v.
2. Smith M, Arthur D, Camitta B, et al. Uniform approach to risk classification and treatment assignment for children with acute lymphoblastic leukemia. J Clin Oncol. 1996; 14:18-24.
3. Pieters R, Carroll W L. Biology and treatment of acute lymphoblastic leukemia. Pediatr Clin North Am. 2008; 55:1-20, ix.
4. Armstrong S A, Look A T. Molecular genetics of acute lymphoblastic leukemia. J Clin Oncol. 2005; 23:6306-6315.
5. Yeah E J, Ross M E, Shurtleff S A, et al. Classification, subtype discovery, and prediction of outcome in pediatric acute lymphoblastic leukemia by gene expression profiling. Cancer Cell. 2002; 1:133-143.
6. Moos P J, Raetz E A, Carlson M A, et al. Identification of gene expression profiles that segregate patients with childhood leukemia. Clin Cancer Res. 2002; 8:3118-3130.
7. Wilson C S, Davidson G S, Martin S B, et al. Gene expression profiling of adult acute myeloid leukemia identifies novel biologic clusters for risk classification and outcome prediction. Blood. 2006; 108:685-696.
8. Shuster J J, Camitta B M, Pullen J, et al. Identification of newly diagnosed children with acute lymphocytic leukemia at high risk for relapse. Cancer Res Ther Control. 1999; 9:101-107.
9. Borowitz M J, Devidas M, Hunger S P, et al. Clinical significance of minimal residual disease in childhood acute lymphoblastic leukemia and its relationship to other prognostic factors: A Children's Oncology Group study. Blood. 2008.
10. Nachman J B, Sather H N, Sensel M G, et al. Augmented post-induction therapy for children with high-risk acute lymphoblastic leukemia and a slow response to initial therapy. N Engl J Med. 1998; 338:1663-1671.
11. Seibel N L, Steinherz P G, Sather H N, et al. Early postinduction intensification therapy improves survival for children and adolescents with high-risk acute lymphoblastic leukemia: a report from the Children's Oncology Group. Blood. 2008; 111:2548-2555.
12. Borowitz M J, Pullen D J, Shuster J J, et al. Minimal residual disease detection in childhood precursor-B-cell acute lymphoblastic leukemia: relation to other risk factors. A Children's Oncology Group study. Leukemia. 2003; 17:1566-1572.
13. Davidson G S, Martin S, Boyack K W, et al. Robust Methods for Microarray Analysis. In: Akay M, ed. Genomics and Proteomics Engineering in Medicine and Biology. Hoboken, New Jersey: IEEE Press; Wiley; 2007:99-130.
14. Tomlins S A, Rhodes D R, Perner S, et al. Recurrent fusion of TMPRSS2 and ETS transcription factor genes in prostate cancer. Science. 2005; 310:644-648.
15. Bland J M, Altman D G. The log rank test. BMJ. 2004; 328:1073.
16. Armitage P, Berry G. Statistical methods in medical research (ed 3rd). Oxford; Boston: Blackwell Scientific Publications; 1994.
17. Bewick V, Cheek L, Ball J. Statistics review 12: survival analysis. Crit Care. 2004; 8:389-394.
18. Bhojwani D, Kang H, Menezes R X, et al. Gene expression signatures predictive of early response and outcome in high-risk childhood acute lymphoblastic leukemia: a Children's Oncology Group study. J Clin Oncol. 2008; in press.
19. Fine B M, Stanulla M, Schrappe M, et al. Gene expression patterns associated with recurrent chromosomal translocations in acute lymphoblastic leukemia. Blood. 2004; 103: 1043-1049.
20. van Delft F W, Bellotti T, Luo Z, et al. Prospective gene expression analysis accurately subtypes acute leukaemia in children and establishes a commonality between hyperdiploidy and t(12;21) in acute lymphoblastic leukaemia. Br J Haematol. 2005; 130:26-35.
21. Coustan-Smith E, Sancho J, Behm F G, et al. Prognostic importance of measuring early clearance of leukemic cells by flow cytometry in childhood acute lymphoblastic leukemia. Blood. 2002; 100:52-58.
22. Steinherz P G, Gaynon P S, Breneman J C, et al. Cytoreduction and prognosis in acute lymphoblastic leukemia—the importance of early marrow response: report from the Childrens Cancer Group. J Clin Oncol. 1996; 14:389-398.
23. Bhatia S, Sather H N, Heerema N A, Trigg M E, Gaynon P S, Robison L L. Racial and ethnic differences in survival of children with acute lymphoblastic leukemia. Blood. 2002; 100:1957-1964.
24. Pollock B H, DeBaun M R, Camitta B M, et al. Racial differences in the survival of childhood B-precursor acute lymphoblastic leukemia: a Pediatric Oncology Group Study. J Clin Oncol. 2000; 18:813-823.
25. Dworzak M N, Froschl G, Printz D, et al. CD99 expression in T-lineage ALL: implications for flow cytometric detection of minimal residual disease. Leukemia. 2004; 18:703-708.
26. Wilkerson A E, Glasgow M A, Hiatt K M. Immunoreactivity of CD99 in invasive malignant melanoma. J Cutan Pathol. 2006; 33:663-666.

27. Scotlandi K, Perdichizzi S, Bernard G, et al. Targeting CD99 in association with doxorubicin: an effective combined treatment for Ewing's sarcoma. Eur J Cancer. 2006; 42:91-96.
28. Chaturvedi P, Singh A P, Moniaux N, et al. MUC4 mucin potentiates pancreatic tumor cell proliferation, survival, and invasive properties and interferes with its interaction to extracellular matrix proteins. Mol Cancer Res. 2007; 5:309-320.
29. Moniaux N, Chaturvedi P, Varshney G C, et al. Human MUC4 mucin induces ultra-structural changes and tumorigenicity in pancreatic cancer cells. Br J Cancer. 2007; 97:345-357.
30. Juric D, Lacayo N J, Ramsey M C, et al. Differential gene expression patterns and interaction networks in BCR-ABL-positive and -negative adult acute lymphoblastic leukemias. J Clin Oncol. 2007; 25:1341-1349.
31. Kameda H, Ishigami H, Suzuki M, Abe T, Takeuchi T. Imatinib mesylate inhibits proliferation of rheumatoid synovial fibroblast-like cells and phosphorylation of Gab adapter proteins activated by platelet-derived growth factor. Clin Exp Immunol. 2006; 144:335-341.
32. Zukerberg L R, DeBernardo R L, Kirley S D, et al. Loss of cables, a cyclin-dependent kinase regulatory protein, is associated with the development of endometrial hyperplasia and endometrial cancer. Cancer Res. 2004; 64:202-208.
33. Zhang H, Duan H O, Kirley S D, Zukerberg L R, Wu C L. Aberrant splicing of cables gene, a CDK regulator, in human cancers. Cancer Biol Ther. 2005; 4:1211-1215.
34. Dong Q, Kirley S, Rueda B, Zhao C, Zukerberg L, Oliva E. Loss of cables, a novel gene on chromosome 18q, in ovarian cancer. Mod Pathol. 2003; 16:863-868.
35. Kirley S D, D'Apuzzo M, Lauwers G Y, Graeme-Cook F, Chung D C, Zukerberg L R. The Cables gene on chromosome 18Q regulates colon cancer progression in vivo. Cancer Biol Ther. 2005; 4:861-863.
36. Ross M E, Zhou X, Song G, et al. Classification of pediatric acute lymphoblastic leukemia by gene expression profiling. Blood. 2003; 102:2951-2959.
37. Mullighan C G, Miller C B, Su X, et al. ERG deletions define a novel subtype of B-progenitor acute lymphoblastic leukemia. Blood. 2007; 110:212 A-213A.
38. Hoffmann K, Firth M J, Beesley A H, et al. Prediction of relapse in paediatric pre-B acute lymphoblastic leukaemia using a three-gene risk index. Br J Haematol. 2008; 140: 656-664.

The invention claimed is:
1. A method for treating high risk B-precursor acute lymphoblastic leukemia (B-ALL) in a patient in need comprising:
  A). determining whether said patient is a candidate for traditional therapy for B-ALL comprising
    i) obtaining a biological sample from said patient;
    ii) analyzing said sample to determine the expression level of the gene products MUC4 (Mucin 4) and IGJ (immunoglobulin J) in said sample; and
    iii) comparing the observed gene expression levels for each of said gene products to a control gene expression level selected from the group consisting of:
      a) the gene expression level for the gene products observed in a control sample; and
      b) a predetermined gene expression level for the gene products;
        wherein an observed expression level that is higher than the control gene expression for both of said gene products is indicative of therapeutic failure with traditional leukemia therapy; and
  B). treating B-ALL in said patient with non-traditional leukemia therapy if the observed expression level is higher than control level.
2. The method according to claim 1 wherein an observed expression level of at least one additional gene product selected from the group consisting of CRLF2 (cytokine receptor-like factor 2) and GPR110 (G protein-coupled receptor 110) which is greater than said control expression level is indicative of therapeutic failure with traditional leukemia therapy.
3. The method according to claim 2 wherein said one additional gene product is CRLF2.
4. The method according to claim 2 wherein said one additional gene product is GPR110.
5. The method according to claim 2 wherein said additional gene product is CRLF2 and GPR110.
6. The method according to claim 1 wherein said traditional leukemia therapy is Memorial Sloan Kettering New York II (NYII), UKALLr2, AL841, AL851, ALHR88, MCP841, modified BMF, BMF-95 or ALinC 17.
7. The method according to claim 1 wherein said non-traditional therapy is a more aggressive traditional therapy.
8. The method according to claim 1 wherein said non-traditional therapy is a more aggressive NYII therapy.
9. The method according to claim 1 wherein said non-traditional therapy is a more aggressive UKALLr2 therapy.
10. The method according to claim 1 wherein said non-traditional therapy is a more aggressive AL841 therapy.
11. The method according to claim 1 wherein said non-traditional therapy is a more aggressive AL851 therapy.
12. The method according to claim 1 wherein said non-traditional therapy is a more aggressive ALHR88 therapy.
13. The method according to claim 1 wherein said non-traditional therapy is a more aggressive MCP841 therapy.
14. The method according to claim 1 wherein said non-traditional therapy is a more aggressive modified BMF therapy.
15. The method according to claim 1 wherein said non-traditional therapy is a more aggressive BMF-95 therapy.
16. The method according to claim 1 wherein said non-traditional therapy is a more aggressive ALinC 17 therapy.
17. The method according to claim 1 wherein said non-traditional therapy is an experimental leukemia therapy.
18. The method according to claim 1 wherein said predetermined value is obtained from a sample of patients with high risk B-ALL who have been cured with traditional leukemia therapy.
19. The method according to claim 1 wherein said control is obtained from a sample of patients who are non-leukemic.
20. A method for predicting therapeutic outcome in a patient with high risk B-precursor acute lymphoblastic leukemia (B-ALL) patient comprising:
  (A) obtaining a biological sample from said patient;
  (B) analyzing said sample to determine the expression level of the gene products MUC4 (Mucin 4) and IGJ (immunoglobulin J) and at least one additional gene product selected from the group consisting of CRLF2 (cytokine receptor-like factor 2) and GPR110 (G protein-coupled receptor 110) in said sample; and
  C) comparing the observed gene expression levels for each of said gene products to a control gene expression level selected from the group consisting of:
    i) the gene expression level for the gene products observed in a control sample; and
    ii) a predetermined gene expression level for the gene products;

wherein an observed expression level of all of the gene products analyzed that is higher than the control gene expression level for said gene products indicates therapeutic failure with traditional leukemia therapy in said patient and said patient is treated with non-traditional leukemia therapy.

21. The method according to claim 20 wherein said additional gene product is CRLF2 and GPR110.

22. The method according to claim 20 wherein said one additional gene product is CRLF2.

23. The method according to claim 20 wherein said one additional gene product is GPR110.

24. The method according to claim 20 wherein said predetermined expression level is obtained from a sample of patients with high risk B-ALL who have been cured with traditional leukemia therapy.

25. The method according to claim 20 wherein said control sample is obtained from a sample of patients who are non-leukemic.

* * * * *